United States Patent
Wang et al.

(10) Patent No.: US 10,087,195 B2
(45) Date of Patent: Oct. 2, 2018

(54) CERTAIN PROTEIN KINASE INHIBITORS

(71) Applicants: Shanghai Fochon Pharmaceutical Co., Ltd., Shanghai (CN); CHONGQING FOCHON PHARMACEUTICAL CO., LTD., Chongqing (CN)

(72) Inventors: Weibo Wang, Moraga, CA (US); Xingdong Zhao, Moraga, CA (US); Tongshuang Li, Surrey (CA); Qiang Tian, Chongqing (CN); Huajie Zhang, Chongqing (CN); Haohan Tan, Chongqing (CN); Xianlong Wang, Chongqing (CN); Qihong Liu, Chongqing (CN); Zhifu Li, Chongqing (CN); Weipeng Zhang, Chongqing (CN); Zhifang Chen, Chongqing (CN); Lihua Jiang, Chongqing (CN); Yanxin Liu, Chongqing (CN); Li Linghu, Chongqing (CN); Min Lin, Chongqing (CN); Jing Sun, Chongqing (CN)

(73) Assignees: SHANGHAI FOCHON PHARMACEUTICAL CO., LTD., Shanghai (CN); CHONGQING FOCHON PHARMACEUTICAL CO., LTD., Chongqing (CN)

( * ) Notice: Subject to any disclaimer, the term of this patent is extended or adjusted under 35 U.S.C. 154(b) by 0 days.

(21) Appl. No.: 15/314,006

(22) PCT Filed: May 27, 2015

(86) PCT No.: PCT/CN2015/079910
§ 371 (c)(1),
(2) Date: Nov. 25, 2016

(87) PCT Pub. No.: WO2015/180642
PCT Pub. Date: Dec. 3, 2015

(65) Prior Publication Data
US 2017/0267696 A1  Sep. 21, 2017

Related U.S. Application Data

(60) Provisional application No. 62/003,626, filed on May 28, 2014.

(51) Int. Cl.
| | | |
|---|---|---|
| C07D 487/04 | (2006.01) |
| C07D 401/12 | (2006.01) |
| C07D 401/14 | (2006.01) |
| C07D 403/12 | (2006.01) |
| C07D 403/14 | (2006.01) |
| A61K 31/519 | (2006.01) |
| C07D 519/00 | (2006.01) |
| C07D 495/04 | (2006.01) |
| A61K 31/53 | (2006.01) |
| C07D 491/048 | (2006.01) |
| A61K 31/5377 | (2006.01) |
| A61P 35/00 | (2006.01) |

(52) U.S. Cl.
CPC .......... *C07D 519/00* (2013.01); *A61K 31/519* (2013.01); *A61K 31/53* (2013.01); *A61K 31/5377* (2013.01); *C07D 401/12* (2013.01); *C07D 401/14* (2013.01); *C07D 403/12* (2013.01); *C07D 403/14* (2013.01); *C07D 487/04* (2013.01); *C07D 491/048* (2013.01); *C07D 495/04* (2013.01)

(58) Field of Classification Search
CPC .. C07D 487/04; C07D 401/12; C07D 401/14; C07D 403/12; C07D 403/14; A61K 31/519
USPC ...................... 544/278; 514/260.1
See application file for complete search history.

(56) References Cited

PUBLICATIONS

Cecil Textbook of Medicine, edited by Bennet, J.C., and Plum F., 20th edition,vol. 1, 1004-101 O, 1996.*
Freshney et al.,Culture of Animal Cells, A Manual of Basic Technique, Alan R. Liss, Inc., 1983, New York, p. 4.*
Dermeret al., Bio/Technology, 1994, 12:320.*
Golub et al., Science, 286, 531-537, 1999.*
Cohen et al., Current Opinion in Chemical Biology, 3,459-465, 1999.*

* cited by examiner

*Primary Examiner* — Venkataraman Balasubramanian
(74) *Attorney, Agent, or Firm* — Meng H. Pua; Foley & Lardner LLP

(57) ABSTRACT

Provided are compound of formula (I) as certain CDK4/6 inhibitors, pharmaceutical compositions thereof, and methods of use thereof.

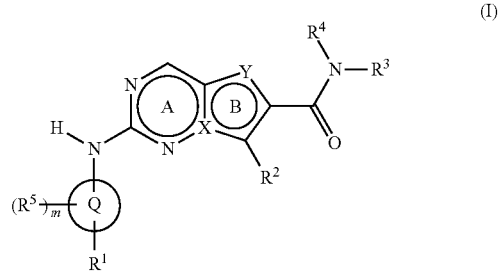

14 Claims, No Drawings

CERTAIN PROTEIN KINASE INHIBITORS

RELATED APPLICATIONS

This application is the U.S. National Stage of International Patent Application Number PCT/CN2015/079910, filed May 27, 2015, which claims priority to and the benefit of U.S. Provisional Patent Application No. 62/003,626, filed May 28, 2014. The contents of the foregoing are hereby incorporated herein by reference in their entireties.

FIELD OF THE INVENTION

Provided are certain compounds and/or pharmaceutically acceptable salts thereof which can inhibit kinase activity of CDK4/6 and may be useful for the treatment of hyper-proliferative diseases like cancer and inflammation.

BACKGROUND OF THE INVENTION

Hyper-proliferative diseases like cancer and inflammation are attracting the scientific community to provide therapeutic benefits. In this regard efforts have been made to identify and target specific mechanisms which play a role in proliferating the diseases.

Tumor development is closely associated with genetic alteration and deregulation of cyclin-dependent kinases (CDKs) and their regulators, suggesting that inhibitors of CDKs may be useful anti-cancer therapeutics.

CDKs are serine/threonine protein kinases, which are the driving force behind the cell cycle and cell proliferation. CDKs regulate initiation, progression, and completion of mammalian cell cycle, and they are critical for cell growth. Most of the known CDK's, including CDK1 through CDK9, are involved either directly or indirectly in cell cycle progression. Those directly involved with cell cycle progression, such as CDK1-4 and 6, can be classified as G1, S, or G2M phase enzymes. Uncontrolled proliferation is a hallmark of cancer cells and the alteration of CDK function occurs with high frequency in many solid tumors.

The pivotal roles of CDKs, and their associated proteins, in coordinating and driving the cell cycle in proliferating cells have been outlined. The development of monotherapies for the treatment of proliferative disorders, such as cancers, using therapeutics targeted generically at CDKs, or at specific CDKs, is therefore potentially highly desirable. CDK inhibitors could conceivably also be used to treat other conditions such as viral infections, autoimmune diseases and neuro-degenerative diseases, amongst others. CDKs targeted therapeutics may also provide clinical benefits in the treatment of the previously described diseases when used in combination therapy with either existing, or new, therapeutic agents.

Therefore, a compound having an inhibitory activity on CDK will be useful for the prevention or treatment of cancer. Although CDK4/6 inhibitors were disclosed in the arts, e.g., WO2010020675 and WO2012064805, many suffer from having short half-life or toxicity. Therefore, there is a need for new CDK4/6 inhibitors that have at least one advantageous property selected from potency, stability, selectivity, toxicity and pharmacodynamics properties as an alternative for the treatment of hyper-proliferative diseases. In this regard, a novel class of CDK4/6 inhibitors is provided herein.

DISCLOSURE OF THE INVENTION

Disclosed herein are certain novel 6-5 membered fused ring derivatives and pharmaceutical compositions thereof, and their use as pharmaceuticals.

In one aspect, disclosed herein is at least one compound of formula (I):

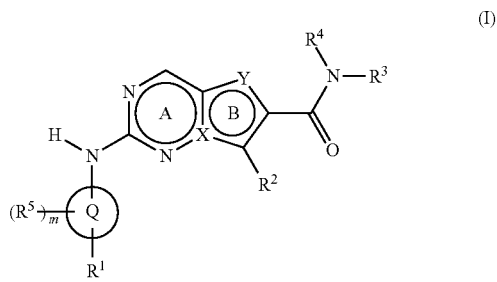

and/or at least one pharmaceutically acceptable salt thereof, wherein:

X is C or N;
Y is $CR^{11}$, O, S, or $NR^{12}$;
6-5 membered fused ring system A-B is selected from:

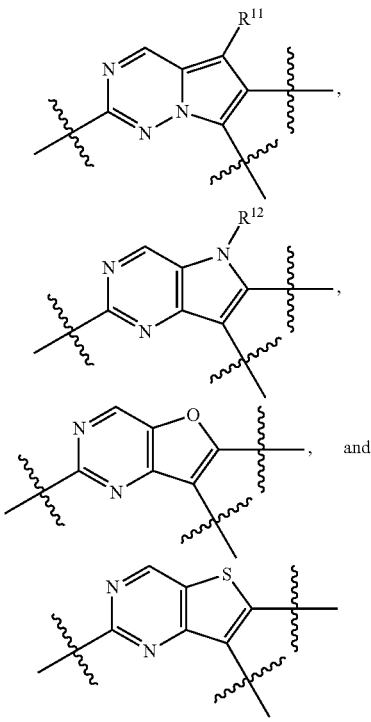

Q is selected from aryl and heteroaryl;
$R^1$ is selected from: hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$alkyl, wherein alkyl, alkenyl, alkynyl, cycloalkyl, and heterocyclyl are each unsubstituted or substituted with at least one substituent, such as one, two, three, or four substituents, independently selected from $R^{6a}$, and wherein aryl and heteroaryl are each unsubstituted or substituted with at least one substituent, such as one, two, three, or four substituents, independently selected from $R^{6b}$;
$R^2$ is selected from: hydrogen, halogen, hydroxyl, CN, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{14}$ alkyl, heteroaryl, and heteroaryl-$C_{1-4}$ alkyl, wherein alkyl, alkenyl, alkynyl, cycloalkyl, and heterocyclyl are each unsubstituted or substituted with at least one substituent, such as one, two, three, or four substituents, independently selected from $R^{6a}$, and each aryl and heteroaryl is unsubstituted or substituted with at least one substituent, such as one, two, three, or four substituents, independently selected from $R^{6b}$;

$R^3$ and $R^4$ are independently selected from: hydrogen, $C_{1-10}$ alkyl, $C_{2-10}$ alkenyl, $C_{2-10}$ alkynyl, and $C_{3-10}$ cycloalkyl; wherein alkyl, alkenyl, alkynyl, and cycloalkyl are each unsubstituted or substituted with at least one substituent, such as one, two, three, or four substituents, independently selected from $R^{6a}$; or $R^3$ and $R^4$ together with the nitrogen atoms to which they are attached form a 4-12 membered ring containing, 1, 2 or 3 heteroatoms independently selected from oxygen, sulfur and nitrogen, and optionally substituted with 1 or 2 $R^{6a}$ groups;

with the proviso that when $R^3$ and $R^4$ are both hydrogen, $R^2$ is not aryl or heteroaryl;

each $R^5$ is independently selected from: hydrogen, $C_{1-10}$ alkyl, $C_{2-10}$ alkenyl, $C_{2-10}$ alkynyl, $C_{3-10}$ cycloalkyl, $-OR^8$, $-NR^7S(O)_rR^8$, $-NO_2$, halogen, $-S(O)_rR^7$, $-SR^8$, $-S(O)_2OR^7$, $-OS(O)_2R^7$, $-S(O)_rNR^7R^8$, $-NR^7R^8$, $-O(CR^9R^{10})_rNR^7R^8$, $-C(O)R^7$, $-CO_2R^8$, $-CO_2(CR^9R^{10})_rCONR^7R^8$, $-OC(O)R^7$, $-CN$, $-C(O)NR^7R^8$, $-NR^7C(O)R^8$, $-OC(O)NR^7R^8$, $-NR^7C(O)OR^8$, $-NR^7C(O)NR^7R^8$, $-CR^7(N-OR^8)$, $-CHF_2$, $-CF_3$, $-OCHF_2$, and $-OCF_3$; wherein $C_{1-10}$ alkyl, $C_{2-10}$ alkenyl, $C_{2-10}$ alkynyl, and $C_{3-10}$ cycloalkyl are each unsubstituted or substituted with at least one substituent, such as one, two, three, or four substituents, independently selected from $R^{6a}$;

each $R^{6a}$ is independently selected from: $-C_{1-10}$ alkyl, $-C_{2-10}$ alkenyl, $-C_{2-10}$ alkynyl, $-C_{3-10}$ cycloalkyl, $-OR^8$, $-NR^7S(O)_rR^8$, $-NO_2$, -halogen, $-S(O)_rR^7$, $-SR^8$, $-S(O)_2OR^7$, $-OS(O)_2R^7$, $-S(O)_rNR^7R^8$, $-NR^7R^8$, $-(CR^9R^{10})_rOR^8$, $-(CR^9R^{10})_rNR^7R^8$, $-(CR^9R^{10})_rSR^8$, $-(CR^9R^{10})_rS(O)_rR^8$, $-(CR^9R^{10})_rCO_2R^8$, $-(CR^9R^{10})_rCONR^7R^8$, $-(CR^9R^{10})_rNR^7CO_2R^8$, $-(CR^9R^{10})_rOCONR^7R^8$, $-(CR^9R^{10})_rNR^7CONR^7R^8$, $-(CR^9R^{10})_rNR^7SO_2NR^7R^8$, $-O(CR^9R^{10})_rNR^7R^8$, $-C(O)R^7$, $-C(O)(CR^9R^{10})_rOR^8$, $-C(O)(CR^9R^{10})_rNR^7R^8$, $-C(O)(CR^9R^{10})_rSR^8$, $-C(O)(CR^9R^{10})_rS(O)_rR^8$, $-CO_2R^8$, $-CO_2(CR^9R^{10})_rCONR^7R^8$, $-OC(O)R^7$, $-CN$, $-C(O)NR^7R^8$, $-NR^7C(O)R^8$, $-OC(O)NR^7R^8$, $-NR^7C(O)OR^8$, $-NR^7C(O)NR^7R^8$, $-CR^7(N-OR^8)$, $-CHF_2$, $-CF_3$, $-OCHF_2$, and $-OCF_3$;

each $R^{6b}$ is independently selected from: $R^{6a}$, aryl, aryl-$C_{1-4}$ alkyl, heteroaryl, and heteroaryl-$C_{1-4}$ alkyl;

each $R^7$ and each $R^8$ are independently selected from: hydrogen, $C_{1-10}$ alkyl, $C_{2-10}$ alkenyl, $C_{2-10}$ alkynyl, cycloalkyl, cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl; wherein alkyl, alkenyl, alkynyl, cycloalkyl, and heterocyclyl are each unsubstituted or substituted with at least one substituent, such as one, two, three, or four substituents, independently selected from $R^{6a}$, and aryl and heteroaryl are each unsubstituted or substituted with at least one substituent, such as one, two, three, or four substituents, independently selected from $R^{6b}$; or $R^7$ and $R^8$ together with the atom(s) to which they are attached form a heterocyclic ring of 4 to 12 members containing 0, 1, or 2 additional heteroatoms independently selected from oxygen, sulfur and nitrogen, and optionally substituted with 1 or 2 $R^{6b}$ groups;

each $R^9$ and each $R^{10}$ are independently selected from: hydrogen, $C_{1-10}$ alkyl, $C_{2-10}$ alkenyl, $C_{2-10}$ alkynyl, cycloalkyl, cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl; or $R^9$ and $R^{10}$ together with the carbon atom(s) to which they are attached form a ring of 3 to 7 members containing 0, 1, or 2 heteroatoms independently selected from oxygen, sulfur and nitrogen, and optionally substituted with 1 or 2 $R^{6a}$ groups;

$R^{11}$ is selected from: hydrogen, $C_{1-10}$ alkyl, $C_{3-10}$ cycloalkyl, $C_{3-10}$ cycloalkylalkyl, heterocyclyl, heterocyclylalkyl, aryl, aryl-$C_{1-4}$ alkyl, heteroaryl, heteroaryl-$C_{1-4}$ alkyl, $-OR^7$, $-NR^7S(O)_rR^8$, $-S(O)_rR^7$, $-SR^7$, $-S(O)_2OR^7$, $-OS(O)_2R^7$, $-S(O)_rNR^7R^8$, $-NR^7R^8$, $-O(CR^9R^{10})_r NR^7R^8$, $-C(O)R^7$, $-CO_2R^8$, $-CO_2(CR^9R^{10})_rCONR^7R^8$, $-OC(O)R^7$, $-CN$, $-C(O)NR^7R^8$, $-NR^7C(O)R^8$, $-OC(O)NR^7R^8$, $-NR^7C(O)OR^8$, $-NR^7C(O)NR^7R^8$, $-CHF_2$, $-CF_3$, $-OCHF_2$, and $-OCF_3$;

$R^{12}$ is selected from: hydrogen, $C_{1-10}$ alkyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, $-S(O)_rR^7$, $-C(O)R^7$, $-CO_2R^7$, $-CO_2(CR^9R^{10})_rCONR^7R^8$, and $-C(O)NR^7R^8$;

m is independently selected from 0, 1, 2, and 3;

each r is independently selected from 1 and 2;

each t is independently selected from 1, 2, and 3.

In yet another aspect, the present disclosure provides pharmaceutical compositions comprising at least one compound of formula (I) and/or at least one pharmaceutically acceptable salt thereof and a pharmaceutically acceptable excipient.

In yet another aspect, the disclosure provides methods for modulating CDK4/6, comprising administering to a system or a subject in need thereof, a therapeutically effective amount of at least one compound of formula (I) and/or at least one pharmaceutically acceptable salt thereof or pharmaceutical compositions thereof, thereby modulating said CDK4/6. The disclosure also provides methods to treat, ameliorate or prevent a condition which responds to inhibition of CDK4/6 comprising administering to a system or subject in need of such treatment an effective amount of at least one compound of formula (I) and/or at least one pharmaceutically acceptable salt thereof or pharmaceutical compositions thereof, and optionally in combination with a second therapeutic agent, thereby treating said condition. Alternatively, the present disclosure provides the use of at least one compound of formula (I) and/or at least one pharmaceutically acceptable salt thereof in the manufacture of a medicament for treating a condition mediated by CDK4/6. In particular embodiments, the compounds of the disclosure may be used alone or in combination with a second therapeutic agent to treat a condition mediated by CDK4/6, wherein said condition is an autoimmune disease, a transplantation disease, an infectious disease or a cell proliferative disorder.

Furthermore, the disclosure provides methods for treating a cell proliferative disorder, comprising administering to a system or subject in need of such treatment an effective amount of at least one compound of formula (I) and/or at least one pharmaceutically acceptable salt thereof or pharmaceutical compositions thereof, and optionally in combination with a second therapeutic agent, thereby treating said condition.

Alternatively, the present disclosure provides the use of at least one compound of formula (I) and/or at least one pharmaceutically acceptable salt thereof in the manufacture of a medicament for treating a cell-proliferative disorder. In particular examples, the compounds of the disclosure may be used alone or in combination with a chemotherapeutic agent to treat a cell proliferative disorder, including but not limited to, lymphoma, osteosarcoma, melanoma, or a tumor of breast, renal, prostate, colorectal, thyroid, ovarian, pancreatic, neuronal, lung, uterine or gastrointestinal tumor.

In the above methods for using the compounds of the disclosure, at least one compound of formula (I) and/or at least one pharmaceutically acceptable salt thereof may be administered to a system comprising cells or tissues, or to a mammalian subject such as a human or animal subject.

DETAILED DESCRIPTION OF THE INVENTION

As used herein the following definitions are applicable.

The term "alkyl" refers to both branched and straight-chain saturated aliphatic hydrocarbon groups having the specified number of carbon atoms. Unless otherwise specified, "alkyl" refers to $C_1$-$C_6$ alkyl. For example, $C_1$-$C_6$, as in "$C_{1-6}$ alkyl" is defined to include groups having 1, 2, 3, 4, 5, or 6 carbons in a linear or branched arrangement. For example, "$C_{1-8}$ alkyl" includes but is not limited to methyl, ethyl, n-propyl, i-propyl, n-butyl, t-butyl, i-butyl, pentyl, hexyl, heptyl, and octyl.

The term "cycloalkyl" means a saturated aliphatic cyclic hydrocarbon group having the specified number of carbon atoms. Unless otherwise specified, "cycloalkyl" refers to $C_{3-10}$ cycloalkyl. For example, "cycloalkyl" includes but is not limited to cyclopropyl, methyl-cyclopropyl, 2,2-dimethyl-cyclobutyl, cyclopentyl, 2-ethyl-cyclopentyl, cyclohexyl, and trans-4-methylcyclohexyl.

The term "alkenyl" refers to a non-aromatic hydrocarbon radical, straight, branched or cyclic, containing from 2 to 10 carbon atoms and at least one carbon to carbon double bond. In some embodiments, one carbon to carbon double bond is present, and up to four non-aromatic carbon-carbon double bonds may be present. Thus, "$C_{2-6}$ alkenyl" means an alkenyl radical having from 2 to 6 carbon atoms. Alkenyl groups include but are not limited to ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. In some embodiments, up to three carbon-carbon triple bonds may be present. Thus, "$C_{2-6}$ alkynyl" means an alkynyl radical having from 2 to 6 carbon atoms. Alkynyl groups include but are not limited to ethynyl, propynyl, butynyl, and 3-methylbutynyl. The straight, branched or cyclic portion of the alkynyl group may contain triple bonds and may be substituted if a substituted alkynyl group is indicated.

The term "aryl" encompasses: 5- and 6-membered carbocyclic aromatic rings, for example, benzene; bicyclic ring systems wherein at least one ring is carbocyclic and aromatic, for example, naphthalene, indane, and 1, 2, 3, 4-tetrahydroquinoline; and tricyclic ring systems wherein at least one ring is carbocyclic and aromatic, for example, fluorene. In cases where the aryl substituent is bicyclic or tricyclic and at least one ring is non-aromatic, it is understood that attachment is via the aromatic ring.

For example, aryl includes 5- and 6-membered carbocyclic aromatic rings fused to a 5- to 7-membered heterocyclic ring containing one or more heteroatoms selected from N, O, and S, provided that the point of attachment is at the carbocyclic aromatic ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings are fused with a heterocyclic aromatic ring, the resulting ring system is heteroaryl, not aryl, as defined herein.

The term "halogen" (or "halo") refers to fluorine, chlorine, bromine and iodine.

The term "heteroaryl" refers to 5- to 8-membered aromatic, monocyclic rings containing one or more, for example, from 1 to 4, or, in some embodiments, from 1 to 3, heteroatoms selected from N, O, and S, with the remaining ring atoms being carbon;

8- to 12-membered bicyclic rings containing one or more, for example, from 1 to 4, or, in some embodiments, from 1 to 3, heteroatoms selected from N, O, and S, with the remaining ring atoms being carbon and wherein at least one heteroatom is present in an aromatic ring; and 11- to 14-membered tricyclic rings containing one or more, for example, from 1 to 4, or in some embodiments, from 1 to 3, heteroatoms selected from N, O, and S, with the remaining ring atoms being carbon and wherein at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 1-pyrazolyl, 2,3-pyrazolyl, 2,4-imidazolinyl, isoxazolyl, oxazolyl, thiazolyl, thiadiazolyl, tetrazolyl, thienyl, benzothienyl, furyl, benzofuryl, benzoimidazolinyl, indolinyl, pyridizinyl, triazolyl, quinolinyl, pyrazolyl, and 5,6,7,8-tetrahydroisoquinoline.

Further heteroaryl groups include but are not limited to pyrrolyl, isothiazolyl, triazinyl, pyrazinyl, pyridazinyl, indolyl, benzotriazolyl, quinoxalinyl, and isoquinolinyl. As with the definition of heterocycle below, "heteroaryl" is also understood to include the N-oxide derivative of any nitrogen-containing heteroaryl.

Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above.

In cases where the heteroaryl substituent is bicyclic or tricyclic and at least one ring is non-aromatic or contains no heteroatoms, it is understood that attachment is via the aromatic ring or via the heteroatom containing ring, respectively.

The term "heterocycle" (and variations thereof such as "heterocyclic", or "heterocyclyl") broadly refers to a single aliphatic ring, usually with 3 to 12 ring atoms, containing at least 2 carbon atoms in addition to one or more, preferably one to three heteroatoms independently selected from oxygen, sulfur, and nitrogen, as well as combinations comprising at least one of the foregoing heteroatoms. Alternatively, a heterocycle as defined above may be multicyclic ring system (e.g. bicyclic) in which two or more rings may be fused or bridged or spiro together, wherein at least one such ring contains one or more heteroatoms independently selected from oxygen, sulfur, and nitrogen. "Heterocycle" also refers to 5- to 7-membered heterocyclic ring containing one or more heteroatoms selected from N, O, and S fused with 5- and 6-membered carbocyclic aromatic ring, provided that the point of attachment is at the heterocyclic ring. The rings may be saturated or have one or more double bonds (i.e. partially unsaturated). The heterocycle can be substituted by oxo. The point of the attachment may be carbon or heteroatom in the heterocyclic ring, provided that attachment results in the creation of a stable structure. When the heterocyclic ring has substituents, it is understood that the substituents may be attached to any atom in the ring, whether a heteroatom or a carbon atom, provided that a stable chemical structure results. Heterocycle does not overlap with heteroaryl.

Suitable heterocycles include, for example (as numbered from the linkage position assigned priority 1), 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl. 1,4-piperazinyl, and 2,3-pyridazinyl. Morpholinyl groups are also contemplated, including 2-morpholinyl and 3-morpholinyl (numbered wherein the oxygen is assigned priority 1). Substituted heterocycle also includes ring systems substituted with one or more oxo moieties, such as piperidinyl N-oxide, morpholinyl-N-oxide, 1-oxo-1-thiomorpholinyl and 1,1-dioxo-1-thiomorpholinyl. Bicyclic heterocycles include, for example:

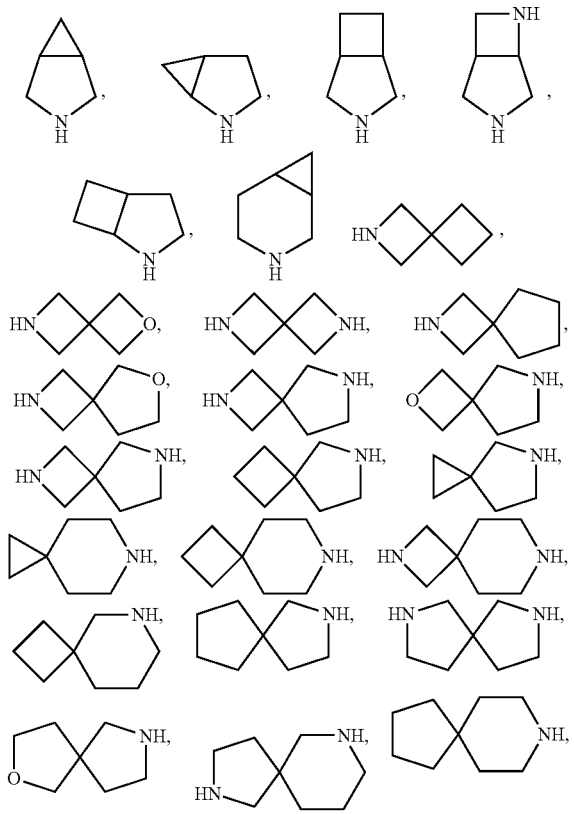

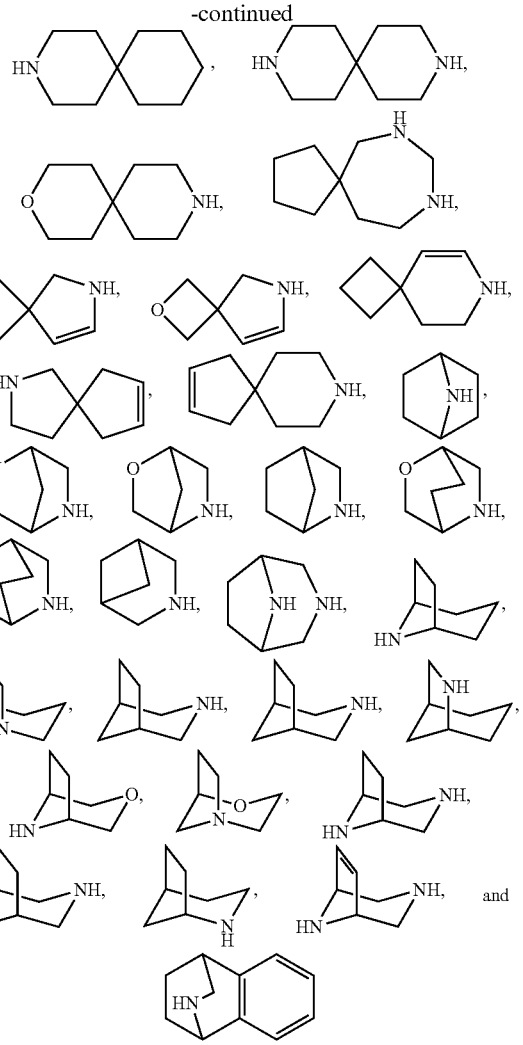

As used herein, "arylalkyl" refers to an alkyl moiety substituted by an aryl group. Example arylalkyl groups include benzyl, phenethyl, and naphthylmethyl groups. In some embodiments, arylalkyl groups have from 7 to 20 or 7 to 11 carbon atoms. When used in the phrase "arylC$_{1-4}$ alkyl", the term "C$_{1-4}$" refers to the alkyl portion of the moiety and does not describe the number of atoms in the aryl portion of the moiety. Likewise, when used in the phrase "arylC1-$_{10}$ alkyl", the term "C$_{1-10}$" refers to the alkyl portion of the moiety and does not describe the number of atoms in the aryl portion of the moiety.

As used herein, "heterocyclylalkyl" refers to alkyl substituted by heterocyclyl. When used in the phrase "heterocyclyl-C$_{1-6}$ alkyl", the term "C$_{1-6}$" refers to the alkyl portion of the moiety and does not describe the number of atoms in the heterocyclyl portion of the moiety.

As used herein, "cycloalkylalkyl" refers to alkyl substituted by cycloalkyl. When used in the phrase "C$_{3-10}$ cycloalkylalkyl", the term "C$_{3-10}$" refers to the cycloalkyl portion of the moiety and does not describe the number of atoms in the alkyl portion of the moiety. When used in the phrase "C$_{3-7}$ cycloalkylalkyl", the term "C$_{3-7}$" refers to the cycloalkyl portion of the moiety and does not describe the number of atoms in the alkyl portion of the moiety. When used in the phrase "C$_{3-8}$ cycloalkylalkyl", the term "C$_{3-8}$" refers to the cycloalkyl portion of the moiety and does not describe the number of atoms in the alkyl portion of the moiety. When used in the phrase "cycloalkyl $C_{1-10}$ alkyl", the term "$C_{1-10}$" refers to the alkyl portion of the moiety and does not describe the number of atoms in the cycloalkyl portion of the moiety.

As used herein, "heteroarylalkyl" refers to alkyl substituted by heteroaryl. When used in the phrase "heteroaryl $C_{1-4}$ alkyl", the term "$C_{1-4}$" refers to the alkyl portion of the moiety and does not describe the number of atoms in the heteroaryl portion of the moiety. Likewise, when used in the phrase "heteroaryl $C_{1-10}$ alkyl", the term "$C_{1-10}$" refers to the alkyl portion of the moiety and does not describe the number of atoms in the heteroaryl portion of the moiety.

For avoidance of doubt, reference, for example, to substitution of alkyl, cycloalkyl, heterocyclyl, aryl, and/or heteroaryl refers to substitution of each of those groups individually as well as to substitutions of combinations of those groups. That is, if $R^1$ is arylalkyl, the aryl portion may be unsubstituted or substituted with at least one substituent, such as one, two, three, or four substituents, independently selected from $R^{6b}$ and the alkyl portion may also be unsubstituted or substituted with at least one substituent, such as one, two, three, or four substituents, independently selected from $R^{6a}$.

The term "pharmaceutically acceptable salts" refers to salts prepared from pharmaceutically acceptable non-toxic bases or acids including inorganic or organic bases and inorganic or organic acids. Salts derived from inorganic bases may be selected, for example, from aluminum, ammonium, calcium, copper, ferric, ferrous, lithium, magnesium, manganic, manganous, potassium, sodium, and zinc salts. Further, for example, the pharmaceutically acceptable salts derived from inorganic bases may be selected from ammonium, calcium, magnesium, potassium, and sodium salts. Salts in the solid form may exist in one or more crystal structures, and may also be in the form of hydrates. Salts derived from pharmaceutically acceptable organic non-toxic bases may be selected, for example, from salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, and tripropylamine, tromethamine.

When the compound disclosed herein is basic, salts may be prepared using at least one pharmaceutically acceptable non-toxic acid, selected from inorganic and organic acids. Such acid may be selected, for example, from acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, and p-toluenesulfonic acids. In some embodiments, such acid may be selected, for example, from citric, hydrobromic, hydrochloric, maleic, phosphoric, sulfuric, fumaric, and tartaric acids.

The term "protecting group" or "Pg" refers to a substituent that can be commonly employed to block or protect a certain functionality while reacting other functional groups on the compound. For example, an "amino-protecting group" is a substituent attached to an amino group that blocks or protects the amino functionality in the compound. Suitable amino-protecting groups include but are not limited to acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include but are not limited to acetyl and silyl. A "carboxy-protecting group" refers to a substituent of the carboxy group that blocks or protects the carboxy functionality. Common carboxy-protecting groups include —CH2CH2SO2Ph, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The terms "administration of" and or "administering" at least one compound and/or at least one pharmaceutically acceptable salt should be understood to mean providing at least one compound and/or at least one pharmaceutically acceptable salt thereof to the individual in recognized need of treatment.

The term "effective amount" means the amount of the at least one compound and/or at least one pharmaceutically acceptable salt that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to a pharmaceutical composition is intended to encompass a product comprising the active ingredient (s), and the inert ingredient (s) that make up the carrier, as well as any product which results, directly or indirectly, from combination, complexation or aggregation of any two or more of the ingredients, or from dissociation of one or more of the ingredients, or from other types of reactions or interactions of one or more of the ingredients.

The term "pharmaceutically acceptable" it is meant compatible with the other ingredients of the formulation and not unacceptably deleterious to the recipient thereof.

Disclosed herein is at least one compound of formula (I):

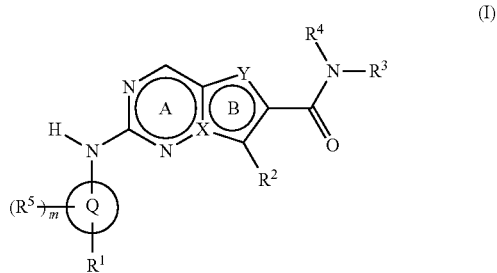

and/or at least one pharmaceutically acceptable salt thereof, wherein:

X is C or N;

Y is $CR^{11}$, O, S, or $NR^{12}$;

6-5 membered fused ring system A-B is selected from:

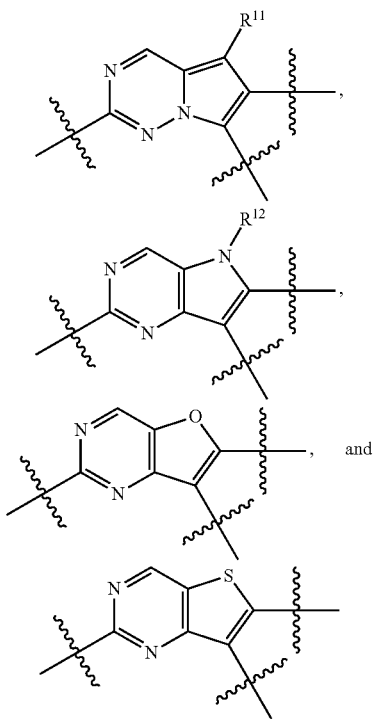

Q is selected from aryl and heteroaryl;

$R^1$ is selected from: hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, and heterocyclyl are each unsubstituted or substituted with at least one substituent, such as one, two, three, or four substituents, independently selected from $R^{6a}$, and wherein aryl and heteroaryl are each unsubstituted or substituted with at least one substituent, such as one, two, three, or four substituents, independently selected from $R^{6b}$;

$R^2$ is selected from: hydrogen, halogen, hydroxyl, CN, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, and heterocyclyl are each unsubstituted or substituted with at least one substituent, such as one, two, three, or four substituents, independently selected from $R^{6a}$, and each aryl and heteroaryl is unsubstituted or substituted with at least one substituent, such as one, two, three, or four substituents, independently selected from $R^{6b}$;

$R^3$ and $R^4$ are independently selected from: hydrogen, $C_{1-10}$ alkyl, $C_{2-10}$ alkenyl, $C_{2-10}$ alkynyl, and $C_{3-10}$ cycloalkyl; wherein alkyl, alkenyl, alkynyl, and cycloalkyl are each unsubstituted or substituted with at least one substituent, such as one, two, three, or four substituents, independently selected from $R^{6a}$; or $R^3$ and $R^4$ together with the nitrogen atoms to which they are attached form a 4-12 membered ring containing 0, 1, 2 or 3 heteroatoms independently selected from oxygen, sulfur and nitrogen, and optionally substituted with 1 or 2 $R^{6a}$ groups;

with the proviso that when $R^3$ and $R^4$ are both hydrogen, $R^2$ is not aryl or heteroaryl;

each $R^5$ is independently selected from: hydrogen, $C_{1-10}$ alkyl, $C_{2-10}$ alkenyl, $C_{2-10}$ alkynyl, $C_{3-10}$ cycloalkyl, —$OR^8$, —$NR^7S(O)_rR^8$, —$NO_2$, -halogen, —$S(O)_rR^7$, —$SR^8$, —$S(O)_2OR^7$, —$OS(O)_2R^8$, —$S(O)_rNR^7R^8$, —$NR^7R^8$, —$O(CR^9R^{10})_tNR^7R^8$, —$C(O)R^7$, —$CO_2R^8$, —$CO_2(CR^9R^{10})_tCONR^7R^8$, —$OC(O)R^7$, —CN, —$C(O)NR^7R^8$, —$NR^7C(O)R^8$, —$OC(O)NR^7R^8$, —$NR^7C(O)OR^8$, —$NR^7C(O)NR^7R^8$, —$CR^7(N$—$OR^8)$, —$CHF_2$, —$CF_3$, —$OCHF_2$, and —$OCF_3$; wherein $C_{1-10}$ alkyl, $C_{2-10}$ alkenyl, $C_{2-10}$ alkynyl, and $C_{3-10}$ cycloalkyl are each unsubstituted or substituted with at least one substituent, such as one, two, three, or four substituents, independently selected from $R^{6a}$;

each $R^{6a}$ is independently selected from: —$C_{1-10}$ alkyl, —$C_{2-10}$ alkenyl, —$C_{2-10}$ alkynyl, —$C_{3-10}$ cycloalkyl, —$OR^8$, —$NR^7S(O)_rR^8$, —$NO_2$, -halogen, —$S(O)_rR^7$, —$SR^8$, —$S(O)_2OR^7$, —$OS(O)_2R^8$, —$S(O)_rNR^7R^8$, —$NR^7R^8$, —$(CR^9R^{10})_tOR^{8'}$, —$(CR^9R^{10})_tNR^7R^8$, —$(CR^9R^{10})_tSR^8$, —$(CR^9R^{10})_tS(O)_rR^8$, —$(CR^9R^{10})_tCO_2R^8$, —$(CR^9R^{10})_tCONR^7R^8$, —$(CR^9R^{10})_tNR^7CO_2R^8$, —$(CR^9R^{10})_tOCONR^7R^8$, —$(CR^9R^{10})_tNR^7CONR^7R^8$, —$(CR^9R^{10})_tNR^7SO_2NR^7R^8$, —$O(CR^9R^{10})_tNR^7R^8$, —$C(O)R^7$, —$C(O)(CR^9R^{10})_tOR^8$, —$C(O)(CR^9R^{10})_tNR^7R^8$, —$C(O)(CR^9R^{10})_tSR^8$, —$C(O)(CR^9R^{10})_tS(O)_rR^8$, —$CO_2R^8$, —$CO_2(CR^9R^{10})_tCONR^7R^8$, —$OC(O)R^7$, —CN, —$C(O)NR^7R^8$, —$NR^7C(O)R^8$, —$OC(O)NR^7R^8$, —$NR^7C(O)OR^8$, —$NR^7C(O)NR^7R^8$, —$CR^7(N$—$OR^8)$, —$CHF_2$, —$CF_3$, —$OCHF_2$, and —$OCF_3$;

each $R^{6b}$ is independently selected from: $R^{6a}$, aryl, aryl-$C_{1-4}$ alkyl, heteroaryl, and heteroaryl-$C_{1-4}$ alkyl;

each $R^7$ and each $R^8$ are independently selected from: hydrogen, $C_{1-10}$ alkyl, $C_{2-10}$ alkenyl, $C_{2-10}$ alkynyl, cycloalkyl, cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl; wherein alkyl, alkenyl, alkynyl, cycloalkyl, and heterocyclyl are each unsubstituted or substituted with at least one substituent, such as one, two, three, or four substituents, independently selected from $R^{6a}$, and aryl and heteroaryl are each unsubstituted or substituted with at least one substituent, such as one, two, three, or four substituents, independently selected from $R^{6b}$; or $R^7$ and $R^8$ together with the atom(s) to which they are attached form a heterocyclic ring of 4 to 12 members containing 0, 1, or 2 additional heteroatoms independently selected from oxygen, sulfur and nitrogen, and optionally substituted with 1 or 2 $R^{6b}$ groups;

each $R^9$ and each $R^{10}$ are independently selected from: hydrogen, $C_{1-10}$ alkyl, $C_{2-10}$ alkenyl, $C_{2-10}$ alkynyl, cycloalkyl, cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl; or $R^9$ and $R^{10}$ together with the carbon atom(s) to which they are attached form a ring of 3 to 7 members containing 0, 1, or 2 heteroatoms independently selected from oxygen, sulfur and nitrogen, and optionally substituted with 1 or 2 $R^{6a}$ groups;

$R^{11}$ is selected from: hydrogen, $C_{1-10}$ alkyl, $C_{3-10}$ cycloalkyl, $C_{3-10}$ cycloalkylalkyl, heterocyclyl, heterocyclylalkyl, aryl, aryl-$C_{1-4}$ alkyl, heteroaryl, heteroaryl-$C_{1-4}$ alkyl, —$OR^7$, —$NR^7S(O)_rR^8$, —$S(O)_rR^7$, —$SR^7$, —$S(O)_2OR^7$, —$OS(O)_2R^7$, —$S(O)_rNR^7R^8$, —$NR^7R^8$, —$O(CR^9R^{10})_tNR^7R^8$, —$C(O)R^7$, —$CO_2R^8$, —$CO_2(CR^9R^{10})_tCONR^7R^8$, —$OC(O)R^7$, —CN, —$C(O)NR^7R^8$, —$NR^7C(O)R^8$, —$OC(O)NR^7R^8$, —$NR^7C(O)OR^8$, —$NR^7C(O)NR^7R^8$, —$CHF_2$, —$CF_3$, —$OCHF_2$, and —$OCF_3$;

$R^{12}$ is selected from: hydrogen, $C_{1-10}$ alkyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, —S(O)$_r$R$^7$, —C(O)R$^7$, —CO$_2$R$^7$, —CO$_2$(CR$^9$R$^{10}$)$_t$CONR$^7$R$^8$, and —C(O)NR$^7$R$^8$;

m is independently selected from 0, 1, 2, and 3;
each r is independently selected from 1 and 2;
each t is independently selected from 1, 2, and 3.

In some embodiments, 6-5 membered fused ring system A-B is

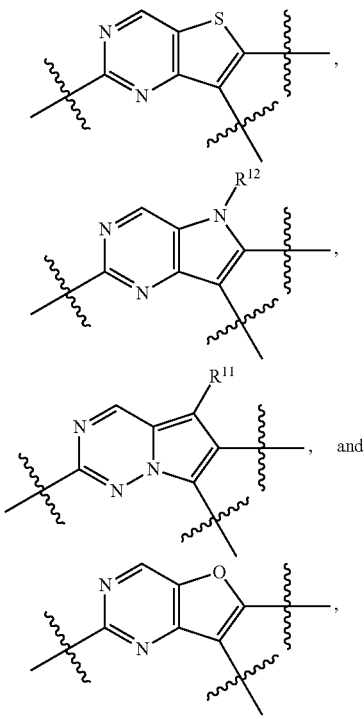

wherein each R$^{12}$ and each R$^{11}$ are independently selected from hydrogen and $C_{1-10}$ alkyl. Preferably each R$^{12}$ and each R$^{11}$ are independently selected from hydrogen and methyl.

In some embodiments, Q is selected from heteroaryl.

In some embodiments, Q is selected from pyridyl, pyridazinyl and 5,6,7,8-tetrahydro-1,6-naphthyridinyl. Preferably Q is selected from pyridin-2-yl, pyridazin-3-yl and 5,6,7,8-tetrahydro-1,6-naphthyridin-2-yl. More preferably Q is pyridin-2-yl.

In some embodiments, R$^1$ is selected from hydrogen, $C_{1-10}$ alkyl, heterocyclyl and heterocyclyl-$C_{1-4}$ alkyl, wherein heterocyclyl is unsubstituted or substituted with at least one, such as 1, 2, 3 or 4, substituents independently selected from R$^{6a}$, wherein each R$^{6a}$ is independently selected from $C_{1-10}$ alkyl, —NR$^7$R$^8$, —(CR$^9$R$^{10}$)$_t$OR$^8$, —OR$^8$, —C(O)R$^7$, —(CR$^9$R$^{10}$)$_t$S(O)$_r$R$^8$; wherein R$^7$, R$^8$, R$^9$, R$^{10}$, t and r are described as above.

In some embodiments, Q is selected from pyridin-2-yl, pyridazin-3-yl, R$^1$ is selected from heterocyclyl and heterocyclyl-$C_{1-4}$alkyl groups consisting of the following groups:

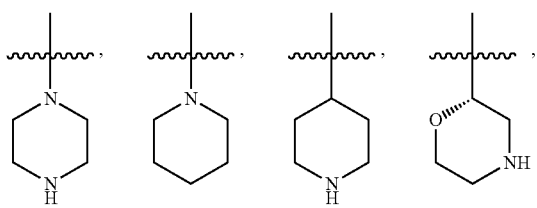

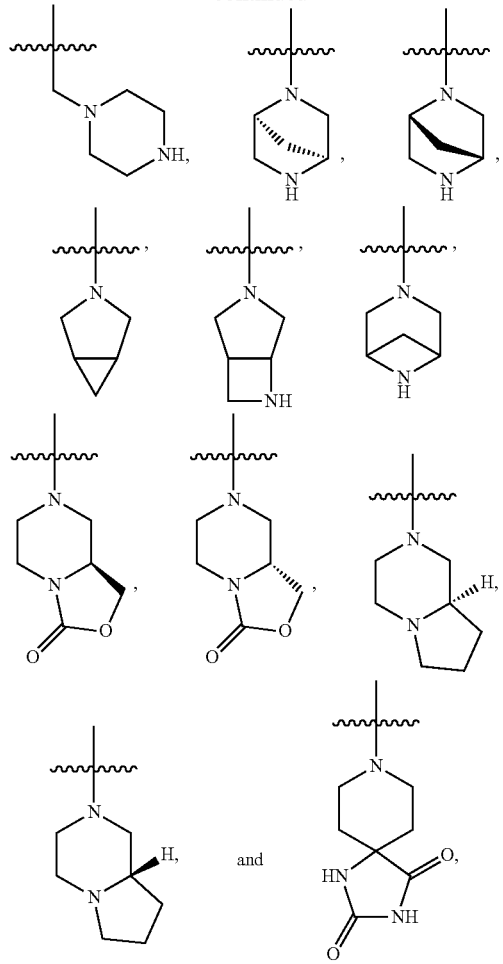

wherein each heterocyclyl is unsubstituted or substituted with at least one, such as 1, 2, 3 or 4 substituents independently selected from R$^{6a}$, wherein each R$^{6a}$ is independently selected from $C_{1-10}$ alkyl, —NR$^7$R$^8$, —(CR$^9$R$^{10}$)$_t$OR$^8$, —OR$^8$, —C(O)R$^7$, —C(O)NR$^7$R$^8$, —(CR$^9$R$^{10}$)$_t$S(O)$_r$R$^8$; wherein R$^7$, R$^8$, R$^9$, R$^{10}$, t and r are described as above.

Preferably, R$^{6a}$ is independently selected from hydrogen, methyl, ethyl, hydroxyl, hydroxymethyl, hydroxyethyl, acetyl, hydroxyacetyl, methoxymethyl, methoxyethyl, hydroxyacetyl, (methylsulfonyl)ethyl, amino, carbamoyl, methylamino, and dimethylamino.

In some embodiments, Q is selected from 5,6,7,8-tetrahydro-1,6-naphthyridinyl, R$^1$ is selected from hydrogen, $C_{1-10}$ alkyl.

In some embodiments, R$^2$ is selected from $C_{3-10}$ cycloalkyl, wherein cycloalkyl is unsubstituted or substituted with at least one, such as 1, 2, 3, or 4, substituents independently selected from R$^{6a}$.

In some embodiments, R$^2$ is selected from cyclopentyl and cyclohexyl, wherein cyclohexyl is unsubstituted or substituted with methyl. Preferably R$^2$ is selected from cyclopentyl and 4-methylcyclohexyl.

In some embodiments, R$^3$ and R$^4$ are independently selected from hydrogen, $C_{1-10}$ alkyl and $C_{3-10}$ cycloalkyl, with the proviso that when R$^3$ and R$^4$ are both hydrogen, R$^2$ is not aryl or heteroaryl. Preferably R$^3$ and R$^4$ are independently selected from hydrogen, methyl, ethyl, and cyclopropyl, with the proviso that when R$^3$ and R$^4$ are both hydrogen, R$^2$ is not aryl or heteroaryl.

In some embodiments, $R^3$ and $R^4$ together with the nitrogen atoms to which they are attached form azetidinyl, pyrrolidinyl, piperidinyl, piperazinyl, and morpholino, wherein the formed ring is unsubstituted or substituted with methyl, hydroxyl, and methoxy.

In some embodiments, $R^5$ is independently selected from hydrogen, $C_{1-10}$ alkyl and —C(O)$R^7$. wherein $R^7$ is selected from methyl and hydroxymethyl.

In some embodiments, Q is selected from pyridin-2-yl, pyridazin-3-yl, $R^5$ is hydrogen.

In some embodiments, Q is selected from 5,6,7,8-tetrahydro-1,6-naphthyridinyl, $R^5$ is independently selected from hydrogen, $C_{1-10}$ alkyl and —C(O)$R^7$. wherein $R^7$ is selected from methyl and hydroxymethyl.

Also provided is at least one compound, selected from:
7-cyclopentyl-N,N-dimethyl-2-(5-(piperazin-1-yl)pyridin-2-ylamino)thieno[3,2-d]pyrimidine-6-carboxamide,
7-cyclopentyl-N,N-dimethyl-2-(5-(4-methylpiperazin-1-yl)pyridin-2-ylamino)thieno[3,2-d]pyrimidine-6-carboxamide,
7-cyclopentyl-N,N-dimethyl-2-(5-(piperazin-1-yl)pyridin-2-ylamino)-5H-pyrrolo[3,2-d]pyrimidine-6-carboxamide,
7-cyclopentyl-N,N-dimethyl-2-(5-(4-methylpiperazin-1-yl)pyridin-2-ylamino)-5H-pyrrolo[3,2-d]pyrimidine-6-carboxamide,
7-cyclopentyl-N,N-dimethyl-2-((5-(piperazin-1-yl)pyridin-2-yl)amino)pyrrolo[2,1-f][1,2,4]triazine-6-carboxamide,
7-cyclopentyl-N,N-dimethyl-2-((5-(4-methylpiperazin-1-yl)pyridin-2-yl)amino)pyrrolo[2, 1-f][1,2,4]triazine-6-carboxamide,
7-cyclopentyl-N,N-dimethyl-2-((5-(piperazin-1-yl)pyridin-2-yl)amino)furo[3,2-d]pyrimidine-6-carboxamide,
7-cyclopentyl-N,N-dimethyl-2-((5-(4-methylpiperazin-1-yl)pyridin-2-yl)amino)furo[3,2-d]pyrimidine-6-carboxamide,
7-cyclopentyl-N,N,5-trimethyl-2-(5-(piperazin-1-yl)pyridin-2-ylamino)-5H-pyrrolo[3,2-d]pyrimidine-6-carboxamide,
7-cyclopentyl-N,N,5-trimethyl-2-(5-(4-methylpiperazin-1-yl)pyridin-2-ylamino)-5H-pyrrolo[3,2-d]pyrimidine-6-carboxamide,
(S)-7-cyclopentyl-N,N-dimethyl-2-((5-(3-oxotetrahydro-3H-oxazolo[3,4-a]pyrazin-7(1H)-yl)pyridin-2-yl)amino)thieno[3,2-d]pyrimidine-6-carboxamide,
(R)-7-cyclopentyl-N,N-dimethyl-2-((5-(3-oxotetrahydro-3H-oxazolo[3,4-a]pyrazin-7(1H)-yl)pyridin-2-yl)amino)thieno[3,2-d]pyrimidine-6-carboxamide,
(R)-7-cyclopentyl-N,N-dimethyl-2-((5-(morpholin-2-yl)pyridin-2-yl)amino)thieno[3,2-d]pyrimidine-6-carboxamide,
2-((5-(4-aminopiperidin-1-yl)pyridin-2-yl)amino)-7-cyclopentyl-N,N-dimethylthieno[3,2-d]pyrimidine-6-carboxamide,
7-cyclopentyl-N,N-dimethyl-2-((5-(4-(methylamino)piperidin-1-yl)pyridin-2-yl)amino)thieno[3,2-d]pyrimidine-6-carboxamide,
7-cyclopentyl-2-((5-(4-(dimethylamino)piperidin-1-yl)pyridin-2-yl)amino)-N,N-dimethylthieno[3,2-d]pyrimidine-6-carboxamide,
(S)-7-cyclopentyl-2-((5-(3-(methoxymethyl)piperazin-1-yl)pyridin-2-yl)amino)-N,N-dimethylthieno[3,2-d]pyrimidine-6-carboxamide,
(S)-7-cyclopentyl-2-((5-(3-(methoxymethyl)-4-methylpiperazin-1-yl)pyridin-2-yl)amino)-N,N-dimethylthieno[3,2-d]pyrimidine-6-carboxamide,
(S)-7-cyclopentyl-2-((5-(4-ethyl-3-(methoxymethyl)piperazin-1-yl)pyridin-2-yl)amino)-N,N-dimethylthieno[3,2-d]pyrimidine-6-carboxamide,
(S)-7-cyclopentyl-2-((5-(3-(hydroxymethyl)piperazin-1-yl)pyridin-2-yl)amino)-N,N-dimethylthieno[3,2-d]pyrimidine-6-carboxamide,
(S)-7-cyclopentyl-2-((5-(3-(hydroxymethyl)-4-methylpiperazin-1-yl)pyridin-2-yl)amino)-N,N-dimethylthieno[3,2-d]pyrimidine-6-carboxamide,
(S)-7-cyclopentyl-2-((5-(4-ethyl-3-(hydroxymethyl)piperazin-1-yl)pyridin-2-yl)amino)-N,N-dimethylthieno[3,2-d]pyrimidine-6-carboxamide,
(R)-7-cyclopentyl-2-((5-(3-(methoxymethyl)piperazin-1-yl)pyridin-2-yl)amino)-N,N-dimethylthieno[3,2-d]pyrimidine-6-carboxamide,
(R)-7-cyclopentyl-2-((5-(3-(methoxymethyl)-4-methylpiperazin-1-yl)pyridin-2-yl)amino)-N,N-dimethylthieno[3,2-d]pyrimidine-6-carboxamide,
(R)-7-cyclopentyl-2-((5-(4-ethyl-3-(methoxymethyl)piperazin-1-yl)pyridin-2-yl)amino)-N,N-dimethylthieno[3,2-d]pyrimidine-6-carboxamide,
(R)-7-cyclopentyl-2-((5-(3-(hydroxymethyl)piperazin-1-yl)pyridin-2-yl)amino)-N,N-dimethylthieno[3,2-d]pyrimidine-6-carboxamide,
(R)-7-cyclopentyl-2-((5-(3-(hydroxymethyl)-4-methylpiperazin-1-yl)pyridin-2-yl)amino)-N,N-dimethylthieno[3,2-d]pyrimidine-6-carboxamide,
(R)-7-cyclopentyl-2-((5-(4-ethyl-3-(hydroxymethyl)piperazin-1-yl)pyridin-2-yl)amino)-N,N-dimethylthieno[3,2-d]pyrimidine-6-carboxamide,
7-cyclopentyl-N,N-dimethyl-2-((5-(piperidin-4-yl)pyridin-2-yl)amino)thieno[3,2-d]pyrimidine-6-carboxamide,
7-cyclopentyl-N,N-dimethyl-2-((5-(1-methylpiperidin-4-yl)pyridin-2-yl)amino)thieno[3,2-d]pyrimidine-6-carboxamide,
2-((5-(6-amino-3-azabicyclo[3.1.0]hexan-3-yl)pyridin-2-yl)amino)-7-cyclopentyl-N,N-dimethylthieno[3,2-d]pyrimidine-6-carboxamide,
7-cyclopentyl-N,N-dimethyl-2-((5-(piperazin-1-ylmethyl)pyridin-2-yl)amino)thieno[3,2-d]pyrimidine-6-carboxamide,
7-cyclopentyl-N,N-dimethyl-2-((5-((4-methylpiperazin-1-yl)methyl)pyridin-2-yl)amino)thieno[3,2-d]pyrimidine-6-carboxamide,
7-cyclopentyl-2-((5-((4-ethylpiperazin-1-yl)methyl)pyridin-2-yl)amino)-N,N-dimethylthieno[3,2-d]pyrimidine-6-carboxamide,
2-((5-((1S,4S)-2,5-diazabicyclo[2.2.1]heptan-2-yl)pyridin-2-yl)amino)-7-cyclopentyl-N,N-dimethylthieno[3,2-d]pyrimidine-6-carboxamide,
7-cyclopentyl-N,N-dimethyl-2-((5-((1S,4S)-5-methyl-2,5-diazabicyclo[2.2.1]heptan-2-yl)pyridin-2-yl)amino)thieno[3,2-d]pyrimidine-6-carboxamide,
(R)-7-cyclopentyl-2-((5-(hexahydropyrrolo[1,2-a]pyrazin-2(1H)-yl)pyridin-2-yl)amino)-N,N-dimethylthieno[3,2-d]pyrimidine-6-carboxamide,
(S)-7-cyclopentyl-2-((5-(hexahydropyrrolo[1,2-a]pyrazin-2(1H)-yl)pyridin-2-yl)amino)-N,N-dimethylthieno[3,2-d]pyrimidine-6-carboxamide,
2-((5-((1R,4R)-2,5-diazabicyclo[2.2.1]heptan-2-yl)pyridin-2-yl)amino)-7-cyclopentyl-N,N-dimethylthieno[3,2-d]pyrimidine-6-carboxamide,
2-((5-(3,6-diazabicyclo[3.1.1]heptan-3-yl)pyridin-2-yl)amino)-7-cyclopentyl-N,N-dimethylthieno[3,2-d]pyrimidine-6-carboxamide, 7-cyclopentyl-N,N-dimethyl-2-((5-(6-methyl-3,6-diazabicyclo[3.1.1]heptan-3-yl)pyridin-2-yl)amino)thieno[3,2-d]pyrimidine-6-carboxamide, 7-cyclopentyl-2-((5-(6-ethyl-3,6-diazabicyclo[3.1.1]heptan-3-yl)pyridin-2-yl)amino)-N,N-dimethylthieno[3,2-d]pyrimidine-6-carboxamide, 7-cyclopentyl-2-((5-((7R,8aR)-7-hydroxyhexahydropyrrolo[1,2-a]pyrazin-2(1H)-yl)pyridin-2-yl)amino)-N,N-dimethylthieno[3,2-d]pyrimidine-6-carboxamide, 7-cyclopentyl-2-((5-((7S,8aR)-7-hydroxyhexahydropyrrolo[1,2-a]pyrazin-2(1H)-yl)pyridin-2-yl)amino)-N,N-dimethylthieno[3,2-d]pyrimidine-6-carboxamide, 7-cyclopentyl-2-((5-((7R,8aS)-7-hydroxyhexahydropyrrolo[1,2-a]pyrazin-2(1H)-yl)pyridin-2-yl)amino)-N,N-dimethylthieno[3,2-d]pyrimidine-6-carboxamide, 2-((5-(3,6-diazabicyclo[3.2.0]heptan-3-yl)pyridin-2-yl)amino)-7-cyclopentyl-N,N-dimethylthieno[3,2-d]pyrimidine-6-carboxamide, 7-cyclopentyl-N,N-dimethyl-2-((5-(6-methyl-3,6-diazabicyclo[3.2.0]heptan-3-yl)pyridin-2-yl)amino)thieno[3,2-d]pyrimidine-6-carboxamide, 7-cyclopentyl-2-((5-(6-ethyl-3,6-diazabicyclo[3.2.0]heptan-3-yl)pyridin-2-yl)amino)-N,N-dimethylthieno[3,2-d]pyrimidine-6-carboxamide, 7-cyclopentyl-N,N-dimethyl-2-((6-(piperazin-1-yl)pyridazin-3-yl)amino)thieno[3,2-d]pyrimidine-6-carboxamide, 7-cyclopentyl-N,N-dimethyl-2-((6-(4-methylpiperazin-1-yl)pyridazin-3-yl)amino)thieno[3,2-d]pyrimidine-6-carboxamide, 2-((6-(4-acetylpiperazin-1-yl)pyridazin-3-yl)amino)-7-cyclopentyl-N,N-dimethylthieno[3,2-d]pyrimidine-6-carboxamide, 7-cyclopentyl-2-((6-(4-(2-hydroxyacetyl)piperazin-1-yl)pyridazin-3-yl)amino)-N,N-dimethylthieno[3,2-d]pyrimidine-6-carboxamide, 7-cyclopentyl-N,N-dimethyl-2-((6-(4-(2-(methyl sulfonyl)ethyl)piperazin-1-yl)pyridazin-3-yl)amino)thieno[3,2-d]pyrimidine-6-carboxamide, 7-cyclopentyl-N,N-dimethyl-2-((5,6,7,8-tetrahydro-1,6-naphthyridin-2-yl)amino)thieno[3,2-d]pyrimidine-6-carboxamide, 7-cyclopentyl-N,N-dimethyl-2-((6-methyl-5,6,7,8-tetrahydro-1,6-naphthyridin-2-yl)amino)thieno[3,2-d]pyrimidine-6-carboxamide, 7-cyclopentyl-2-((5-(4-(2-hydroxyethyl)piperazin-1-yl)pyridin-2-yl)amino)-N,N-dimethylthieno[3,2-d]pyrimidine-6-carboxamide, 7-cyclopentyl-2-((5-(4-(2-methoxyethyl)piperazin-1-yl)pyridin-2-yl)amino)-N,N-dimethylthieno[3,2-d]pyrimidine-6-carboxamide, 7-cyclopentyl-N,N-dimethyl-2-((5-(4-(2-(methyl sulfonyl)ethyl)piperazin-1-yl)pyridin-2-yl)amino)thieno[3,2-d]pyrimidine-6-carboxamide, 7-cyclopentyl-2-((5-(4-ethylpiperazin-1-yl)pyridin-2-yl)amino)-N,N-dimethylthieno[3,2-d]pyrimidine-6-carboxamide, 7-cyclopentyl-2-((5-((3S,5R)-3,5-dimethylpiperazin-1-yl)pyridin-2-yl)amino)-N,N-dimethylthieno[3,2-d]pyrimidine-6-carboxamide 7-cyclopentyl-N,N-dimethyl-2-((5-((3S,5R)-3,4,5-trimethylpiperazin-1-yl)pyridin-2-yl)amino)thieno[3,2-d]pyrimidine-6-carboxamide 7-cyclopentyl-2-((5-((3S,5R)-4-ethyl-3,5-dimethylpiperazin-1-yl)pyridin-2-yl)amino)-N,N-dimethylthieno[3,2-d]pyrimidine-6-carboxamide 7-cyclopentyl-N,N-dimethyl-2-((5-(1-methyl-2,4-dioxo-1,3,8-triazaspiro[4.5]decan-8-yl)pyridin-2-yl)amino)thieno[3,2-d]pyrimidine-6-carboxamide 2-((5-(4-carbamoyl-4-(methyl amino)piperidin-1-yl)pyridin-2-yl)amino)-7-cyclopentyl-N,N-dimethylthieno[3,2-d]pyrimidine-6-carboxamide azetidin-1-yl(7-cyclopentyl-2-((5-(piperazin-1-yl)pyridin-2-yl)amino)thieno[3,2-d]pyrimidin-6-yl)methanone, (7-cyclopentyl-2-((5-(piperazin-1-yl)pyridin-2-yl)amino)thieno[3,2-d]pyrimidin-6-yl)(3-methoxyazetidin-1-yl)methanone, (7-cyclopentyl-2-((5-(piperazin-1-yl)pyridin-2-yl)amino)thieno[3,2-d]pyrimidin-6-yl)(3-hydroxyazetidin-1-yl)methan one, (7-cyclopentyl-2-((5-(piperazin-1-yl)pyridin-2-yl)amino)thieno[3,2-d]pyrimidin-6-yl)(piperidin-1-yl)methanone, (7-cyclopentyl-2-((5-(piperazin-1-yl)pyridin-2-yl)amino)thieno[3,2-d]pyrimidin-6-yl)(4-methylpiperazin-1-yl)methanone, (7-cyclopentyl-2-((5-(piperazin-1-yl)pyridin-2-yl)amino)thieno[3,2-d]pyrimidin-6-yl)(piperazin-1-yl)methanone, 7-cyclopentyl-N-cyclopropyl-2-((5-(piperazin-1-yl)pyridin-2-yl)amino)thieno[3,2-d]p yrimidine-6-carboxamide, (7-cyclopentyl-2-((5-(piperazin-1-yl)pyridin-2-yl)amino)thieno[3,2-d]pyrimidin-6-yl)(pyrrolidin-1-yl)methanone, 7-cyclopentyl-2-((5-(piperazin-1-yl)pyridin-2-yl)amino)thieno[3,2-d]pyrimidine-6-carboxamide, 7-cyclopentyl-N-methyl-2-((5-(piperazin-1-yl)pyridin-2-yl)amino)thieno[3,2-d]pyrimidine-6-carboxamide, 7-cyclopentyl-N-ethyl-2-((5-(piperazin-1-yl)pyridin-2-yl)amino)thieno[3,2-d]pyrimidine-6-carboxamide, (7-cyclopentyl-2-((5-(piperazin-1-yl)pyridin-2-yl)amino)thieno[3,2-d]pyrimidin-6-yl)(morpholino)methanone, azetidin-1-yl(7-cyclopentyl-2-((5-(4-methylpiperazin-1-yl)pyridin-2-yl)amino)thieno[3,2-d]pyrimidin-6-yl)methanone, (7-cyclopentyl-2-((5-(4-methylpiperazin-1-yl)pyridin-2-yl)amino)thieno[3,2-d]pyrimidin-6-yl)(3-methoxyazetidin-1-yl)methanone, (7-cyclopentyl-2-((5-(4-methylpiperazin-1-yl)pyridin-2-yl)amino)thieno[3,2-d]pyrimidin-6-yl)(piperidin-1-yl)methanone, (7-cyclopentyl-2-((5-(4-methylpiperazin-1-yl)pyridin-2-yl)amino)thieno[3,2-d]pyrimidin-6-yl)(4-methylpiperazin-1-yl)methanone, 7-cyclopentyl-N-cyclopropyl-2-((5-(4-methylpiperazin-1-yl)pyridin-2-yl)amino)thieno[3,2-d]pyrimidine-6-carboxamide, (7-cyclopentyl-2-((5-(4-methylpiperazin-1-yl)pyridin-2-yl)amino)thieno[3,2-d]pyrimidin-6-yl)(pyrrolidin-1-yl)methanone, 7-cyclopentyl-N-methyl-2-((5-(4-methylpiperazin-1-yl)pyridin-2-yl)amino)thieno[3,2-d]pyrimidine-6-carboxamide, (7-cyclopentyl-2-((5-(4-methylpiperazin-1-yl)pyridin-2-yl)amino)thieno[3,2-d]pyrimidin-6-yl)(morpholino)methanone, N,N-dimethyl-7-((1r,4r)-4-methylcyclohexyl)-2-((5-(piperazin-1-yl)pyridin-2-yl)amino) thieno[3,2-d]pyrimidine-6-carboxamide, N,N-dimethyl-7-((1r,4r)-4-methylcyclohexyl)-2-((5-(4-methylpiperazin-1-yl)pyridin-2-yl)amino)thieno[3,2-d]pyrimidine-6-carboxamide, N,N-dimethyl-7-((1r,4r)-4-methylcyclohexyl)-2-((5,6,7,8-tetrahydro-1,6-naphthyridin-2-yl)amino)thieno[3,2-d]pyrimidine-6-carboxamide, N,N-dimethyl-2-((6-methyl-5,6,7,8-tetrahydro-1,6-naphthyridin-2-yl)amino)-7-((1r,4r)-4-methylcyclohexyl)thieno[3,2-d]pyrimidine-6-carboxamide, 2-((6-acetyl-5,6,7,8-tetrahydro-1,6-naphthyridin-2-yl)amino)-N,N-dimethyl-7-((1r,4r)-4-methylcyclohexyl)thieno[3,2-d]pyrimidine-6-carboxamide, 2-((6-(2-hydroxyacetyl)-5,6,7,8-tetrahydro-1,6-naphthyridin-2-yl)amino)-N,N-dimethyl-7-((1r,4r)-4-methylcyclohexyl)thieno[3,2-d]pyrimidine-6-carboxamide, N,N-dimethyl-7-((1r,4r)-4-methylcyclohexyl)-2-((6-(piperazin-1-yl)pyridazin-3-yl)amino)thieno[3,2-d]pyrimidine-6-carboxamide, N,N-dimethyl-7-((1r,4r)-4-methylcyclohexyl)-2-((6-(4-methylpiperazin-1-yl)pyridazin-3-yl)amino)thieno[3,2-d]pyrimidine-6-carboxamide, 2-((6-(4-acetylpiperazin-1-yl)pyridazin-3-yl)amino)-N,N-dimethyl-7-((1r,4r)-4-methylcyclohexyl)thieno[3,2-d]pyrimidine-6-carboxamide, 2-((6-(4-(2-hydroxyacetyl)piperazin-1-yl)pyridazin-3-yl)amino)-N,N-dimethyl-7-((1 r,4r)-4-methylcyclohexyl)thieno[3,2-d]pyrimidine-6-carboxamide, and pharmaceutically acceptable salts thereof.

In another of its aspects, there is provided a pharmaceutical composition comprising a compound according to any one of the above embodiments and variations, wherein the composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, and intrathecally.

In yet another of its aspects, there is provided a kit comprising a compound of any one of the above embodiments and variations; and instructions which comprise one or more forms of information selected from the group consisting of indicating a disease state for which the composition is to be administered, storage information for the composition, dosing information and instructions regarding how to administer the composition. In one particular variation, the kit comprises the compound in a multiple dose form.

In still another of its aspects, there is provided an article of manufacture comprising a compound of any one of the above embodiments and variations; and packaging materials. In one variation, the packaging material comprises a container for housing the compound. In one particular variation, the container comprises a label indicating one or more members of the group consisting of a disease state for which the compound is to be administered, storage information, dosing information and/or instructions regarding how to administer the compound. In another variation, the article of manufacture comprises the compound in a multiple dose form.

In a further of its aspects, there is provided a therapeutic method comprising administering a compound of any one of the above embodiments and variations to a subject.

In another of its aspects, there is provided a method of inhibiting a CDK4/6 kinase comprising contacting the CDK4/6 with a compound of any one of the above embodiments and variations.

In yet another of its aspects, there is provided a method of inhibiting a CDK4/6 comprising causing a compound of any one of the above embodiments and variations to be present in a subject in order to inhibit the CDK4/6 in vivo.

In a further of its aspects, there is provided a method of inhibiting CDK4/6 comprising administering a first compound to a subject that is converted in vivo to a second compound wherein the second compound inhibits the CDK4/6 in vivo, the second compound being a compound according to any one of the above embodiments and variations.

In another of its aspects, there is provided a method of treating a disease state for which a CDK4/6 possesses activity that contributes to the pathology and/or symptomology of the disease state, the method comprising causing a compound of any one of the above embodiments and variations to be present in a subject in a therapeutically effective amount for the disease state.

In a further of its aspects, there is provided a method of treating a disease state for which a CDK4/6 possesses activity that contributes to the pathology and/or symptomology of the disease state, the method comprising administering a first compound to a subject that is converted in vivo to a second compound wherein the second compound inhibits the CDK4/6 in vivo. It is noted that the compounds of the present invention may be the first or second compounds.

In one variation of each of the above methods the disease state is selected from the group consisting of cancerous hyperproliferative disorders (e.g., brain, lung, squamous cell, bladder, gastric, pancreatic, breast, head, neck, renal, kidney, ovarian, prostate, colorectal, epidermoid, esophageal, testicular, gynecological or thyroid cancer); non-cancerous hyperproliferative disorders (e.g., benign hyperplasia of the skin (e.g., psoriasis), restenosis, and benign prostatic hypertrophy (BPH)); pancreatitis; kidney disease; pain; preventing blastocyte implantation; treating diseases related to vasculogenesis or angiogenesis (e.g., tumor angiogenesis, acute and chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic; prostate, colon and epidermoid cancer); asthma; neutrophil chemotaxis (e.g., reperfusion injury in myocardial infarction and stroke and inflammatory arthritis); septic shock; T-cell mediated diseases where immune suppression would be of value (e.g., the prevention of organ transplant rejection, graft versus host disease, lupus erythematosus, multiple sclerosis, and rheumatoid arthritis); atherosclerosis; inhibition of keratinocyte responses to growth factor cocktails; chronic obstructive pulmonary disease (COPD) and other diseases.

In another of its aspects, there is provided a method of treating a disease state for which a mutation in the CDK4/6 gene contributes to the pathology and/or symptomology of the disease state including, for example, melanomas, lung cancer, colon cancer and other tumor types.

In still another of its aspects, the present invention relates to the use of a compound of any of the above embodiments and variations as a medicament. In yet another of its aspects, the present invention relates to the use of a compound according to any one of the above embodiments and variations in the manufacture of a medicament for inhibiting a CDK4/6.

In a further of its aspects, the present invention relates to the use of a compound according to any one of the above embodiments and variations in the manufacture of a medicament for treating a disease state for which a CDK4/6 possesses activity that contributes to the pathology and/or symptomology of the disease state.

Administration and Pharmaceutical Compositions

In general, compounds of the disclosure will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors known to those of ordinary skill in the art. For example, for the treatment of neoplastic diseases and immune system disorders, the required dosage will also vary depending on the mode of administration, the particular condition to be treated and the effect desired.

In general, satisfactory results are indicated to be obtained systemically at daily dosages of from about 0.001 to about 100 mg/kg per body weight, or particularly, from about 0.03 to 2.5 mg/kg per body weight. An indicated daily dosage in the larger mammal, e.g. humans, may be in the range from about 0.5 mg to about 2000 mg, or more particularly, from about 0.5 mg to about 1000 mg, conveniently administered, for example, in divided doses up to four times a day or in retard form. Suitable unit dosage forms for oral administration comprise from ca. 1 to 50 mg active ingredient.

Compounds of the disclosure may be administered as pharmaceutical compositions by any conventional route; for example, enterally, e.g., orally, e.g., in the form of tablets or capsules; parenterally, e.g., in the form of injectable solutions or suspensions; or topically, e.g., in the form of lotions, gels, ointments or creams, or in a nasal or suppository form.

Pharmaceutical compositions comprising a compound of the present disclosure in free form or in a pharmaceutically acceptable salt form in association with at least one pharmaceutically acceptable carrier or diluent may be manufactured in a conventional manner by mixing, granulating, coating, dissolving or lyophilizing processes. For example, pharmaceutical compositions comprising a compound of the disclosure in association with at least one pharmaceutical acceptable carrier or diluent may be manufactured in conventional manner by mixing with a pharmaceutically acceptable carrier or diluent. Unit dosage forms for oral administration contain, for example, from about 0.1 mg to about 500 mg of active substance.

In one embodiment, the pharmaceutical compositions are solutions of the active ingredient, including suspensions or dispersions, such as isotonic aqueous solutions. In the case of lyophilized compositions comprising the active ingredient alone or together with a carrier such as mannitol, dispersions or suspensions can be made up before use. The pharmaceutical compositions may be sterilized and/or contain adjuvants, such as preserving, stabilizing, wetting or emulsifying agents, solution promoters, salts for regulating the osmotic pressure and/or buffers. Suitable preservatives include but are not limited to antioxidants such as ascorbic acid, or microbicides, such as sorbic acid or benzoic acid. The solutions or suspensions may further comprise viscosity-increasing agents, including but not limited to, sodium carboxymethyl cellulose, carboxymethylcellulose, dextran, polyvinylpyrrolidone, gelatins, or solubilizers, e.g. Tween 80 (polyoxyethylene(20)sorbitan mono-oleate).

Suspensions in oil may comprise as the oil component the vegetable, synthetic, or semi-synthetic oils customary for injection purposes. Examples include liquid fatty acid esters that contain as the acid component a long-chained fatty acid having from 8 to 22 carbon atoms, or in some embodiments, from 12 to 22 carbon atoms. Suitable liquid fatty acid esters include but are not limited to lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid and linoleic acid, and if desired, may contain antioxidants, for example vitamin E, 3-carotene or 3,5-di-tert-butyl-hydroxytoluene. The alcohol component of these fatty acid esters may have six carbon atoms and may be monovalent or polyvalent, for example a mono-, di- or trivalent, alcohol. Suitable alcohol components include but are not limited to methanol, ethanol, propanol, butanol or pentanol or isomers thereof; glycol and glycerol.

Other suitable fatty acid esters include but are not limited ethyl-oleate, isopropyl myristate, isopropyl palmitate, LABRAFIL® M 2375, (polyoxyethylene glycerol), LABRAFIL® M 1944 CS (unsaturated polyglycolized glycerides prepared by alcoholysis of apricot kernel oil and comprising glycerides and polyethylene glycol ester), LABRASOL™ (saturated polyglycolized glycerides prepared by alcoholysis of TCM and comprising glycerides and polyethylene glycol ester; all available from GaKefosse, France), and/or MIGLYOL® 812 (triglyceride of saturated fatty acids of chain length C8 to C12 from Hüls AG, Germany), and vegetable oils such as cottonseed oil, almond oil, olive oil, castor oil, sesame oil, soybean oil, or groundnut oil.

Pharmaceutical compositions for oral administration may be obtained, for example, by combining the active ingredient with one or more solid carriers, and if desired, granulating a resulting mixture, and processing the mixture or granules by the inclusion of additional excipients, to form tablets or tablet cores.

Suitable carriers include but are not limited to fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, carboxymethyl starch, crosslinked polyvinylpyrrolidone, alginic acid or a salt thereof, such as sodium alginate. Additional excipients include flow conditioners and lubricants, for example silicic acid, talc, stearic acid or salts thereof, such as magnesium or calcium stearate, and/or polyethylene glycol, or derivatives thereof.

Tablet cores may be provided with suitable, optionally enteric, coatings through the use of, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or tablet coatings, for example for identification purposes or to indicate different doses of active ingredient.

Pharmaceutical compositions for oral administration may also include hard capsules comprising gelatin or soft-sealed capsules comprising gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient may be dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories comprising a combination of the active ingredient and a suppository base. Suitable suppository bases are, for example, natural or synthetic triglycerides, paraffin hydrocarbons, polyethylene glycols or higher alkanols.

Pharmaceutical compositions suitable for parenteral administration may comprise aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers. The active ingredient, optionally together with excipients, can also be in the form of a lyophilizate and can be made into a solution before parenteral administration by the addition of suitable solvents. Solutions such as are used, for example, for parenteral administration can also be employed as infusion solutions. The manufacture of injectable preparations is usually carried out under sterile conditions, as is the filling, for example, into ampoules or vials, and the sealing of the containers.

The compounds of the disclosure may be administered as the sole active ingredient, or together with other drugs useful against neoplastic diseases or useful in immunomodulating regimens. For example, the compounds of the disclosure may be used in accordance with the disclosure in combination with pharmaceutical compositions effective in various diseases as described above, e.g. with cyclophosphamide, 5-fluorouracil, fludarabine, gemcitabine, cisplatinum, carboplatin, vincristine, vinblastine, etoposide, irinotecan, paclitaxel, docetaxel, rituxan, doxorubicine, gefitinib, or imatinib; or also with cyclosporins, rapamycins, ascomycins or their immunosuppressive analogs, e.g. cyclosporin A, cyclosporin G, FK-506, sirolimus or everolimus, corticosteroids, e.g. prednisone, cyclophosphamide, azathioprene, methotrexate, gold salts, sulfasalazine, antimalarials, brequinar, leflunomide, mizoribine, mycophenolic acid, mycophenolate, mofetil, 15-deoxyspergualine, immuno-suppressive monoclonal antibodies, e.g. monoclonal antibodies to leukocyte receptors, e.g. MHC, CD2, CD3, CD4, CD7, CD25, CD28, I CD40, CD45, CD58, CD80, CD86, CD152, CD137, CD154, ICOS, LFA-1, VLA-4 or their ligands, or other immunomodulatory compounds, e.g. CTLA41g.

The disclosure also provides for a pharmaceutical combinations, e.g. a kit, comprising a) a first agent which is a compound of the disclosure as disclosed herein, in free form or in pharmaceutically acceptable salt form, and b) at least one co-agent. The kit can comprise instructions for its administration.

EXAMPLES

Various methods may be developed for synthesizing the at least one compound of formula (I) and/or at least one pharmaceutically acceptable salt thereof. Representative methods for synthesizing the at least one compound of formula (I) and/or at least one pharmaceutically acceptable salt thereof are provided in the Examples. It is noted, however, that the at least one compound of formula (I) and/or at least one pharmaceutically acceptable salt thereof may also be synthesized by other synthetic routes that others may devise.

It will be readily recognized that certain compounds of formula (I) have atoms with linkages to other atoms that confer a particular stereochemistry to the compound (e.g., chiral centers). It is recognized that synthesis of the at least one compound of formula (I) and/or at least one pharmaceutically acceptable salt thereof may result in the creation of mixtures of different stereoisomers (enantiomers, diastereomers). Unless a particular stereochemistry is specified, recitation of a compound is intended to encompass all of the different possible stereoisomers.

The at least one compound of formula (I) can also be prepared as a pharmaceutically acceptable acid addition salt by, for example, reacting the free base form of the at least one compound with a pharmaceutically acceptable inorganic or organic acid. Alternatively, a pharmaceutically acceptable base addition salt of the at least one compound of formula (I) can be prepared by, for example, reacting the free acid form of the at least one compound with a pharmaceutically acceptable inorganic or organic base. Inorganic and organic acids and bases suitable for the preparation of the pharmaceutically acceptable salts of compounds of formula (I) are set forth in the definitions section of this Application. Alternatively, the salt forms of the compounds of formula (I) can be prepared using salts of the starting materials or intermediates.

The free acid or free base forms of the compounds of formula (I) can be prepared from the corresponding base addition salt or acid addition salt form. For example, a compound of formula (I) in an acid addition salt form can be converted to the corresponding free base thereof by treating with a suitable base (e.g., ammonium hydroxide solution, sodium hydroxide, and the like). A compound of formula (I) in a base addition salt form can be converted to the corresponding free acid thereof by, for example, treating with a suitable acid (e.g., hydrochloric acid, etc).

The N-oxides of the at least one compound of formula (I) and/or at least one pharmaceutically acceptable salt thereof can be prepared by methods known to those of ordinary skill in the art. For example, N-oxides can be prepared by treating an unoxidized form of the compound of formula (I) with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0 to 80° C. Alternatively, the N-oxides of the compounds of formula (I) can be prepared from the N-oxide of an appropriate starting material.

Compounds of formula (I) in an unoxidized form can be prepared from N-oxides of compounds of formula (I) by, for example, treating with a reducing agent (e.g., sulfur, sulfur dioxide, triphenyl phosphine, lithium borohydride, sodium borohydride, phosphorus trichloride, tribromide, and the like) in an suitable inert organic solvent (e.g., acetonitrile, ethanol, aqueous dioxane, and the like) at 0 to 80° C.

Protected derivatives of the compounds of formula (I) can be made by methods known to those of ordinary skill in the art. A detailed description of the techniques applicable to the creation of protecting groups and their removal can be found in T. W. Greene, Protecting Groups in Organic Synthesis, 3rd edition, John Wiley & Sons, Inc. 1999.

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. For example, the following abbreviations may be used in the examples and throughout the specification: g (grams); mg (milligrams); L (liters); mL (milliliters); µL (microliters); psi (pounds per square inch); M (molar); mM (millimolar); i.v. (intravenous); Hz (Hertz); MHz (megahertz); mol (moles); mmol (millimoles); RT (room temperature); min (minutes); h (hours); mp (melting point); TLC (thin layer chromatography); Rt (retention time); RP (reverse phase); MeOH (methanol); i-PrOH (isopropanol); TEA (triethylamine); TFA (trifluoroacetic acid); TFAA (trifluoroacetic anhydride); THF (tetrahydrofuran); DMSO (dimethyl sulfoxide); EtOAc (ethyl acetate); DME (1,2-dimethoxyethane); DCM (dichloromethane); DCE (dichloroethane); DMF (N,N-dimethylformamide); DMPU (N,N'-dimethylpropyleneurea); CDI (1,1-carbonyldiimidazole); IBCF (isobutyl chloroformate); HOAc (acetic acid); HOSu (N-hydroxysuccinimide); HOBT (1-hydroxybenzotriazole); Et$_2$O (diethyl ether); EDCI (1-(3-dimethylaminopropyl)-3-ethylcarbodiimide hydrochloride); BOC (tert-butyloxycarbonyl); FMOC (9-fluorenylmethoxycarbonyl); DCC (dicyclohexylcarbodiimide); CBZ (benzyloxycarbonyl); Ac (acetyl); atm (atmosphere); TMSE (2-(trimethylsilyl)ethyl); TMS (trimethylsilyl); TIPS (triisopropylsilyl); TBS (t-butyldimethylsilyl); DMAP (4-dimethylaminopyridine); Me (methyl); OMe (methoxy); Et (ethyl); tBu (tert-butyl); HPLC (high pressure liquid chromatography); BOP (bis(2-oxo-3-oxazolidinyl)phosphinic chloride); TBAF (tetra-n-butylammonium fluoride); m-CPBA (meta-chloroperbenzoic acid).

References to ether or Et$_2$O are to diethyl ether; brine refers to a saturated aqueous solution of NaCl. Unless otherwise indicated, all temperatures are expressed in ° C. (degrees Centigrade). All reactions were conducted under an inert atmosphere at RT unless otherwise noted.

$^1$H NMR spectra were recorded on a Varian Mercury Plus 400. Chemical shifts are expressed in parts per million (ppm). Coupling constants are in units of hertz (Hz). Splitting patterns describe apparent multiplicities and are designated as s (singlet), d (doublet), t (triplet), q (quartet), m (multiplet), and br (broad).

Low-resolution mass spectra (MS) and compound purity data were acquired on a Shimadzu LC/MS single quadrapole system equipped with electrospray ionization (ESI) source, UV detector (220 and 254 nm), and evaporative light scattering detector (ELSD). Thin-layer chromatography was performed on 0.25 mm E. Merck silica gel plates (60F-254), visualized with UV light, 5% ethanolic phosphomolybdic acid, ninhydrin, or p-anisaldehyde solution. Flash column chromatography was performed on silica gel (230-400 mesh, Merck).

Synthetic Schemes

Synthetic methods for preparing the compounds of the present invention are illustrated in the following Schemes and Examples. Starting materials are commercially available or may be made according to procedures known in the art or as illustrated herein.

Example 1

7-Cyclopentyl-N,N-dimethyl-2-(5-(piperazin-1-yl)pyridin-2-ylamino)thieno[3,2-d]pyrimidine-6-carboxamide (1)

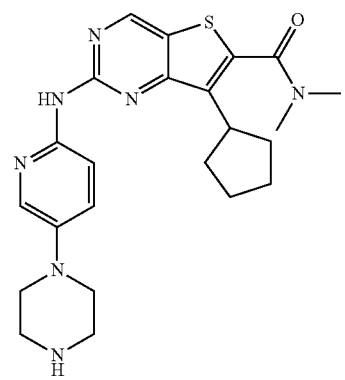

(5-Bromo-2-(methylthio)pyrimidin-4-yl)(cyclopentyl)methanol (1a)

A mixture of 5-bromo-2-(methylthio)pyrimidine-4-carboxylic acid (2.49 g, 10.0 mmol) and cyclopentanecarbaldehyde (4.23 g, 43.2 mmol) in anisole (40 mL) was heated at 140° C. for 7 h. Solvent was evaporated under reduced pressure. The residue was purified by silica gel column, eluted with 20-30% ethyl acetate in hexanes to give (5-bromo-2-(methylthio)pyrimidin-4-yl)(cyclopentyl)methanol (1a) as pale yellow liquid (1.22 g, 40%). MS-ESI (m/z): 303 and 305 (1:1, 100%), [M+1]$^+$.

(5-Bromo-2-(methylthio)pyrimidin-4-yl)(cyclopentyl)methanone (1b)

To a solution of 1a (1.15 g, 3.79 mmol) in anhydrous DCM (40 mL) at 0° C. was added a Dess-Martin periodinane (2.90 g, 6.83 mmol). The mixture was stirred at room temperature for 2 h. The reaction was diluted with saturated aqueous NaHCO$_3$ (100 mL), extracted with ethyl acetate (2×50 mL). The extracts were washed with brine and dried (MgSO$_4$). Solvents were evaporated under reduced pressure. The residue was purified by silica gel column, eluted with 10-20% ethyl acetate in hexanes to give (5-bromo-2-(methylthio)pyrimidin-4-yl)(cyclopentyl)methanone (1b) as pale yellow liquid (1.10 g, 96%). MS-ESI (m/z): 301 and 303 (1:1, 100%), [M+1]$^+$.

7-Cyclopentyl-2-(methylthio)thieno[3,2-d]pyrimidine-6-carboxylic acid (1c)

To a solution of 1b (73.6 mg, 0.244 mmol) and methyl thioglycolate (27.2 mg, 0.256 mmol) in DMF (1 mL) at room temperature was added NaH (60%, 19.5 mg, 0.488 mmol). The mixture was stirred at room temperature for 15 min. then heated at 60° C. for 3 h. After cooling to room temperature, 5 N NaOH (0.2 mL) was added and the mixture was stirred for 1 h. The reaction was diluted with water and 1 N HCl was added to pH=3~4. The mixture was extracted with ethyl acetate (2×5 mL). The extracts were washed with brine and dried (MgSO$_4$). Solvents were evaporated under reduced pressure to give crude 7-cyclopentyl-2-(methylthio)thieno[3,2-d]pyrimidine-6-carboxylic acid (1c) as white solid (72.0 mg, 100%). MS-ESI (m/z): 295 (100%), [M+1]$^+$. This was carried on to next reaction without further purification.

7-Cyclopentyl-N,N-dimethyl-2-(methylthio)thieno[3,2-d]pyrimidine-6-carboxamide (1d)

To a mixture of 1c (71.9 mg, 0.244 mmol), dimethylamine hydrochloride (39.8 mg, 0.488 mmol), EDCI (70.3 mg, 0.366 mmol) and HOBT hydrate (56.0 mg, 0.366 mmol) in anhydrous DMF (2 mL) was added DIPEA (1.27 mL, 0.732 mmol). The mixture was stirred at room temperature for 17 h. The mixture was diluted with water and extracted with ethyl acetate (2×). The extracts were washed with brine and dried (Na$_2$SO$_4$). Solvents were evaporated under reduced pressure. The residue was purified by silica gel column, eluted with 50% ethyl acetate in hexanes to give 7-cyclopentyl-N,N-dimethyl-2-(methylthio)thieno[3,2-d]pyrimidine-6-carboxamide (1d) as colorless oil (63.8 mg, 81%). MS-ESI (m/z): 322 (100%), [M+1]$^+$.

7-Cyclopentyl-N,N-dimethyl-2-(methylsulfonyl)thieno[3,2-d]pyrimidine-6-carboxamide (1e)

To a solution of 1d (63.0 mg, 0.196 mmol) in dichloromethane (4 mL) at 0° C. was added mCPBA (75%, 113 mg, 0.490 mmol). The mixture was stirred at room temperature for 1 h. Saturated aqueous NaHSO$_3$ (2 mL) was added and stirred for 10 min. The mixture was diluted with saturated aqueous NaHCO$_3$ (10 mL) and extracted with DCM (2×10 mL). The extracts were dried (Na$_2$SO$_4$). Solvents were evaporated under reduced pressure to give crude 7-cyclopentyl-N,N-dimethyl-2-(methyl sulfonyl)thieno[3,2-d]pyrimidine-6-carboxamide (1e) as white solid (69.3 mg, 100%). MS-ESI (m/z): 354 [M+1]$^+$.

tert-Butyl 4-(6-(7-cyclopentyl-6-(dimethylcarbamoyl)thieno[3,2-d]pyrimidin-2-ylamino)pyridin-3-yl)piperazine-1-carboxylate (1f)

To a solution of tert-butyl 4-(6-formamidopyridin-3-yl)piperazine-1-carboxylate (48.8 mg, 0.159 mmol) in DMF (0.5 mL) at room temperature was added NaH (60%, 10 mg, 0.25 mmol). The mixture was stirred at room temperature for 20 min. A solution of 1e (51.2 mg, 0.145 mmol) in DMF (0.5 mL) was added. The mixture was stirred at room temperature for 1 h. Methanol (3 mL) was added and stirred for 30 min. The mixture was diluted with water (10 mL) and extracted with ethyl acetate (2×10 mL). The extracts were dried (Na$_2$SO$_4$). Solvents were evaporated under reduced pressure to give crude tert-butyl 4-(6-(7-cyclopentyl-6-(dimethylcarbamoyl)thieno[3,2-d]pyrimidin-2-ylamino) pyridin-3-yl)piperazine-1-carboxylate (1f) as white solid (90 mg), which contains some inseparable impurities. MS-ESI (m/z): 552 [M+1]$^+$.

7-Cyclopentyl-N,N-dimethyl-2-(5-(piperazin-1-yl)pyridin-2-ylamino)thieno[3,2-d]pyrimidine-6-carboxamide (1)

To a solution of crude 1f (80 mg) in dichloromethane (3 mL) was added TFA (3 mL). The mixture was stirred at room temperature for 1 h. Solvents were evaporated under reduced pressure. The residue was purified by silica gel column, eluted with 94:5:1 DCM/methanol/ammonia to give 7-cyclopentyl-N,N-dimethyl-2-(5-(piperazin-1-yl)pyridin-2-ylamino)thieno[3,2-d]pyrimidine-6-carboxamide (1) as pale yellow solid (32.8 mg, 50%, 2 steps). MS-ESI (m/z): 452 [M+1]$^+$.

Example 2

7-Cyclopentyl-N,N-dimethyl-2-(5-(4-methylpiperazin-1-yl)pyridin-2-ylamino)thieno[3,2-d]pyrimidine-6-carboxamide (2)

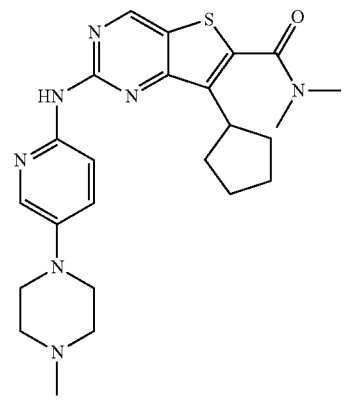

To a solution of 1 (15.3 mg, 0.034 mmol) in 1,2-dichloroethane (1 mL) at room temperature was added formaldehyde (37% in water, 14 mg, 0.17 mmol) followed by NaBH(OAc)$_3$ (9.3 mg, 0.044 mmol). The mixture was stirred at room temperature for 30 min. The mixture was diluted with saturated aqueous NaHCO$_3$ (50 mL) and extracted with DCM (2×5 mL). The extracts were dried (Na$_2$SO$_4$). Solvents were evaporated under reduced pressure. The residue was purified by silica gel column, eluted with 96:3:1 DCM/methanol/ammonia to give 7-cyclopentyl-N,N-dimethyl-2-(5-(4-methylpiperazin-1-yl)pyridin-2-ylamino)thieno[3,2-d]pyrimidine-6-carboxamide (2) as pale yellow solid (13.5 mg, 85%). MS-ESI (m/z): 466 [M+1]$^+$.

Example 3

7-Cyclopentyl-N,N-dimethyl-2-(5-(piperazin-1-yl)pyridin-2-ylamino)-5H-pyrrolo[3,2-d]pyrimidine-6-carboxamide (3)

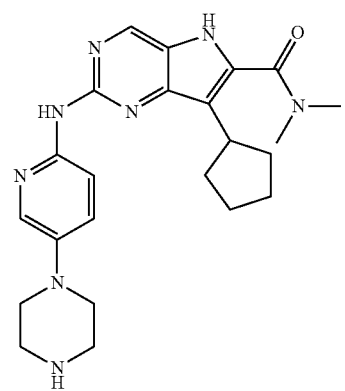

tert-Butyl 2-(4-(cyclopentanecarbonyl)-2-(methylthio)pyrimidin-5-ylamino) acetate (3a)

A mixture of (5-bromo-2-(methylthio)pyrimidin-4-yl)(cyclopentyl)methanone (1b, 752 mg, 2.50 mmol), glycine t-butyl ester hydrochloride (502 mg, 3.00 mmol), $Pd_2(dba)_3$ (229 mg, 0.25 mmol), xantphos (145 mg, 0.25 mmol) and $Cs_2CO_3$ (2.61 g, 8.00 mmol) in dioxane (25 mL) was heated under nitrogen at 90° C. for 16 h. The mixture was cooled to room temperature and diluted with water. This was extracted with ethyl acetate (2×), washed with brine and dried ($Na_2SO_4$). Solvent was evaporated under reduced pressure. The residue was purified by silica gel column, eluted with 20-30% ethyl acetate in hexanes to give tert-butyl 2-(4-(cyclopentanecarbonyl)-2-(methylthio)pyrimidin-5-ylamino)acetate (3a) as yellow solid (460 mg, 52%). MS-ESI (m/z): 352 [M+1]$^+$.

tert-Butyl 2-(N-(4-(cyclopentanecarbonyl)-2-(methylthio)pyrimidin-5-yl) acetamido)acetate (3b)

To a solution of 3a (272 mg, 0.775 mmol) in anhydrous DCM (8 mL) was added pyridine (135 mg, 1.71 mmol) and DMAP (4.7 mg, 0.04 mmol). Then acetyl chloride (183 mg, 2.33 mmol) was added dropwise. The mixture was stirred at room temperature for 16 h. The reaction was diluted with water (30 mL), extracted with DCM (2×15 mL). The extracts were washed with brine and dried ($MgSO_4$). Solvents were evaporated under reduced pressure. The residue was purified by silica gel column, eluted with 30-50% ethyl acetate in hexanes to give tert-butyl 2-(N-(4-(cyclopentanecarbonyl)-2-(methylthio)pyrimidin-5-yl)acetamido)acetate (3b) as pale yellow oil (298 mg, 98%). MS-ESI (m/z): 394 [M+1]$^+$.

tert-Butyl 5-acetyl-7-cyclopentyl-7-hydroxy-2-(methylthio)-6,7-dihydro-5H-pyrrolo[3,2-d]pyrimidine-6-carboxylate (3c)

To a solution of 3b (412 mg, 1.05 mmol) in DMF (8 mL) was added $K_2CO_3$ (362 mg, 2.62 mmol). The mixture was heated at 60° C. for 2 h. After cooling to room temperature, the reaction was diluted with water and extracted with ethyl acetate (2×20 mL). The extracts were washed with brine and dried ($MgSO_4$). Solvents were evaporated under reduced pressure to give crude tert-butyl 5-acetyl-7-cyclopentyl-7-hydroxy-2-(methylthio)-6,7-dihydro-5H-pyrrolo[3,2-d]pyrimidine-6-carboxylate (3c) as yellow oil (412 mg, 100%). MS-ESI (m/z): 394 [M+1]$^+$. This was carried on to next reaction without further purification.

5-Acetyl-7-cyclopentyl-7-hydroxy-2-(methylthio)-6,7-dihydro-5H-pyrrolo[3,2-d]pyrimidine-6-carboxylic acid (3d)

To a solution of 3c (412 mg, 1.05 mmol) in DCM (2 mL) was added TFA (5 mL). The mixture was stirred at room temperature for 2 h. Solvents were evaporated under reduced pressure to give 5-acetyl-7-cyclopentyl-7-hydroxy-2-(methylthio)-6,7-dihydro-5H-pyrrolo[3,2-d]pyrimidine-6-carboxylic acid (3d) as yellow oil (353 mg, 100%). MS-ESI (m/z): 338[M+1]$^+$. This was carried on to next reaction without further purification.

5-Acetyl-7-cyclopentyl-7-hydroxy-N,N-dimethyl-2-(methylthio)-6,7-dihydro-5H-pyrrolo[3,2-d]pyrimidine-6-carboxamide (3e)

To a mixture of 3d (220 mg, 0.651 mmol), dimethylamine hydrochloride (106 mg, 1.30 mmol), EDCI (187 mg, 0.977 mmol) and HOBT hydrate (150 mg, 0.977 mmol) in anhydrous DMF (4 mL) was added DIPEA (567 L, 3.26 mmol). The mixture was stirred at room temperature for 17 h. The mixture was diluted with water and extracted with ethyl acetate (2×). The extracts were washed with brine and dried ($Na_2SO_4$). Solvents were evaporated under reduced pressure. The residue was purified by silica gel column, eluted with 50%-100% ethyl acetate in hexanes to give 5-acetyl-7-cyclopentyl-7-hydroxy-N,N-dimethyl-2-(methylthio)-6,7-dihydro-5H-pyrrolo[3,2-d]pyrimidine-6-carboxamide (3e) as white solid (127 mg, 54%). MS-ESI (m/z): 365 [M+1]$^+$.

5-Acetyl-7-cyclopentyl-7-hydroxy-N,N-dimethyl-2-(methylsulfonyl)-6,7-dihydro-5H-pyrrolo[3,2-d]pyrimidine-6-carboxamide (3f)

To a solution of 3e (169 mg, 0.465 mmol) in dichloromethane (10 mL) at 0° C. was added mCPBA (75%, 267 mg, 1.16 mmol). The mixture was stirred at room temperature for 2 h. Saturated aqueous $NaHSO_3$ (3 mL) was added and stirred for 10 min. The mixture was diluted with saturated aqueous $NaHCO_3$ (20 mL) and extracted with DCM (2×15 mL). The extracts were dried ($Na_2SO_4$). Solvents were evaporated under reduced pressure to give crude 5-acetyl-7-cyclopentyl-7-hydroxy-N,N-dimethyl-2-(methylsulfonyl)-6,7-dihydro-5H-pyrrolo[3,2-d]pyrimidine-6-carboxamide (3f) as white solid (184 mg, 100%). MS-ESI (m/z): 397 [M+1]$^+$.

tert-Butyl 4-(6-(5-acetyl-7-cyclopentyl-6-(dimethylcarbamoyl)-7-hydroxy-6,7-dihydro-5H-pyrrolo[3,2-d]pyrimidin-2-ylamino)pyridin-3-yl)piperazine-1-carboxylate (3g)

To a solution of tert-butyl 4-(6-formamidopyridin-3-yl) piperazine-1-carboxylate (69.0 mg, 0.225 mmol) in DMF (1 mL) at room temperature was added NaH (60%, 15 mg, 0.36 mmol). The mixture was stirred at room temperature for 20 min. A solution of 3f (85.0 mg, 0.215 mmol) in DMF (1 mL) was added. The mixture was stirred at room temperature for 1 h. Methanol (3 mL) was added and stirred for 30 min. The mixture was diluted with water (10 mL) and extracted with ethyl acetate (2×10 mL). The extracts were dried ($Na_2SO_4$). Solvents were evaporated under reduced pressure. The residue was purified by column on silica gel, eluted with 50-100% EtOAc-hexanes and 5% methanol in EtOAc to give tert-butyl 4-(6-(5-acetyl-7-cyclopentyl-6-(dimethylcarbamoyl)-7-hydroxy-6,7-dihydro-5H-pyrrolo[3,2-d]pyrimidin-2-ylamino)pyridin-3-yl)piperazine-1-carboxylate (3g) as white solid (39.0 mg, 30%). MS-ESI (m/z): 595 [M+1]$^+$.

7-Cyclopentyl-N,N-dimethyl-2-(5-(piperazin-1-yl) pyridin-2-ylamino)-5H-pyrrolo[3,2-d]pyrimidine-6-carboxamide (3)

A solution of 3g (14.3 mg) in 0.5 M $H_2SO_4$/methanol (1 mL) was heated at 50° C. for 16 h. The mixture was cooled to room temperature. $NaHCO_3$ (90 mg) was added and stirred for 10 min. Solvents were evaporated under reduced pressure. The residue was purified by silica gel column, eluted with 94:5:1 DCM/methanol/ammonia to give 7-cyclopentyl-N,N-dimethyl-2-(5-(piperazin-1-yl)pyridin-2-ylamino)-5H-pyrrolo[3,2-d]pyrimidine-6-carboxamide (3) as pale yellow solid (3.0 mg, 29%). MS-ESI (m/z): 435 [M+1]$^+$.

Example 4

7-Cyclopentyl-N,N-dimethyl-2-(5-(4-methylpiperazin-1-yl)pyridin-2-ylamino)-5H-pyrrolo[3,2-d]pyrimidine-6-carboxamide (4)

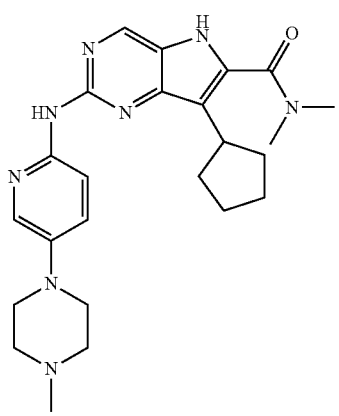

5-Acetyl-7-cyclopentyl-7-hydroxy-N,N-dimethyl-2-(5-(piperazin-1-yl)pyridin-2-ylamino)-6,7-dihydro-5H-pyrrolo[3,2-d]pyrimidine-6-carboxamide (4a)

To a solution of 3g (24.7 mg, 0.0416 mmol) in DCM (1 mL) was added TFA (1.5 mL). The mixture was stirred at room temperature for 1.5 h. Solvents were evaporated under reduced pressure. The residue was purified by silica gel column, eluted with 92:7:1 DCM-MeOH—NH$_3$ (28%) to give 5-acetyl-7-cyclopentyl-7-hydroxy-N,N-dimethyl-2-(5-(piperazin-1-yl)pyridin-2-ylamino)-6,7-dihydro-5H-pyrrolo[3,2-d]pyrimidine-6-carboxamide (4a) as pale yellow solid (7.0 mg, 34%). MS-ESI (m/z): 495[M+1]$^+$.

5-Acetyl-7-cyclopentyl-7-hydroxy-N,N-dimethyl-2-(5-(4-methylpiperazin-1-yl) pyridin-2-ylamino)-6,7-dihydro-5H-pyrrolo[3,2-d]pyrimidine-6-carboxamide (4b)

To a solution of 4a (7.0 mg, 0.014 mmol) in 1,2-dichloroethane (0.3 mL) at room temperature was added formaldehyde (37% in water, 14 mg, 0.17 mmol) followed by NaBH(OAc)$_3$ (4.5 mg, 0.021 mmol). The mixture was stirred at room temperature for 1 h. The mixture was diluted with saturated aqueous NaHCO$_3$ (5 mL) and extracted with DCM (2×5 mL). The extracts were dried (Na$_2$SO$_4$). Solvents were evaporated under reduced pressure. The residue was purified by silica gel column, eluted with 96:3:1 DCM/methanol/ammonia to give 5-acetyl-7-cyclopentyl-7-hydroxy-N,N-dimethyl-2-(5-(4-methylpiperazin-1-yl) pyridin-2-ylamino)-6,7-dihydro-5H-pyrrolo[3,2-d]pyrimidine-6-carboxamide (4b) as pale yellow solid (5.5 mg, 76%). MS-ESI (m/z): 509 [M+1]$^+$.

7-Cyclopentyl-N,N-dimethyl-2-(5-(4-methylpiperazin-1-yl)pyridin-2-ylamino)-5H-pyrrolo[3,2-d]pyrimidine-6-carboxamide (4)

A solution of 4b (5.5 mg) in 0.5 M H$_2$SO$_4$/methanol (1 mL) was heated at 50° C. for 14 h. The mixture was cooled to room temperature. NaHCO$_3$ (90 mg) was added and stirred for 10 min. Solvents were evaporated under reduced pressure. The residue was purified by silica gel column, eluted with 94:5:1 DCM/methanol/ammonia to give 7-cyclopentyl-N,N-dimethyl-2-(5-(4-methylpiperazin-1-yl)pyridin-2-ylamino)-5H-pyrrolo[3, 2-d]pyrimidine-6-carboxamide (4) as pale yellow solid (4.3 mg, 89%). MS-ESI (m/z): 449 [M+1]$^+$.

Example 5

7-cyclopentyl-N,N-dimethyl-2-((5-(piperazin-1-yl)pyridin-2-yl)amino)pyrrolo[2,1-f][1,2,4]triazine-6-carboxamide (5)

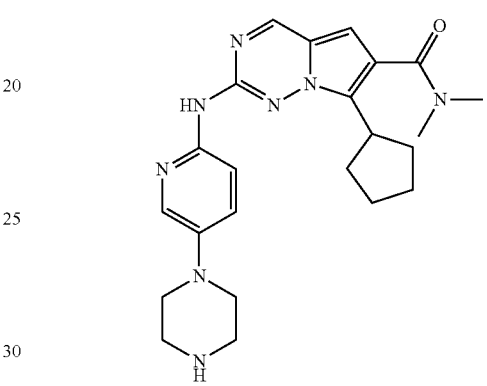

6-methyl-3-thioxo-3,4-dihydro-1,2,4-triazin-5(2H)-one (5a)

To the solution of pyruvic acid (18.4 g, 0.2 mol) in water (400 mL) was added thiosemicarbazide (18.4 g, 0.2 mol) at room temperature, then reaction mixture was heated to 70° C. and stirred for 1 h. Reaction mixture was cooled to room temperature, Na$_2$CO$_3$ (21.2 g, 0.2 mol) was carefully added to the above mixture in several portions over 30 min, then reaction mixture was heated to reflux for 3 h. Reaction mixture was cooled to room temperature, acidified with acetic acid to pH 5. This suspension was extracted with EtOAc (500 mL×2), EtOAc layer was washed with water, brine, dried with anhydrous Na$_2$SO$_4$, filtered and the solvent was removed, giving pale yellow solid 6-methyl-3-thioxo-3,4-dihydro-1,2,4-triazin-5(2H)-one (5a) (23.6 g). MS-ESI (m/z): 144 [M+1]$^+$.

6-methyl-3-(methylthio)-1,2,4-triazin-5(4H)-one (5b)

To the solution of 5a (23.6 g, 165 mmol) in 1N NaOH aq. (330 mL) was added dropwise MeI (10.3 mL, 165 mmol) at room temperature, then reaction mixture was stirred for 1 h, and acidified with acetic acid to pH 5. This suspension was filtered, washed with water (500 mL×2), dried in vacuo to give the product 6-methyl-3-(methylthio)-1,2,4-triazin-5(4H)-one (5b) (14.5 g). MS-ESI (m/z): 158 [M+1]$^+$.

5-chloro-6-methyl-3-(methylthio)-1,2,4-triazine (5c)

The mixture of 5b (14.5 g, 92 mmol) in POCl$_3$ (120 mL) was heated to reflux for 1 h, then reaction mixture was cooled to 50° C., and concentrated in vacuo to ⅓ volume.

The resulting residue was diluted with DCM (500 mL), washed with cold water (500 mL×5), brine (500 mL×2), dried with anhydrous $Na_2SO_4$, filtered and the solvent was removed, giving black residue 5-chloro-6-methyl-3-(methylthio)-1,2,4-triazine (5c) (9.6 g). MS-ESI (m/z): 176 $[M+1]^+$.

6-methyl-3-(methylthio)-1,2,4-triazine (5d)

To the ice-water cooled suspension of 5c (9.6 g, 55 mmol) in i-PrOH (210 mL) was added $NaBH_4$ (10.5g, 275 mmol) in several portions, then the reaction mixture was stirred at 0-5° C. for 1 h. The mixture was filtrated, washed with cooled i-PrOH (20 mL). The filtrate was concentrated in vacuo. To the crude product was added DCM (300 mL) and DDQ (12.5 g, 55 mmol), the mixture was stirred at room temperature for 16 h, filtrated, filtrate was concentrated in vacuo and purified through flash column chromatography (eluent: petro ether/ethyl acetate=50:1→10:1) to give 6-methyl-3-(methylthio)-1,2,4-triazine (5d) (2.3 g). MS-ESI (m/z): 142 $[M+1]^+$.

6-(bromomethyl)-3-(methylthio)-1,2,4-triazine (5e)

To the solution of 5d (2.3 g, 16.3 mmol) in $CCl_4$ (80 mL) was added NBS (3.2 g, 17.9 mmol), and BPO (395 mg, 1.63 mmol). This mixture was heated to reflux for 1 h and cooled to room temperature, additional NBS (3.2 g, 17.9 mmol), and BPO (395 mg, 1.63 mmol) was added to the above mixture. This resulting mixture was heated to reflux again for 1 h. After cooled to room temperature, the mixture was filtrated, washed with DCM (20 mL). Filtrate was combined, washed with sat. $Na_2SO_3$ aq. brine, dried with anhydrous $Na_2SO_4$, filtered and the filtrate was concentrated in vacuo and purified through flash column chromatography (eluent: petro ether/ethyl acetate=50:1→25:1) to give 6-(bromomethyl)-3-(methylthio)-1,2,4-triazine (5e) (0.88 g). MS-ESI (m/z): 220, 222 $[M+1]^+$.

ethyl 3-cyclopentyl-2-((3-(methylthio)-1,2,4-triazin-6-yl)methyl)-3-oxopropanoate (5f)

To the ice-water cooled solution of ethyl 3-cyclopentyl-3-oxopropanoate (1.47 g, 8.0 mmol) in DMF (8.0 mL) was added 60% NaH (160 mg, 4.0 mmol), after stirring for 10 min at room temperature, the mixture was recooled to 0-5° C., the solution of 5e (0.88 g, 4.0 mmol) in DMF (4.0 mL) was added to the above solution, then reaction mixture was slowly warmed to room temperature and stirred for 1 h, quenched with sat. NH4Cl aq., extracted with EtOAc. Organic layer was washed with water and brine, dried with anhydrous $Na_2SO_4$, filtered and the filtrate was concentrated in vacuo and purified through flash column chromatography (eluent: petro ether/ethyl acetate=50:1→10:1) to give ethyl 3-cyclopentyl-2-((3-(methylthio)-1,2,4-triazin-6-yl)methyl)-3-oxopropanoate (5f) (0.75 g). MS-ESI (m/z): 324 $[M+1]^+$.

ethyl 7-cyclopentyl-2-(methylthio)pyrrolo[2,1-f][1,2,4]triazine-6-carboxylate (5g)

The mixture of 5f (0.75 g, 2.3 mmol) in $POCl_3$ (23 mL) was heated to reflux for 16 h. Then reaction mixture cooled to 50° C. and concentrated in vacuo, this crude product ethyl 7-cyclopentyl-2-(methylthio)pyrrolo[2,1-f][1,2,4]triazine-6-carboxylate (5g) was used in next step without further purification. MS-ESI (m/z): 306 $[M+1]^+$.

7-cyclopentyl-2-(methylthio)pyrrolo[2,1-f][1,2,4]triazine-6-carboxylic acid (5h)

To the mixture of 5g (700 mg, 2.3 mmol) in THF/MeOH/$H_2O$ (36 mL, v:v:v=1:1:1) was added $LiOH.H_2O$ (1.45 g, 34.5 mmol), this mixture was stirred at room temperature for 16 h, acidified with 1 N HCl aq. to pH 2-3, extracted with EtOAc, the organic layer was washed with water, brine, dried with anhydrous $Na_2SO_4$, filtered and concentrated in vacuo. The residue 7-cyclopentyl-2-(methylthio)pyrrolo[2,1-f][1,2,4]triazine-6-carboxylic acid (5h) was used in next step without further purification. MS-ESI (m/z): 278 $[M+1]^+$.

7-cyclopentyl-N,N-dimethyl-2-(methylthio)pyrrolo[2,1-f][1,2,4]triazine-6-carboxamide (5i)

The mixture of 5h (554 mg, 2.0 mmol), HOBT (540 mg, 4.0 mmol), EDCI (575 mg, 3.0 mmol), dimethylamine hydrochloride (489 mg, 6.0 mmol), $Et_3N$ (1.39 mL, 10.0 mmol) and MS4 Å (2.0 g) in DMF (20 mL) was stirred at room temperature for 16 h. The mixture was extracted with water and EtOAc, organic layer was washed with water, brine, dried with anhydrous $Na_2SO_4$, filtered and concentrated in vacuo. The residue 7-cyclopentyl-N,N-dimethyl-2-(methylthio)pyrrolo[2, 1-f][1,2,4]triazine-6-carboxamide (5i) was used in next step without further purification. MS-ESI (m/z): 305 $[M+1]^+$.

7-cyclopentyl-N,N-dimethyl-2-(methylsulfinyl)pyrrolo[2,1-][1,2,4]triazine-6-carboxamide (5j)

To the solution of 5i (630 mg, 2.0 mmol) in DCM (20 mL) was added m-CPBA (460 mg, 2.0 mmol), reaction mixture was stirred at ambient temperature for 1 h. The mixture was quenched with sat. $NaHCO_3$ aq., DCM layer was washed with water, brine, dried with anhydrous $Na_2SO_4$, filtered and concentrated in vacuo. The residue 7-cyclopentyl-N,N-dimethyl-2-(methyl sulfinyl)pyrrolo[2,1-f][1,2,4]triazine-6-carboxamide (5j) was used in next step without further purification. MS-ESI (m/z): 321 $[M+1]^+$.

7-cyclopentyl-2-((4-methoxybenzyl)amino)-N,N-dimethylpyrrolo[2,1-f][1,2,4]triazine-6-carboxamide (5k)

To the solution of 5j (665 mg, 2.0 mmol) in NMP (20 mL) was added $PMBNH_2$ (1.30 mL, 10.0 mmol), reaction mixture was heated to 80° C. and stirred for 16 h. The mixture was cooled to ambient temperature and extracted with water and EtOAc, organic layer was washed with water, brine, dried with anhydrous $Na_2SO_4$, filtered and concentrated in vacuo. The residue 7-cyclopentyl-2-((4-methoxybenzyl)amino)-N,N-dimethylpyrrolo [2,1-f][1,2,4]triazine-6-carboxamide (5k) was used in next step without further purification. MS-ESI (m/z): 394 $[M+1]^+$.

2-amino-7-cyclopentyl-N,N-dimethylpyrrolo[2,1-f][1,2,4]triazine-6-carboxamide (5l)

To the solution of 5k (≈500 mg, 1.0 mmol) in DCM (10 mL) was added dropwise TFA (10 mL), reaction mixture was stirred at ambient temperature for 5 h. The mixture was concentrated in vacuo and basified with ammonia to pH 9-10, concentrated in vacuo. The residue was purified through flash column chromatography (eluent: DCM/Methanol=100:1→10:1) to give 2-amino-7-cyclopentyl-N,N-dimethylpyrrolo[2,1-f][1,2,4]triazine-6-carboxamide (5l) (136 mg). MS-ESI (m/z): 274 [M+1]⁺.

tert-butyl 4-(6-((7-cyclopentyl-6-(dimethylcarbamoyl)pyrrolo[2,1-f][1,2,4]triazin-2-yl)amino)pyridin-3-yl)piperazine-1-carboxylate (5m)

The mixture of 5l (10 mg, 0.03663 mmol), tert-butyl 4-(6-chloropyridin-3-yl) piperazine-1-carboxylate (22 mg, 0.07326 mmol), Pd₂dba₃ (12.8 mg, 0.01832 mmol), Xphos (21.2 mg, 0.03663 mmol), and ᵗBuONa (10.5 mg, 0.11 mmol) in 1,4-dioxane (0.72 mL) was heated to 105° C. and stirred under N₂ for 16 h. Then mixture was cooled to room temperature and diluted with EtOAc, filtered through a pad of celite, filtrate was concentrated in vacuo and purified through flash column chromatography (eluent: DCM/Methanol=100:1→10:1) to give tert-butyl 4-(6-((7-cyclopentyl-6-(dimethylcarbamoyl)pyrrolo[2,1-f][1,2,4]triazin-2-yl)amino) pyridin-3-yl)piperazine-1-carboxylate (5m) (7.0 mg). MS-ESI (m/z): 535 [M+1]⁺.

7-cyclopentyl-N,N-dimethyl-2-((5-(piperazin-1-yl)pyridin-2-yl)amino)pyrrolo[2,1-f][1,2,4]triazine-6-carboxamide (5)

The mixture of 5m (7.0 mg, 0.0131 mmol) in 4N HCl/EtOAc (1 mL) was stirred for 3 h. Then mixture was concentrated in vacuo and basified with ammonia to pH 9-10, concentrated in vacuo again, purified through flash column chromatography (eluent: DCM/Methanol=10:1) to give 7-cyclopentyl-N,N-dimethyl-2-((5-(piperazin-1-yl)pyridine-2-yl)amino)pyrrolo[2,1-f][1,2,4]triazine-6-carboxamide (5) (4.6 mg). MS-ESI (m/z): 435 [M+1]⁺.

Example 6

7-cyclopentyl-N,N-dimethyl-2-((5-(4-methylpiperazin-1-yl)pyridin-2-yl)amino) pyrrolo[2,1-f][1,2,4]triazine-6-carboxamide (6)

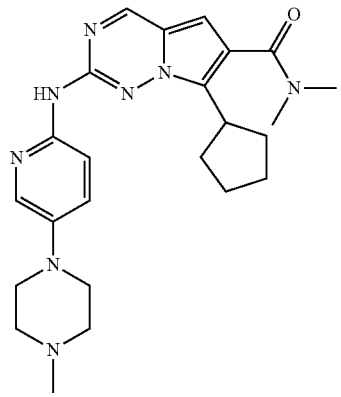

The mixture of 5l (11 mg, 0.040 mmol), 1-(6-chloropyridin-3-yl)-4-methylpiperazine (15 mg, 0.071 mmol), Pd₂dba₃ (7.0 mg, 0.010 mmol), Xphos (11.6 mg, 0.020 mmol), and ᵗBuONa (19.2 mg, 0.20 mmol) in 1,4-dioxane (1.2 mL) was heated to 105° C. and stirred under N₂ for 16 h. Then mixture was cooled to room temperature and diluted with EtOAc, filtered through a pad of celite, filtrate was concentrated in vacuo and purified through flash column chromatography (eluent: DCM/Methanol=10:1) to give 7-cyclopentyl-N,N-dimethyl-2-((5-(4-methylpiperazin-1-yl)pyridin-2-yl)amino)pyrrolo[2,1-f][1,2,4]triazine-6-carboxamide (6) (5.0 mg). MS-ESI (m/z): 449 [M+1]⁺.

Example 7

7-cyclopentyl-N,N-dimethyl-2-((5-(piperazin-1-yl)pyridin-2-yl)amino)furo[3,2-d]pyrimidine-6-carboxamide (7)

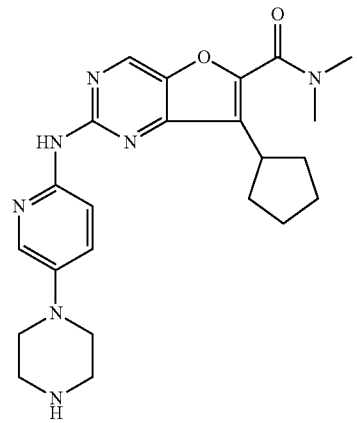

5-bromo-4-(((tert-butyldimethylsilyl)oxy)(cyclopentyl)methyl)-2-(methylthio)pyrimidine (7a)

To a solution of 1a (1.6 g, 5.28 mmol) in MeCN (26 mL) was added DBU (4.74 mL, 31.7 mmol), and TBSCl (3.98 g, 26.4 mmol) at 0-5° C. under N₂. The reaction mixture was slowly warmed to ambient temperature and stirred for 5 h, then diluted with EtOAc (50 mL), washed with 1N HCl aq. (20 mL), water (25 mL), sat. NaHCO₃ aq. (20 mL), brine, and dried with anhydrous Na₂SO₄, filtered and concentrated in vacuo. The residue was purified through flash column chromatography (eluent: hexane/ethyl acetate=100:1) to give 5-bromo-4-(((tert-butyldimethylsilyl)oxy)(cyclopentyl)methyl)-2-(methylthio)pyrimidine (7a) (2.2 g). MS-ESI (m/z): 417, 419 [M+1]⁺.

(4-(((tert-butyldimethylsilyl)oxy)(cyclopentyl)methyl)-2-(methylthio)pyrimidin-5-yl)boronic acid (7b)

To the cooled solution of 7a (2.2 g, 5.2 mmol) in dry THF (52 mL) was added B(OMe)₃ (4.0 mL, 36 mmol) and n-BuLi (2.5 M in hexane, 12 mL) at −78° C. under N₂. The reaction mixture was slowly warmed to 0° C. over 2 h, and then quenched with 3N HCl aq. (13 mL), extracted with EtOAc (50 mL), washed with brine, and dried with anhydrous Na₂SO₄, filtered and concentrated in vacuo to give colorless residue (4-(((tert-butyldimethylsilyl)oxy) (cyclopentyl)methyl)-2-(methylthio)pyrimidin-5-yl)boronic acid (7b), used in next step without further purification. MS-ESI (m/z): 383 [M+1]⁺.

4-(((tert-butyldimethylsilyl)oxy)(cyclopentyl)methyl)-2-(methylthio)pyrimidin-5-ol (7c)

To the mixture of 7b (crude product, 5.2 mmol) in THF/H₂O (60 mL, v:v=1:1) was added NaBO₃.4H₂O (2.3 g, 15 mmol) in several portions at 0-5° C., then reaction mixture was warmed to ambient temperature and stirred for 5 h, quenched with 1N HCl to pH2-3, extracted with EtOAc, washed with water, brine, dried with anhydrous $Na_2SO_4$, filtered and concentrated in vacuo. The residue was purified through flash column chromatography (eluent: hexane/ethyl acetate=20:1) to give 4-(((tert-butyldimethylsilyl)oxy)(cyclopentyl)methyl)-2-(methylthio)pyrimidin-5-ol (7c) (1.6 g). MS-ESI (m/z): 355 [M+1]$^+$.

ethyl 2-((4-(((tert-butyldimethylsilyl)oxy)(cyclopentyl)methyl)-2-(methylthio) pyrimidin-5-yl)oxy)acetate (7d)

To the solution of 7c (1.6 g, 4.5 mmol) and ethyl 2-bromoacetate (0.5 mL, 4.5 mmol) in DMF (23 mL) was added $Cs_2CO_3$ (2.2 g, 6.8 mmol) at ambient temperature, then reaction mixture was stirred for 1 h, quenched with sat. $NH_4Cl$ aq., extracted with EtOAc, washed with water, brine, dried with anhydrous $Na_2SO_4$, filtered and concentrated in vacuo to give residue ethyl 2-((4-(((tert-butyldimethylsilyl)oxy)(cyclopentyl)methyl)-2-(methylthio) pyrimidin-5-yl)oxy)acetate (7d). This residue was used in next step without further purification. MS-ESI (m/z): 441 [M+1]$^+$.

ethyl 2-((4-(cyclopentyl(hydroxy)methyl)-2-(methylthio)pyrimidin-5-yl)oxy) acetate (7e)

To the ice-water cooled solution of 7d (crude product, 4.5 mmol) in MeCN (45 mL) was added $BF_3 \cdot Et_2O$ (3.0 mL) under $N_2$. Then reaction mixture was warmed to ambient temperature and stirred for 30 min, quenched with sat. $NaHCO_3$ aq. to pH 8-9, extracted with EtOAc, washed with water, brine, dried with anhydrous $Na_2SO_4$, filtered and concentrated in vacuo to give ethyl 2-((4-(cyclopentyl(hydroxy)methyl)-2-(methylthio)pyrimidin-5-yl)oxy) acetate (7e) (1.1 g). MS-ESI (m/z): 327 [M+1]$^+$.

ethyl 2-((4-(cyclopentanecarbonyl)-2-(methylthio)pyrimidin-5-yl)oxy)acetate (7f)

To the ice-water cooled solution of 7e (490 mg, 1.5 mmol) in DCM (20 mL) was added Dess-Martin periodinane (1.28 g, 3.0 mmol), the reaction mixture was warmed to room temperature and stirred for 1 h, quenched with sat. $NaHCO_3$ aq. (10 mL), washed with brine, and dried with anhydrous $Na_2SO_4$, filtered and concentrated in vacuo. The residue was purified through flash column chromatography (eluent: hexane/ethyl acetate=20:1) to give ethyl 2-((4-(cyclopentanecarbonyl)-2-(methylthio)pyrimidin-5-yl)oxy)acetate (7f) (320 mg). MS-ESI (m/z): 325 [M+1]$^+$.

7-cyclopentyl-2-(methylthio)furo[3,2-d]pyrimidine-6-carboxylic acid (7g)

To the ice-water cooled solution of 7f (290 mg, 0.9 mmol) in THF (11 mL) was added 60% NaH (125 mg, 3.2 mmol), the reaction mixture was slowly warmed to room temperature and stirred for 30 min, quenched with 1N HCl aq. to pH 2-3, extracted with EtOAc, washed with brine, and dried with anhydrous $Na_2SO_4$, filtered and concentrated in vacuo to give 7-cyclopentyl-2-(methylthio)furo[3,2-d]pyrimidine-6-carboxylic acid (7g). MS-ESI (m/z): 279 [M+1]$^+$.

7-cyclopentyl-N,N-dimethyl-2-(methylthio)furo[3,2-d]pyrimidine-6-carboxamide (7h)

The mixture of 7g (crude product, 0.90 mmol), HOBT (243 mg, 1.59 mmol), EDCI (228 mg, 1.19 mmol), dimethylamine hydrochloride (194 mg, 2.38 mmol), and DIPEA (0.65 mL, 3.97 mmol) in DMF (16 mL) was stirred at ambient temperature for 16 h, quenched with 1N HCl to pH2-3, extracted with EtOAc, washed with water, brine, dried with anhydrous $Na_2SO_4$, filtered and concentrated in vacuo to give 7-cyclopentyl-N,N-dimethyl-2-(methylthio)furo[3,2-d]pyrimidine-6-carboxamide (7h). MS-ESI (m/z): 306 [M+1]$^+$.

7-cyclopentyl-N,N-dimethyl-2-(methylsulfonyl)furo[3,2-d]pyrimidine-6-carboxamide (7i)

To the solution of 7h (crude product) in DCM (16 mL) was added m-CPBA (355 mg, 1.59 mmol), reaction mixture was stirred at ambient temperature for 1 h, quenched with sat. $NaHCO_3$ aq. DCM layer was washed with water, brine, dried with anhydrous $Na_2SO_4$, filtered and concentrated in vacuo. The residue was purified through flash column chromatography (eluent: hexane/acetone=2:1) to give 7-cyclopentyl-N,N-dimethyl-2-(methylsulfonyl)furo[3,2-d]pyrimidine-6-carboxamide (7i) (69 mg). MS-ESI (m/z): 338 [M+1]$^+$.

tert-butyl 4-(6-((7-cyclopentyl-6-(dimethylcarbamoyl)furo[3,2-d]pyrimidin-2-yl)amino)pyridin-3-yl)piperazine-1-carboxylate (7j)

To the ice-water cooled solution of 7i (33.7 mg, 0.1 mmol) and tert-butyl 4-(6-formamidopyridin-3-yl)piperazine-1-carboxylate (30.6 mg, 0.1 mmol) in DMF (2 mL) was added 60% NaH (8.0 mg, 0.2 mmol), the reaction mixture was slowly warmed to room temperature and stirred for 2 h, quenched with sat. $NH_4Cl$ aq., extracted with EtOAc, washed with brine, and dried with anhydrous $Na_2SO_4$, filtered and concentrated in vacuo. The residue was purified through flash column chromatography (eluent: DCM/Methanol=50:1) to give tert-butyl 4-(6-((7-cyclopentyl-6-(dimethylcarbamoyl)furo[3,2-d]pyrimidin-2-yl)amino)pyridine-3-yl)piperazine-1-carboxylate (7j) (5.3 mg). MS-ESI (m/z): 536 [M+1]$^+$.

7-cyclopentyl-N,N-dimethyl-2-((5-(piperazin-1-yl)pyridin-2-yl)amino)furo[3,2-d]pyrimidine-6-carboxamide (7)

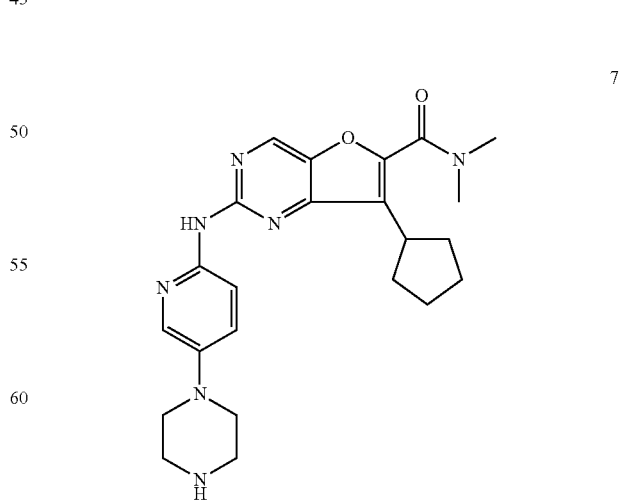

To the solution of 7j (5.3 mg, 0.01 mmol) in DCM (0.5 mL) was added TFA (0.5 mL) at ambient temperature. This mixture was stirred for 40 min, and concentrated in vacuo, basified with ammonia to pH 9-10 and concentrated in vacuo again. The residue was purified through flash column chromatography (eluent: DCM/MeOH=10:1) to give 7-cyclopentyl-N,N-dimethyl-2-((5-(piperazin-1-yl)pyridin-2-yl)amino)furo[3,2-d]pyrimidine-6-carboxamide (7) (2.8 mg). MS-ESI (m/z): 436 [M+1]⁺.

Example 8

7-cyclopentyl-N,N-dimethyl-2-((5-(4-methylpiperazin-1-yl)pyridin-2-yl)amino) furo[3,2-d]pyrimidine-6-carboxamide (8)

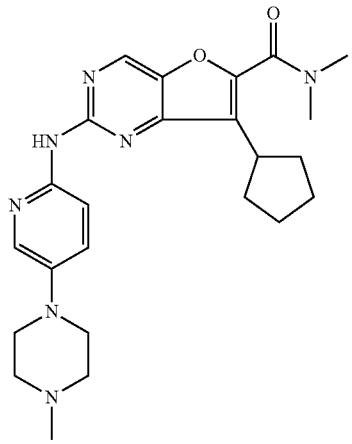

To the ice-water cooled solution of 7i (33.7 mg, 0.1 mmol) and N-(5-(4-methylpiperazin-1-yl)pyridin-2-yl)formamide (22.0 mg, 0.1 mmol) in DMF (2 mL) was added 60% NaH (8.0 mg, 0.2 mmol), the reaction mixture was slowly warmed to room temperature and stirred for 2 h, quenched with sat. NH₄Cl aq., extracted with EtOAc, washed with brine, and dried with anhydrous Na₂SO₄, filtered and concentrated in vacuo. The residue was purified through flash column chromatography (eluent: DCM/Methanol=10:1) to give 7-cyclopentyl-N,N-dimethyl-2-((5-(4-methylpiperazin-1-yl)pyridin-2-yl)amino)furo[3,2-d]pyrimidine-6-carboxamide (8) (2.4 mg). MS-ESI (m/z): 450 [M+1]⁺.

Example 9

7-Cyclopentyl-N,N,5-trimethyl-2-(5-(piperazin-1-yl)pyridin-2-ylamino)-5H-pyrrolo[3,2-d]pyrimidine-6-carboxamide (9)

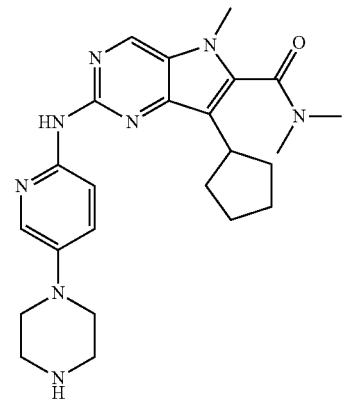

tert-Butyl 4-(6-(7-cyclopentyl-6-(dimethylcarbamoyl)-5H-pyrrolo[3,2-d]pyrimidin-2-ylamino)pyridin-3-yl)piperazine-1-carboxylate (9a)

To a solution of 3 (11.2 mg) in DCM (0.5 mL) was added Boc₂O (6.1 mg) followed by TEA (5.4 μL). The mixture was stirred at room temperature for 2 h. Solvents were evaporated under reduced pressure. The residue was purified by silica gel column, eluted with 95:5 DCM/methanol to give tert-Butyl 4-(6-(7-cyclopentyl-6-(dimethylcarbamoyl)-5H-pyrrolo[3,2-d]pyrimidin-2-ylamino)pyridin-3-yl)piperazine-1-carboxylate (9a) as pale yellow solid (12.0 mg, 87%). MS-ESI (m/z): 535.5 [M+1]⁺.

tert-Butyl 4-(6-(7-cyclopentyl-6-(dimethylcarbamoyl)-5-methyl-5H-pyrrolo[3,2-d]pyrimidin-2-ylamino)pyridin-3-yl)piperazine-1-carboxylate (9b)

To a solution of 9a (12.0 mg, 0.0225 mmol) in THF (0.5 mL) was NaH (60%, 2.0 mg, 0.050 mmol). After stirring at rt for 10 min., a solution of MeI (3.2 mg, 0.0225 mmol) in THF (0.25 mL) was added. The mixture was stirred at room temperature for 2.5 h. Solvents were evaporated under reduced pressure. The residue was purified by silica gel column, eluted with 3% MeOH in DCM and then with 92:7:1 DCM-MeOH—NH₃ (28%) to give tert-Butyl 4-(6-(7-cyclopentyl-6-(dimethylcarbamoyl)-5-methyl-5H-pyrrolo[3,2-d]pyrimidin-2-ylamino) pyridin-3-yl)piperazine-1-carboxylate (9b) as pale yellow solid (7.9 mg, 64%). MS-ESI (m/z): 549.5 [M+1]⁺.

7-Cyclopentyl-N,N,5-trimethyl-2-(5-(piperazin-1-yl)pyridin-2-ylamino)-5H-pyrrolo[3,2-d]pyrimidine-6-carboxamide (9)

To a solution of 9b (7.8 mg) in DCM (0.5 mL) was added TFA (0.5 mL). The mixture was stirred at room temperature for 1 h. Solvents were evaporated under reduced pressure. The residue was purified by silica gel column, eluted with 91:8:1 DCM-MeOH—NH₃ (28%) to give 7-Cyclopentyl-N,N,5-trimethyl-2-(5-(piperazin-1-yl)pyridin-2-ylamino)-5H-pyrrolo[3,2-d]pyrimidine-6-carboxamide (9) as pale yellow solid (6.4 mg, 100%). MS-ESI (m/z): 449.4[M+1]⁺.

Example 10

7-Cyclopentyl-N,N, 5-trimethyl-2-(5-(4-methylpiperazin-1-yl)pyridin-2-ylamino)-5H-pyrrolo[3,2-d]pyrimidine-6-carboxamide (10)

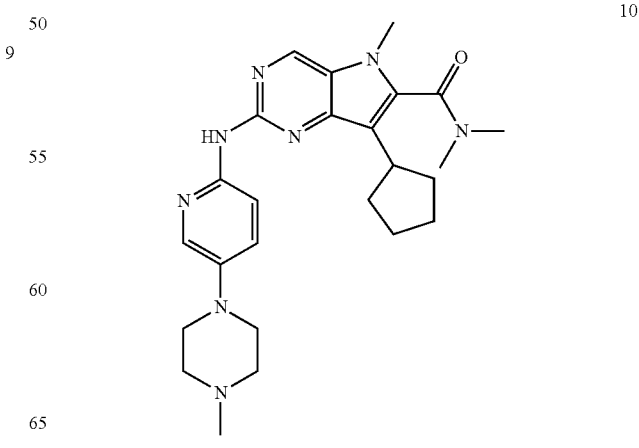

To a solution of 9 (3.9 mg, 0.0087 mmol) in 1,2-dichloroethane (0.3 mL) at room temperature was added formaldehyde (37% in water, 9.2 mg, 0.11 mmol) followed by NaBH(OAc)₃ (2.4 mg, 0.011 mmol). The mixture was stirred at room temperature for 1 h. The mixture was diluted with saturated aqueous NaHCO₃ (1 mL) and extracted with DCM (2×1 mL). The extracts were dried (Na₂SO₄). Solvents were evaporated under reduced pressure. The residue was purified by silica gel column, eluted with 95:4:1 DCM/methanol/ammonia to give 7-cyclopentyl-N,N,5-trimethyl-2-(5-(4-methylpiperazin-1-yl)pyridin-2-ylamino)-5H-pyrrolo[3,2-d]pyrimidine-6-carboxamide (10) as pale yellow solid (2.6 mg, 65%). MS-ESI (m/z): 463.4 [M+1]⁺.

Following essentially the same procedures described for Examples 1, Examples 11-64 listed in Table 1 were prepared by replacing tert-butyl 4-(6-formamidopyridin-3-yl)piperazine-1-carboxylate with the corresponding aminopyridines or aminopyridazines and sequential modifications as necessary, such as acylation and reductive amination, or using similar synthetic strategies or methods. The structures and names of Examples 11-64 are given in Table 1.

TABLE 1

| EXAMPLE | STRUCTURE | NAME | DATA |
| --- | --- | --- | --- |
| 11 | 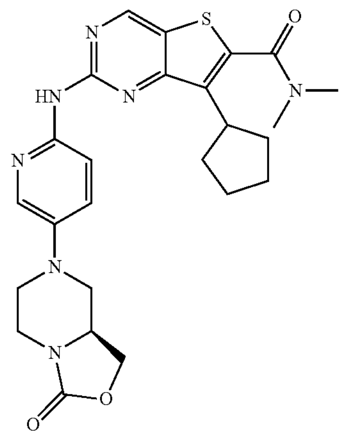 [SMILES: CN(C)C(=O)c1sc2cnc(Nc3ccc(N4CCN5C(=O)OC[C@@H]5C4)cn3)nc2c1C1CCCC1] | (S)-7-cyclopentyl-N,N-dimethyl-2-((5-(3-oxotetrahydro-3H-oxazolo[3,4-a]pyrazin-7(1H)-yl)pyridin-2-yl)amino)thieno[3,2-d]pyrimidine-6-carboxamide | MS-ESI (m/z): 508 [M + 1]⁺ |
| 12 | 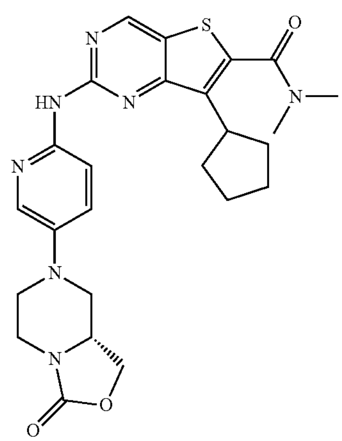 [SMILES: CN(C)C(=O)c1sc2cnc(Nc3ccc(N4CCN5C(=O)OC[C@H]5C4)cn3)nc2c1C1CCCC1] | (R)-7-cyclopentyl-N,N-dimethyl-2-((5-(3-oxotetrahydro-3H-oxazolo[3,4-a]pyrazin-7(1H)-yl)pyridin-2-yl)amino)thieno[3,2-d]pyrimidine-6-carboxamide | MS-ESI (m/z): 508 [M + 1]⁺ |
| 13 | 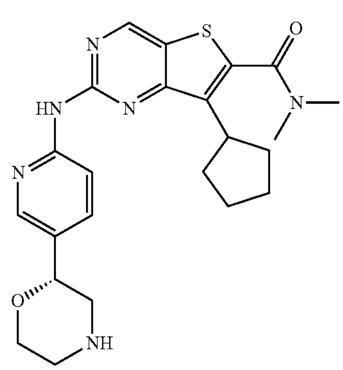 [SMILES: CN(C)C(=O)c1sc2cnc(Nc3ccc([C@@H]4CNCCO4)cn3)nc2c1C1CCCC1] | (R)-7-cyclopentyl-N,N-dimethyl-2-((5-(morpholin-2-yl)pyridin-2-yl)amino)thieno[3,2-d]pyrimidine-6-carboxamide | MS-ESI (m/z): 453 [M + 1]⁺ |

TABLE 1-continued

| EXAMPLE | STRUCTURE | NAME | DATA |
| --- | --- | --- | --- |
| 14 | 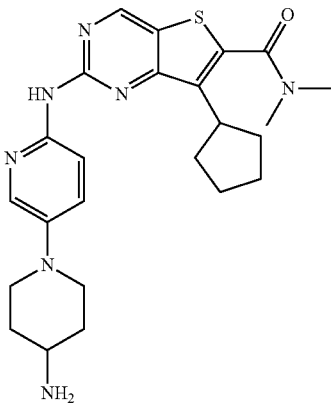 [SMILES: CN(C)C(=O)c1sc2cnc(Nc3ccc(N4CCC(N)CC4)cn3)nc2c1C1CCCC1] | 2-((5-(4-aminopiperidin-1-yl)pyridin-2-yl)amino)-7-cyclopentyl-N,N-dimethylthieno[3,2-d]pyrimidine-6-carboxamide | MS-ES (m/z): 466 [M + 1]$^+$ |
| 15 | 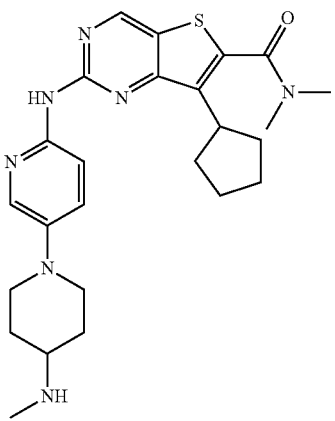 [SMILES: CNC1CCN(c2ccc(Nc3ncc4sc(C(=O)N(C)C)c(C5CCCC5)c4n3)nc2)CC1] | 7-cyclopentyl-N,N-dimethyl-2-((5-(4-(methylamino)piperidin-1-yl)pyridin-2-yl)amino)thieno[3,2-d]pyrimidine-6-carboxamide | MS-ESI (m/z): 480 [M + 1]$^+$ |
| 16 | 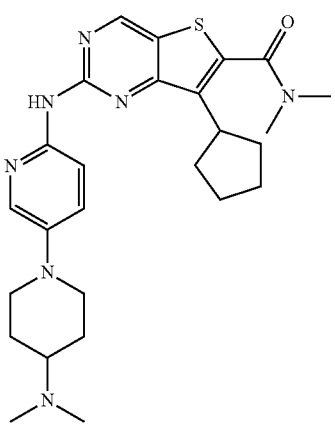 [SMILES: CN(C)C(=O)c1sc2cnc(Nc3ccc(N4CCC(N(C)C)CC4)cn3)nc2c1C1CCCC1] | 7-cyclopentyl-2-((5-(4-(dimethylamino)piperidin-1-yl)pyridin-2-yl)amino)-N,N-dimethylthieno[3,2-d]pyrimidine-6-carboxamide | MS-ESI (m/z): 494 [M + ]$^+$ |

TABLE 1-continued

| EXAMPLE | STRUCTURE | NAME | DATA |
|---|---|---|---|
| 17 | 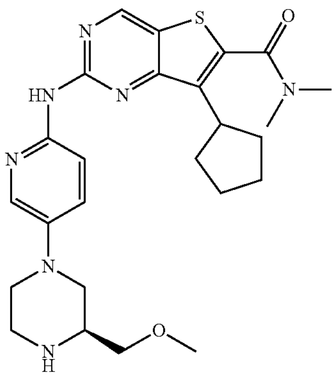 [SMILES: COC[C@@H]1CN(c2ccc(Nc3ncc4sc(C(=O)N(C)C)c(C5CCCC5)c4n3)nc2)CCN1] | (S)-7-cyclopentyl-2-((5-(3-(methoxymethyl)piperazin-1-yl)pyridin-2-yl)amino)-N,N-dimethylthieno[3,2-d]pyrimidine-6-carboxamide | MS-ESI (m/z): 496 [M + 1]+ |
| 18 | 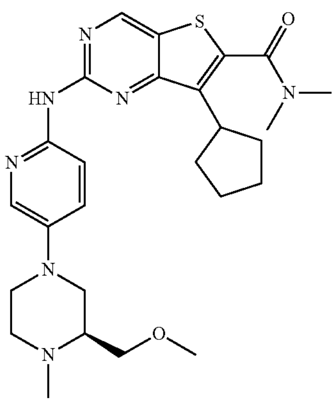 [SMILES: COC[C@@H]1CN(c2ccc(Nc3ncc4sc(C(=O)N(C)C)c(C5CCCC5)c4n3)nc2)CCN1C] | (S)-7-cyclopentyl-2-((5-(3-(methoxymethyl)-4-methylpiperazin-1-yl)pyridin-2-yl)amino)-N,N-dimethylthieno[3,2-d]pyrimidine-6-carboxamide | MS-ESI (m/z): 510 [M + 1]+ |
| 19 | 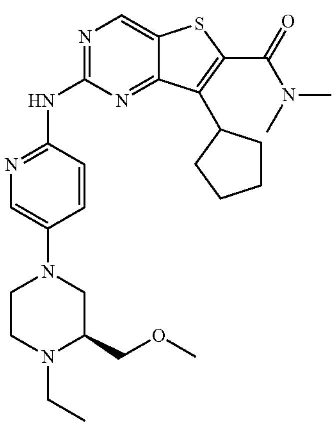 [SMILES: CCN1CCN(c2ccc(Nc3ncc4sc(C(=O)N(C)C)c(C5CCCC5)c4n3)nc2)C[C@H]1COC] | (S)-7-cyclopentyl-2-((5-(4-ethyl-3-(methoxymethyl)piperazin-1-yl)pyridin-2-yl)amino)-N,N-dimethylthieno[3,2-d]pyrimidine-6-carboxamide | MS-ESI (m/z): 524 [M + H]+ |
| 20 | 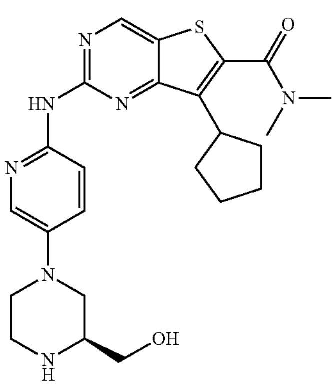 [SMILES: CN(C)C(=O)c1sc2cnc(Nc3ccc(N4CCN[C@H](CO)C4)cn3)nc2c1C1CCCC1] | (S)-7-cyclopentyl-2-((5-(3-(hydroxymethyl)piperazin-1-yl)pyridin-2-yl)amino)-N,N-dimethylthieno[3,2-d]pyrimidine-6-carboxamide | MS-ESI (m/z): 482 [M + 1]+ |

TABLE 1-continued

| EXAMPLE | STRUCTURE | NAME | DATA |
|---|---|---|---|
| 21 | 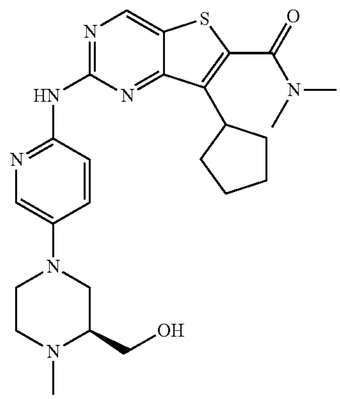 [SMILES: CN(C)C(=O)c1sc2cnc(Nc3ccc(N4CCN(C)[C@H](CO)C4)cn3)nc2c1C1CCCC1] | (S)-7-cyclopentyl-2-((5-(3-(hydroxymethyl)-4-methylpiperazin-1-yl)pyridin-2-yl)amino)-N,N-dimethylthieno[3,2-d]pyrimidine-6-carboxamide | MS-ESI (m/z): 496 [M + 1]$^+$ |
| 22 | 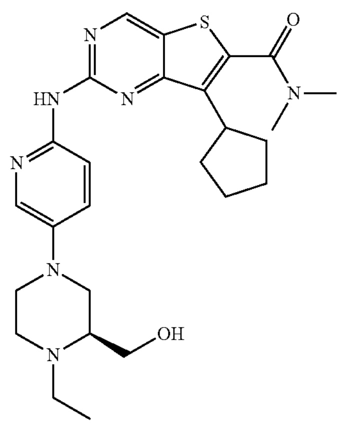 [SMILES: CCN1CCN(c2ccc(Nc3ncc4sc(C(=O)N(C)C)c(C5CCCC5)c4n3)nc2)C[C@H]1CO] | (S)-7-cyclopentyl-2-((5-(4-ethyl-3-(hydroxymethyl)piperazin-1-yl)pyridin-2-yl)amino)-N,N-dimethylthieno[3,2-d]pyrimidine-6-carboxamide | MS-ESI (m/z): 510 [M + 1]$^+$ |
| 23 | 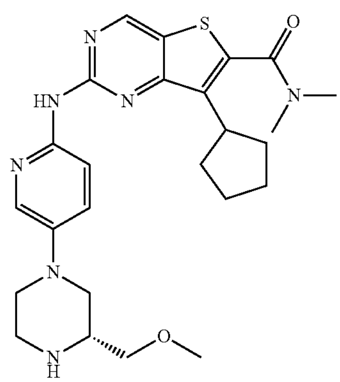 [SMILES: COC[C@H]1CN(c2ccc(Nc3ncc4sc(C(=O)N(C)C)c(C5CCCC5)c4n3)nc2)CCN1] | (R)-7-cyclopentyl-2-((5-(3-(methoxymethyl)piperazin-1-yl)pyridin-2-yl)amino)N,N-dimethylthieno[3,2-d]pyrimidine-6-carboxamide | MS-ESI (m/z): 496 [M + 1]$^+$ |
| 24 | 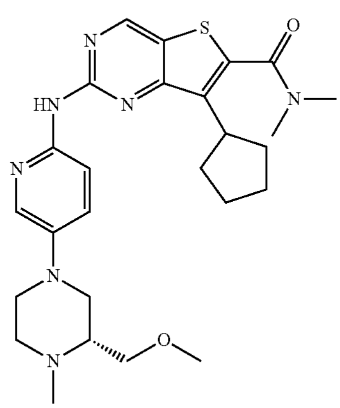 [SMILES: COC[C@H]1CN(c2ccc(Nc3ncc4sc(C(=O)N(C)C)c(C5CCCC5)c4n3)nc2)CCN1C] | (R)-7-cyclopentyl-2-((5-(3-(methoxymethyl)-4-methylpiperazin-1-yl)pyridin-2-yl)amino)-N,N-dimethylthieno[3,2-d]pyrimidine-6-carboxamide | MS-ESI (m/z): 510 [M + 1]$^+$ |

TABLE 1-continued

| EXAMPLE | STRUCTURE | NAME | DATA |
| --- | --- | --- | --- |
| 25 | 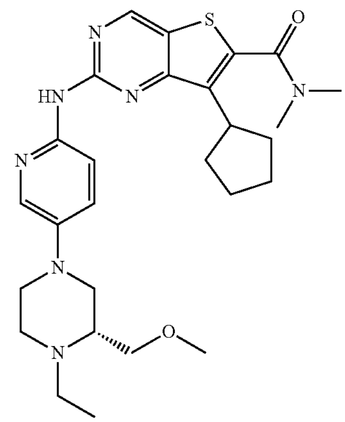 [SMILES: CCN1CCN(c2ccc(Nc3ncc4sc(C(=O)N(C)C)c(C5CCCC5)c4n3)nc2)C[C@@H]1COC] | (R)-7-cyclopentyl-2-((5-(4-ethyl-3-(methoxymethyl)piperazin-1-yl)pyridin-2-yl)amino)-N,N-dimethyl-thieno[3,2-d]pyrimidine-6-carboxamide | MS-ESI (m/z): 524 [M + 1]+ |
| 26 | 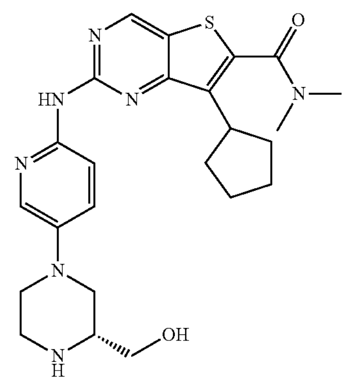 [SMILES: CN(C)C(=O)c1sc2cnc(Nc3ccc(N4CCN[C@@H](CO)C4)cn3)nc2c1C1CCCC1] | (R)-7-cyclopentyl-2-((5-(3-(hydroxymethyl)piperazin-1-yl)pyridin-2-yl)amino)-N,N-dimethylthieno[3,2-d]pyrimidine-6-carboxamide | MS-ESI (m/z): 482 [M + 1]+ |
| 27 | 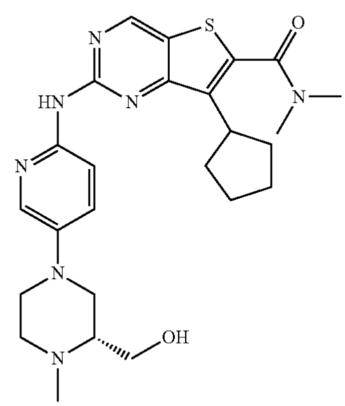 [SMILES: CN(C)C(=O)c1sc2cnc(Nc3ccc(N4CCN(C)[C@@H](CO)C4)cn3)nc2c1C1CCCC1] | (R)-7-cyclopentyl-2-((5-(3-(hydroxymethyl)-4-methylpiperazin-1-yl)pyridin-2-yl)amino)-N,N-dimethyl-thieno[3,2-d]pyrimidine-6-carboxamide | MS-ESI (m/z): 496 [M + 1]+ |
| 28 | 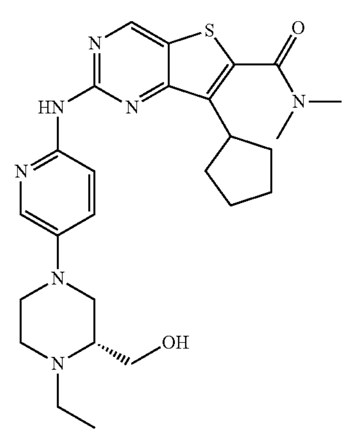 [SMILES: CCN1CCN(c2ccc(Nc3ncc4sc(C(=O)N(C)C)c(C5CCCC5)c4n3)nc2)C[C@@H]1CO] | (R)-7-cyclopentyl-2-((5-(4-ethyl-3-(hydroxymethyl)piperazin-1-yl)pyridin-2-yl)amino)-N,N-dimethyl-thieno[3,2-d]pyrimidine-6-carboxamide | MS-ESI (m/z): 510 [M + 1]+ |

TABLE 1-continued

| EXAMPLE | STRUCTURE | NAME | DATA |
|---|---|---|---|
| 29 | 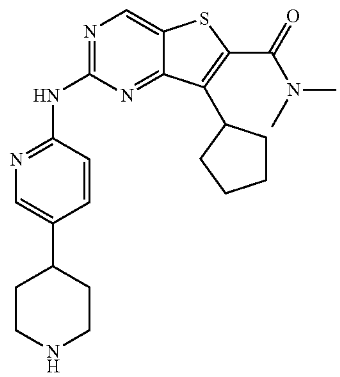 [SMILES: CN(C)C(=O)c1sc2cnc(Nc3ccc(C4CCNCC4)cn3)nc2c1C1CCCC1] | 7-cyclopentyl-N,N-dimethyl-2-((5-(piperidin-4-yl)pyridin-2-yl)amino)thieno[3,2-d]pyrimidine-6-carboxamide | MS-ESI (m/z): 451 [M + 1]+ |
| 30 | 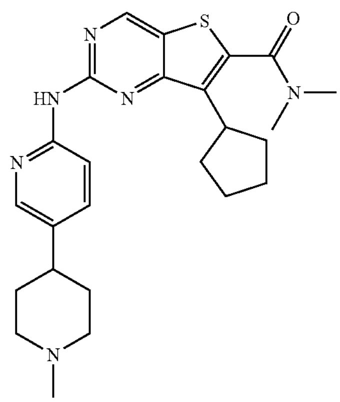 [SMILES: CN1CCC(c2ccc(Nc3ncc4sc(C(=O)N(C)C)c(C5CCCC5)c4n3)nc2)CC1] | 7-cyclopentyl-N,N-dimethyl-2-((5-(1-methylpiperidin-4-yl)pyridin-2-yl)amino)thieno[3,2-d]pyrimidine-6-carboxamide | MS-ESI (m/z): 465 [M + 1]+ |
| 31 | 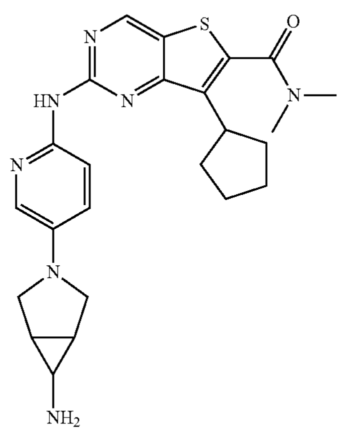 [SMILES: CN(C)C(=O)c1sc2cnc(Nc3ccc(N4CC5C(N)C5C4)cn3)nc2c1C1CCCC1] | 2-((5-(6-amino-3-azabicyclo[3.1.0]hexan-3-yl)pyridin-2-yl)amino)-7-cyclopentyl-N,N-dimethylthieno[3,2-d]pyrimidine-6-carboxamide | MS-ESI (m/z): 464 [M + 1]+ |
| 32 | 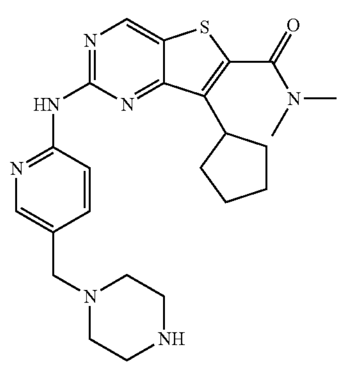 [SMILES: CN(C)C(=O)c1sc2cnc(Nc3ccc(CN4CCNCC4)cn3)nc2c1C1CCCC1] | 7-cyclopentyl-N,N-dimethyl-2-((5-(piperazin-1-ylmethyl)pyridin-2-yl)amino)thieno[3,2-d]pyrimidine-6-carboxamide | MS-ESI (m/z): 466 [M + 1]+ |

TABLE 1-continued

| EXAMPLE | STRUCTURE | NAME | DATA |
|---|---|---|---|
| 33 | 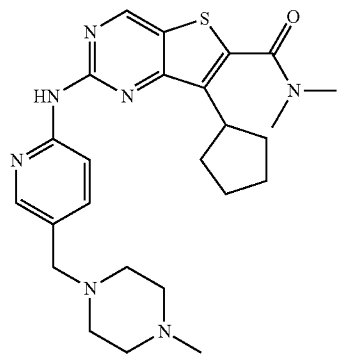 [SMILES: CN1CCN(Cc2ccc(Nc3ncc4sc(C(=O)N(C)C)c(C5CCCC5)c4n3)nc2)CC1] | 7-cyclopentyl-N,N-dimethyl-2-((5-((4-methylpiperazin-1-yl)methyl)pyridin-2-yl)amino)thieno[3,2-d]pyrimidine-6-carboxamide | MS-ESI (m/z): 480 [M + 1]$^+$ |
| 34 | 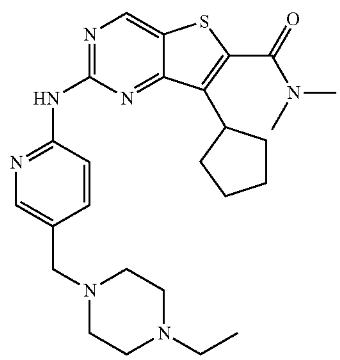 [SMILES: CCN1CCN(Cc2ccc(Nc3ncc4sc(C(=O)N(C)C)c(C5CCCC5)c4n3)nc2)CC1] | 7-cyclopentyl-2-((5-((4-ethylpiperazin-1-yl)methyl)pyridin-2-yl)amino)-N,N-dimethylthieno[3,2-d]pyrimidine-6-carboxamide | MS-ESI (m/z): 494 [M + 1]$^+$ |
| 35 | 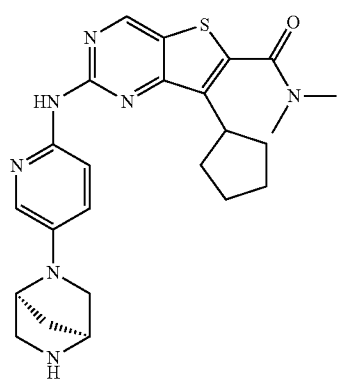 [SMILES: CN(C)C(=O)c1sc2cnc(Nc3ccc(N4C[C@@H]5C[C@H]4CN5)cn3)nc2c1C1CCCC1] | 2-((5-((1S,4S)-2,5-diazabicyclo[2.2.1]heptan-2-yl)pyridin-2-yl)amino)-7-cyclopentyl-N,N-dimethylthieno[3,2-d]pyrimidine-6-carboxamide | MS-ESI (m/z): 464 [M + 1]$^+$ |
| 36 | 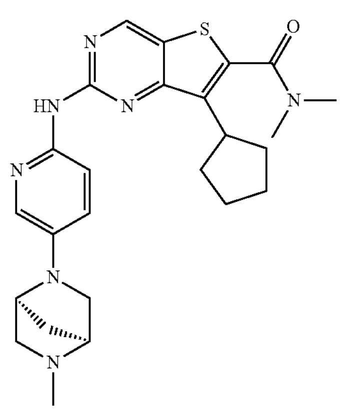 [SMILES: CN(C)C(=O)c1sc2cnc(Nc3ccc(N4C[C@@H]5C[C@H]4CN5C)cn3)nc2c1C1CCCC1] | 7-cyclopentyl-N,N-dimethyl-2-((5-((1S,4S)-5-methyl-2,5-diazabicyclo[2.2.1]heptan-2-yl)pyridin-2-yl)amino)thieno[3,2-d]pyrimidine-6-carboxamide | MS-ESI (m/z): 478 [M + 1]$^+$ |

TABLE 1-continued

| EXAMPLE | NAME | DATA |
|---|---|---|
| 37 | (R)-7-cyclopentyl-2-((5-(hexahydropyrrolo[1,2-a]pyrazin-2(1H)-yl)pyridin-2-yl)amino)-N,N-dimethylthieno[3,2-d]pyrimidine-6-carboxamide | MS-ESI (m/z): 492 [M + 1]$^+$ |
| 38 | (S)-7-cyclopentyl-2-((5-(hexahydropyrrolo[1,2-a]pyrazin-2(1H)-yl)pyridin-2-yl)amino)-N,N-dimethylthieno[3,2-d]pyrimidine-6-carboxamide | MS-ESI (m/z): 492 [M + 1]$^+$ |
| 39 | 2-((5-((1R,4R)-2,5-diazabicyclo[2.2.1]heptan-2-yl)pyridin-2-yl)amino)-7-cyclopentyl-N,N-dimethylthieno[3,2-d]pyrimidine-6-carboxamide | MS-ESI (m/z): 464 [M + 1]$^+$ |
| 40 | 2-((5-(3,6-diazabicyclo[3.1.1]heptan-3-yl)pyridin-2-yl)amino)-7-cyclopentyl-N,N-dimethylthieno[3,2-d]pyrimidine-6-carboxamide | MS-ESI (m/z): 464 [M + 1]$^+$ |

TABLE 1-continued

| EXAMPLE | STRUCTURE | NAME | DATA |
|---------|-----------|------|------|
| 41 | 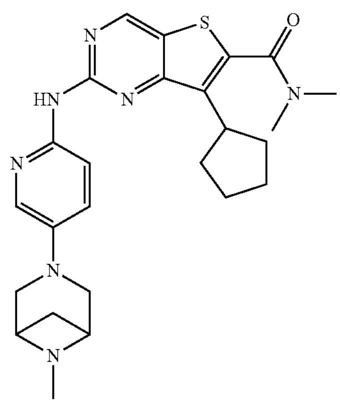 [SMILES: CN(C)C(=O)c1sc2cnc(Nc3ccc(N4CC5CC(C4)N5C)cn3)nc2c1C1CCCC1] | 7-cyclopentyl-N,N-dimethyl-2-((5-(6-methyl-3,6-diaza-bicyclo[3.1.1]heptan-3-yl)pyridin-2-yl)amino)thieno[3,2-d]pyrimidine-6-carboxamide | MS-ESI (m/z): 478 [M + 1]+ |
| 42 | 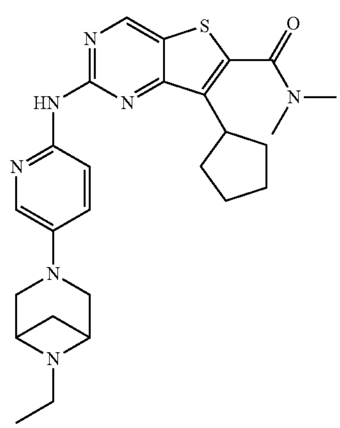 [SMILES: CCN1C2CC1CN(c1ccc(Nc3ncc4sc(C(=O)N(C)C)c(C5CCCC5)c4n3)nc1)C2] | 7-cyclopentyl-2-((5-(6-ethyl-3,6-diazabicyclo[3.1.1]heptan-3-yl)pyridin-2-yl)amino)-N,N-dimethylthieno[3,2-d]pyrimidine-6-carboxamide | MS-ESI (m/z): 492 [M + 1]+ |
| 43 | 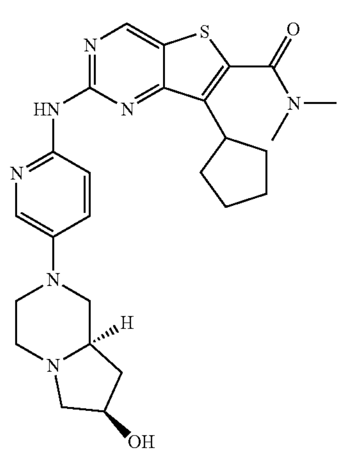 [SMILES: CN(C)C(=O)c1sc2cnc(Nc3ccc(N4CCN5C[C@H](O)C[C@@H]5C4)cn3)nc2c1C1CCCC1] | 7-cyclopentyl-2-((5-((7R,8aR)-7-hydroxyhexahydropyrrolo[1,2-a]pyrazin-2(1H)-yl)pyridin-2-yl)amino)-N,N-dimethylthieno[3,2-d]pyrimidine-6-carboxamide | MS-ESI (m/z): 508 [M + 1]+ |

TABLE 1-continued

| EXAMPLE | STRUCTURE | NAME | DATA |
|---|---|---|---|
| 44 | 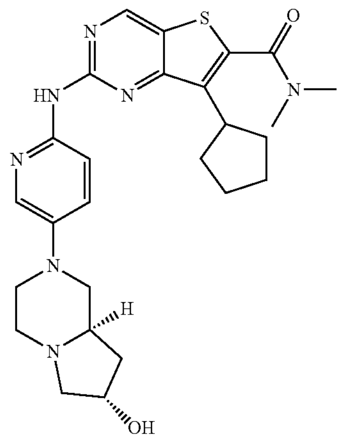 [SMILES: CN(C)C(=O)c1sc2cnc(Nc3ccc(N4CCN5C[C@@H](O)C[C@@H]5C4)cn3)nc2c1C1CCCC1] | 7-cyclopentyl-2-((5-((7S,8aR)-7-hydroxyhexahydro-pyrrolo[1,2-a]pyrazin-2(1H)-yl)pyridin-2-yl)amino)-N,N-dimethylthieno[3,2-d]pyrimidine-6-carboxamide | MS-ESI (m/z): 508 [M + 1]+ |
| 45 | 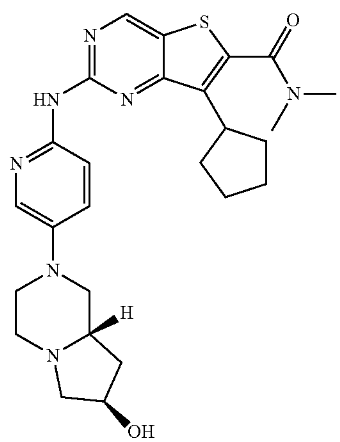 [SMILES: CN(C)C(=O)c1sc2cnc(Nc3ccc(N4CCN5C[C@H](O)C[C@H]5C4)cn3)nc2c1C1CCCC1] | 7-cyclopentyl-2-((5-((7R,8aS)-7-hydroxyhexahydro-pyrrolo[1,2-a]pyrazin-2(1H)-yl)pyridin-2-yl)amino)-N,N-dimethylthieno[3,2-d]pyrimidine-6-carboxamide | MS-ESI (m/z): 508 [M + 1]+ |
| 46 | 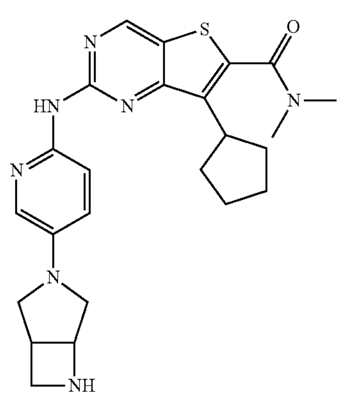 [SMILES: CN(C)C(=O)c1sc2cnc(Nc3ccc(N4CC5CNC5C4)cn3)nc2c1C1CCCC1] | 2-((5-(3,6-diazabicyclo[3.2.0]heptan-3-yl)pyridin-2-yl)amino)-7-cyclopentyl-N,N-dimethylthieno[3,2-d]pyrimidine-6-carboxamide | MS-ESI (m/z): 464 [M + 1]+ |

TABLE 1-continued

| EXAMPLE | STRUCTURE | NAME | DATA |
|---|---|---|---|
| 47 | 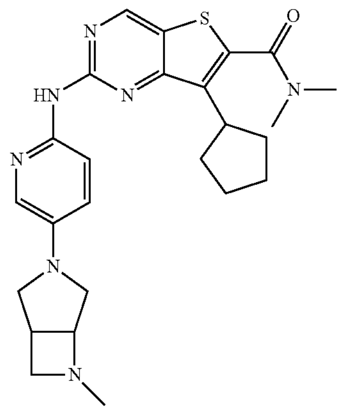 [SMILES: CN(C)C(=O)c1sc2cnc(Nc3ccc(N4CC5CN(C)C5C4)cn3)nc2c1C1CCCC1] | 7-cyclopentyl-N,N-dimethyl-2-((5-(6-methyl-3,6-diaza-bicyclo[3.2.0]heptan-3-yl)pyridin-2-yl)amino)thieno[3,2-d]pyrimidine-6-carboxamide | MS-ESI (m/z): 478 [M + 1]$^+$ |
| 48 | 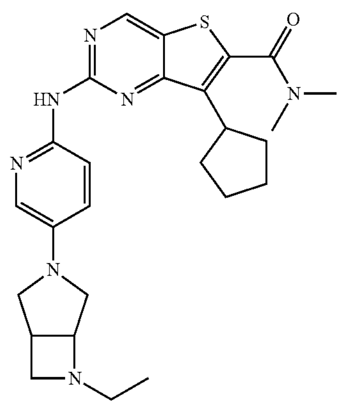 [SMILES: CCN1CC2CN(c3ccc(Nc4ncc5sc(C(=O)N(C)C)c(C6CCCC6)c5n4)nc3)CC21] | 7-cyclopentyl-2-((5-(6-ethyl-3,6-diazabicyclo[3.2.0]heptan-3-yl)pyridin-2-yl)amino)-N,N-dimethylthieno[3,2-d]pyrimidine-6-carboxamide | MS-ESI (m/z): 491 [M + 1]$^+$ |
| 49 | 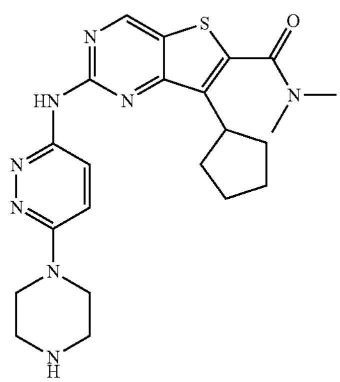 [SMILES: CN(C)C(=O)c1sc2cnc(Nc3ccc(N4CCNCC4)nn3)nc2c1C1CCCC1] | 7-cyclopentyl-N,N-dimethyl-2-((6-(piperazin-1-yl)pyridazin-3-yl)amino)thieno[3,2-d]pyrimidine-6-carboxamide | MS-ESI (m/z): 453 [M + 1]$^+$ |
| 50 | 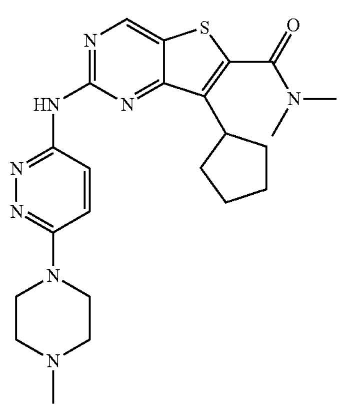 [SMILES: CN1CCN(c2ccc(Nc3ncc4sc(C(=O)N(C)C)c(C5CCCC5)c4n3)nn2)CC1] | 7-cyclopentyl-N,N-dimethyl-2-((6-(4-methylpiperazin-1-yl)pyridazin-3-yl)amino)thieno[3,2-d]pyrimidine-6-carboxamide | MS-ESI (m/z): 467 [M + 1]$^+$ |

TABLE 1-continued

| EXAMPLE | STRUCTURE | NAME | DATA |
|---|---|---|---|
| 51 | 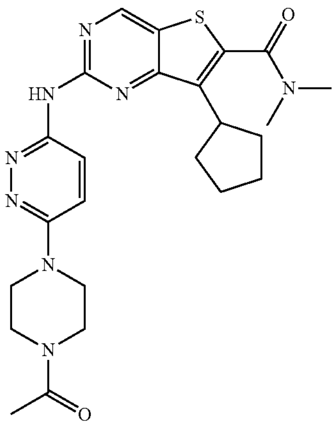 [SMILES: CC(=O)N1CCN(c2ccc(Nc3ncc4sc(C(=O)N(C)C)c(C5CCCC5)c4n3)nn2)CC1] | 2-((6-(4-acetylpiperazin-1-yl)pyridazin-3-yl)amino)-7-cyclopentyl-N,N-dimethylthieno[3,2-d]pyrimidine-6-carboxamide | MS-ESI (m/z): 495 [M + 1]$^+$ |
| 52 | 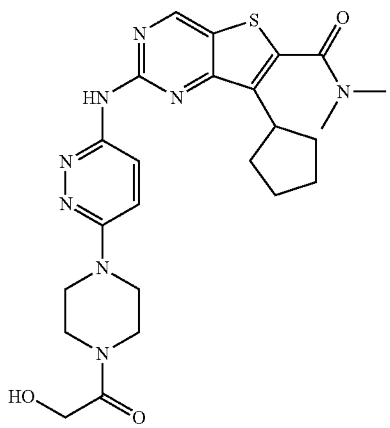 [SMILES: CN(C)C(=O)c1sc2cnc(Nc3ccc(N4CCN(C(=O)CO)CC4)nn3)nc2c1C1CCCC1] | 7-cyclopentyl-2-((6-(4-(2-hydroxyacetyl)piperazin-1-yl)pyridazin-3-yl)amino)-N,N-dimethylthieno[3,2-d]pyrimidine-6-carboxamide | MS-ESI (m/z): 511 [M + 1]$^+$ |
| 53 | 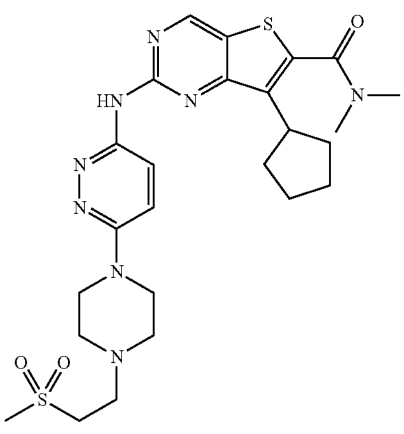 | 7-cyclopentyl-N,N-dimethyl-2-((6-(4-(2-(methylsulfonyl)ethyl)piperazin-1-yl)pyridazin-3-yl)amino)thieno[3,2-d]pyrimidine-6-carboxamide | MS-ESI (m/z): 559 [M + 1]$^+$ |
| 54 | 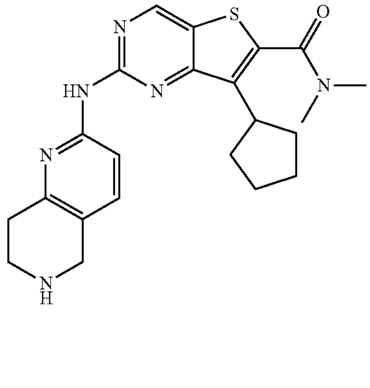 [SMILES: CN(C)C(=O)c1sc2cnc(Nc3ccc4c(n3)CCNC4)nc2c1C1CCCC1] | 7-cyclopentyl-N,N-dimethyl-2-((5,6,7,8-tetrahydro-1,6-naphthyridin-2-yl)amino)thieno[3,2-d]pyrimidine-6-carboxamide | MS-ESI (m/z): 423 [M + 1]$^+$ |

TABLE 1-continued

| EXAMPLE | STRUCTURE | NAME | DATA |
| --- | --- | --- | --- |
| 55 | 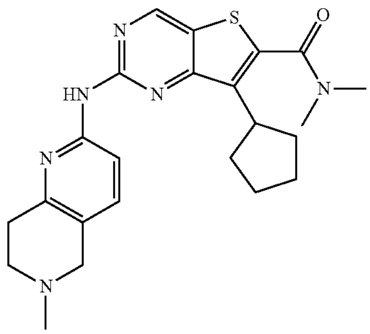 [SMILES: CN1CCc2nc(Nc3ncc4sc(C(=O)N(C)C)c(C5CCCC5)c4n3)ccc2C1] | 7-cyclopentyl-N,N-dimethyl-2-((6-methyl-5,6,7,8-tetrahydro-1,6-naphthyridin-2-yl)amino)thieno[3,2-d]pyrimidine-6-carboxamide | MS-ESI (m/z): 437 [M + 1]+ |
| 56 | 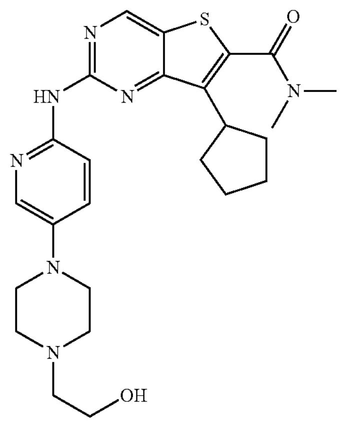 [SMILES: CN(C)C(=O)c1sc2cnc(Nc3ccc(N4CCN(CCO)CC4)cn3)nc2c1C1CCCC1] | 7-cyclopentyl-2-((5-(4-(2-hydroxyethyl)piperazin-1-yl)pyridin-2-yl)amino)-N,N-dimethylthieno[3,2-d]pyrimidine-6-carboxamide | MS-ESI (m/z): 496 [M + 1]+ |
| 57 | 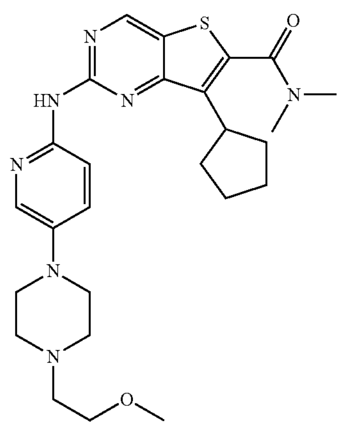 [SMILES: COCCN1CCN(c2ccc(Nc3ncc4sc(C(=O)N(C)C)c(C5CCCC5)c4n3)nc2)CC1] | 7-cyclopentyl-2-((5-(4-(2-methoxyethyl)piperazin-1-yl)pyridin-2-yl)amino)-N,N-dimethylthieno[3,2-d]pyrimidine-6-carboxamide | MS-ESI (m/z): 510 [M + 1]+ |
| 58 | 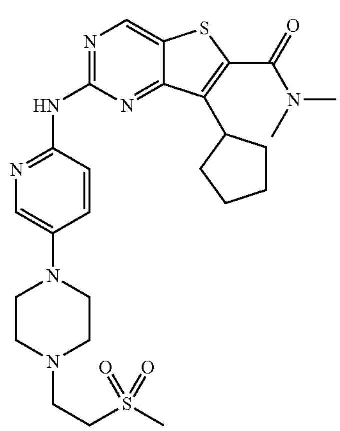 [SMILES: CN(C)C(=O)c1sc2cnc(Nc3ccc(N4CCN(CCS(C)(=O)=O)CC4)cn3)nc2c1C1CCCC1] | 7-cyclopentyl-N,N-dimethyl-2-((5-(4-(2-(methylsulfonyl)ethyl)piperazin-1-yl)pyridin-2-yl)amino)thieno[3,2-d]pyrimidine-6-carboxamide | MS-ESI (m/z): 558 [M + 1]+ |

TABLE 1-continued

| EXAMPLE | STRUCTURE | NAME | DATA |
|---|---|---|---|
| 59 | 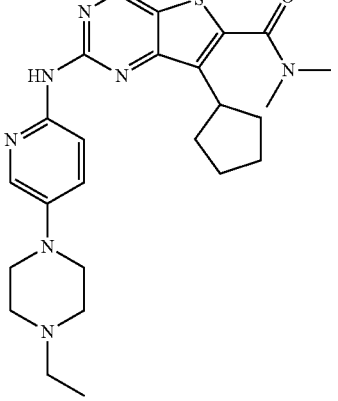 | 7-cyclopentyl-2-((5-(4-ethylpiperazin-1-yl)pyridin-2-yl)amino)-N,N-dimethylthieno[3,2-d]pyrimidine-6-carboxamide | MS-ESI (m/z): 480 [M + 1]$^+$ |
| 60 | 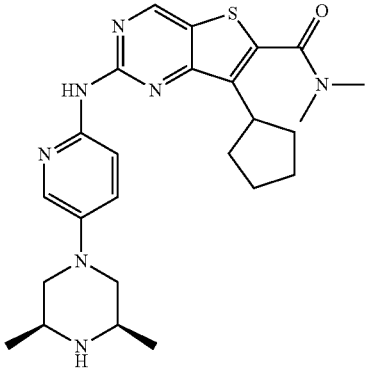 | 7-cyclopentyl-2-((5-((3S,5R)-3,5-dimethylpiperazin-1-yl)pyridin-2-yl)amino)-N,N-dimethylthieno[3,2-d]pyrimidine-6-carboxamide | MS-ESI (m/z): 480 [M + 1]$^+$ |
| 61 | 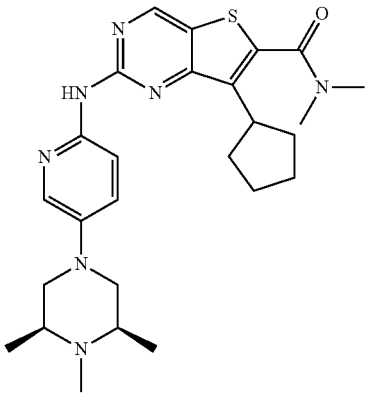 | 7-cyclopentyl-N,N-dimethyl-2-((5-((3S,5R)-3,4,5-trimethylpiperazin-1-yl)pyridin-2-yl)amino)thieno[3,2-d]pyrimidine-6-carboxamide | MS-ESI (m/z): 494 [M + 1]$^+$ |
| 62 | 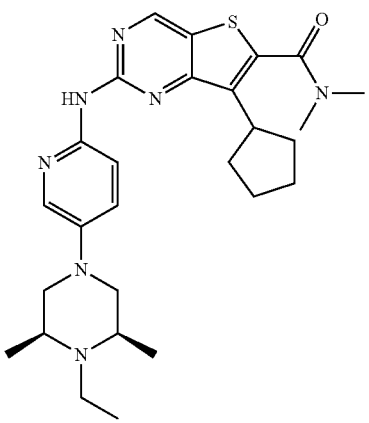 | 7-cyclopentyl-2-((5-((3S,5R)-4-ethyl-3,5-dimethylpiperazin-1-yl)pyridin-2-yl)amino)-N,N-dimethylthieno[3,2-d]pyrimidine-6-carboxamide | MS-ESI (m/z): 508 [M + 1]$^+$ |

TABLE 1-continued

| EXAMPLE | STRUCTURE | NAME | DATA |
|---|---|---|---|
| 63 | 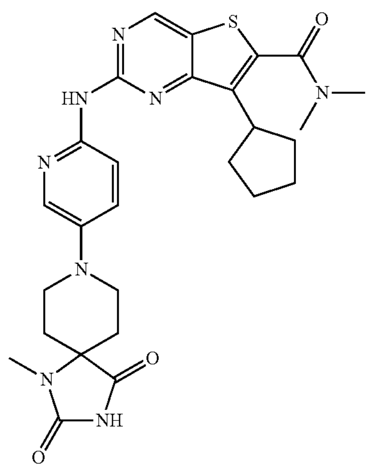 | 7-cyclopentyl-N,N-dimethyl-2-((5-(1-methyl-2,4-di-oxo-1,3,8-triazaspiro[4.5]decan-8-yl)pyridin-2-yl)amino)thieno[3,2-d]pyrimidine-6-carboxamide | MS-ESI (m/z): 549 [M + 1]+ |
| 64 | 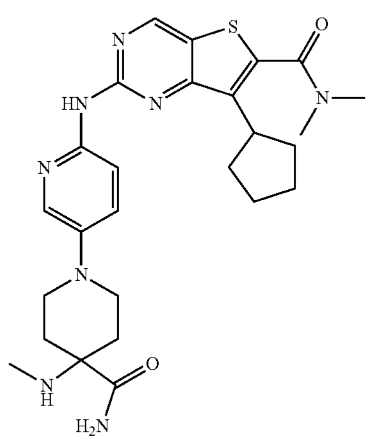 | 2-((5-(4-carbamoyl-4-(methylamino)piperidin-1-yl)pyridin-2-yl)amino)-7-cyclopentyl-N,N-dimethyl-thieno[3,2-d]pyrimidine-6-carboxamide | MS-ESI (m/z): 523 [M + 1]+ |

Examples 65-76 listed in Table 2 were prepared according to the method described for Example 1, by replacing dimethylamine hydrochloride with the corresponding amine, while Examples 77-84 were prepared according to the method described for Example 2. The structures and names of Examples 65-84 are given in Table 2.

TABLE 2

| EXAMPLE | STRUCTURE | NAME | DATA |
|---|---|---|---|
| 65 | 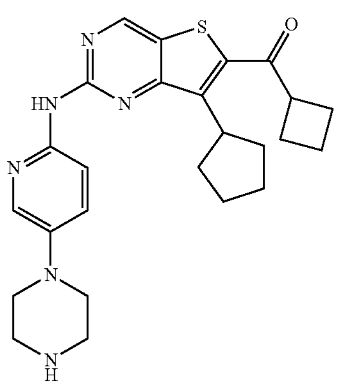 [SMILES: O=C(c1sc2cnc(Nc3ccc(N4CCNCC4)cn3)nc2c1C1CCCC1)C1CCC1] | azetidin-1-yl(7-cyclopentyl-2-((5-(piperazin-1-yl)pyridin-2-yl)amino)thieno[3,2-d]pyrimidin-6-yl)methanone | MS-ESI (m/z): 464 [M + 1]+ |

TABLE 2-continued

| EXAMPLE | STRUCTURE | NAME | DATA |
|---|---|---|---|
| 66 | 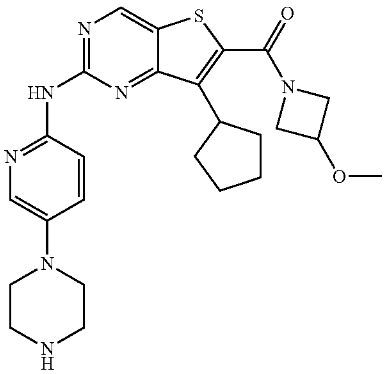 [SMILES: COC1CN(C(=O)c2sc3cnc(Nc4ccc(N5CCNCC5)cn4)nc3c2C2CCCC2)C1] | (7-cyclopentyl-2-((5-(piperazin-1-yl)pyridin-2-yl)amino)thieno[3,2-d]pyrimidin-6-yl)(3-methoxyazetidin-1-yl)methanone | MS-ESI (m/z): 494 [M + 1]+ |
| 67 | 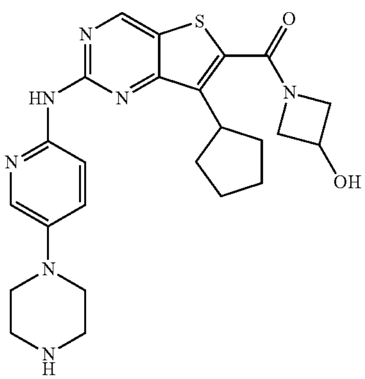 [SMILES: O=C(c1sc2cnc(Nc3ccc(N4CCNCC4)cn3)nc2c1C1CCCC1)N1CC(O)C1] | (7-cyclopentyl-2-((5-(piperazin-1-yl)pyridin-2-yl)amino)thieno[3,2-d]pyrimidin-6-yl)(3-hydroxyazetidin-1-yl)methanone | MS-ESI (m/z): 480 [M + 1]+ |
| 68 | 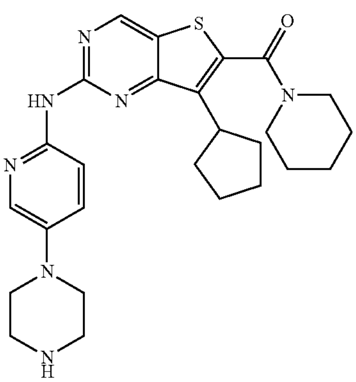 [SMILES: O=C(c1sc2cnc(Nc3ccc(N4CCNCC4)cn3)nc2c1C1CCCC1)N1CCCCC1] | (7-cyclopentyl-2-((5-(piperazin-1-yl)pyridin-2-yl)amino)thieno[3,2-d]pyrimidin-6-yl)(piperidin-1-yl)methanone | MS-ESI (m/z): 492 [M + 1]+ |
| 69 | 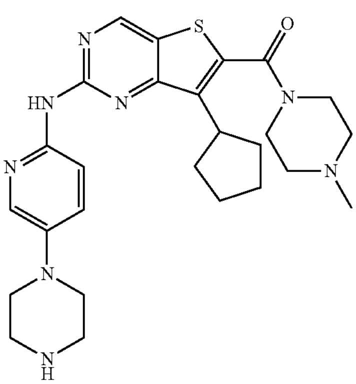 [SMILES: CN1CCN(C(=O)c2sc3cnc(Nc4ccc(N5CCNCC5)cn4)nc3c2C2CCCC2)CC1] | (7-cyclopentyl-2-((5-(piperazin-1-yl)pyridin-2-yl)amino)thieno[3,2-d]pyrimidin-6-yl)(4-methylpiperaizn-1-yl)methanone | MS-ESI (m/z): 507 [M + 1]+ |

TABLE 2-continued

| EXAMPLE | STRUCTURE | NAME | DATA |
| --- | --- | --- | --- |
| 70 | 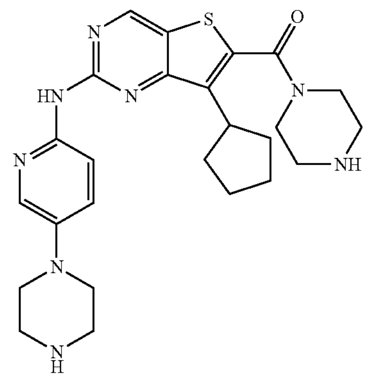 [SMILES: O=C(c1sc2cnc(Nc3ccc(N4CCNCC4)cn3)nc2c1C1CCCC1)N1CCNCC1] | (7-cyclopentyl-2-((5-(piperazin-1-yl)pyridin-2-yl)amino)thieno[3,2-d]pyrimidin-6-yl)(piperazin-1-yl)methanone | MS-ESI (m/z): 493 [M + 1]$^+$ |
| 71 | 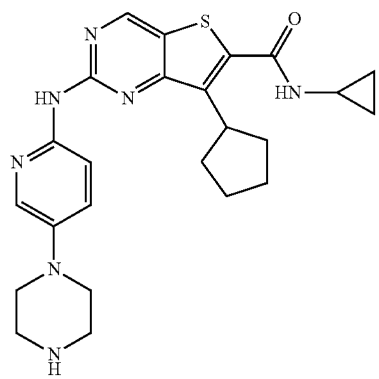 [SMILES: O=C(NC1CC1)c1sc2cnc(Nc3ccc(N4CCNCC4)cn3)nc2c1C1CCCC1] | 7-cyclopentyl-N-cyclopropyl-2-((5-(piperazin-1-yl)pyridin-2-yl)amino)thieno[3,2-d]pyrimidine-6-carboxamide | MS-ESI (m/z): 464 [M + 1]$^+$ |
| 72 | 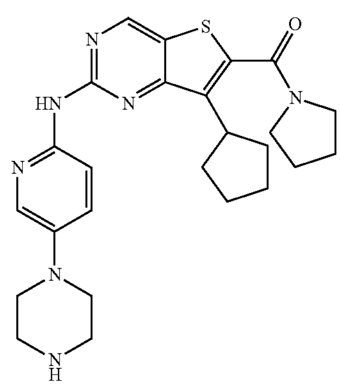 [SMILES: O=C(c1sc2cnc(Nc3ccc(N4CCNCC4)cn3)nc2c1C1CCCC1)N1CCCC1] | (7-cyclopentyl-2-((5-(piperazin-1-yl)pyridin-2-yl)amino)thieno[3,2-d]pyrimidin-6-yl)(pyrrolidin-1-yl)methanone | MS-ESI (m/z): 478 [M + 1]$^+$ |
| 73 | 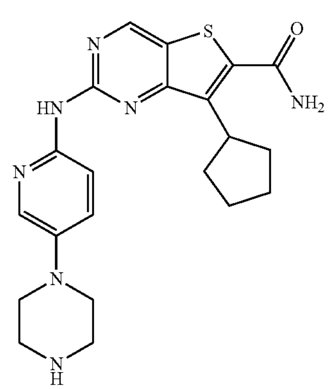 [SMILES: NC(=O)c1sc2cnc(Nc3ccc(N4CCNCC4)cn3)nc2c1C1CCCC1] | 7-cyclopentyl-2-((5-(piperazin-1-yl)pyridin-2-yl)amino)thieno[3,2-d]pyrimidine-6-carboxamide | MS-ESI (m/z): 424 [M + 1]$^+$ |

TABLE 2-continued

| EXAMPLE | STRUCTURE | NAME | DATA |
|---|---|---|---|
| 74 | 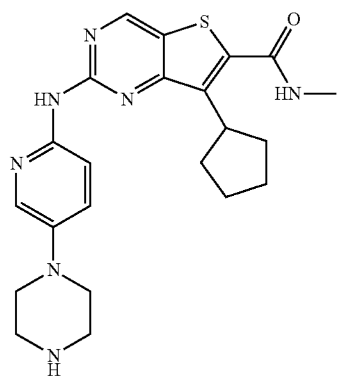 [SMILES: CNC(=O)c1sc2cnc(Nc3ccc(N4CCNCC4)cn3)nc2c1C1CCCC1] | 7-cyclopentyl-N-methyl-2-((5-(piperazin-1-yl)pyridin-2-yl)amino)thieno[3,2-d]pyrimidine-6-carboxamide | MS-ESI (m/z): 438 [M + 1]⁺ |
| 75 | 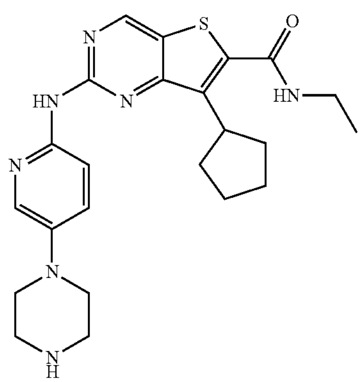 [SMILES: CCNC(=O)c1sc2cnc(Nc3ccc(N4CCNCC4)cn3)nc2c1C1CCCC1] | 7-cyclopentyl-N-ethyl-2-((5-(piperazin-1-yl)pyridin-2-yl)amino)thieno[3,2-d]pyrimidine-6-carboxamide | MS-ESI (m/z): 452 [M + 1]⁺ |
| 76 | 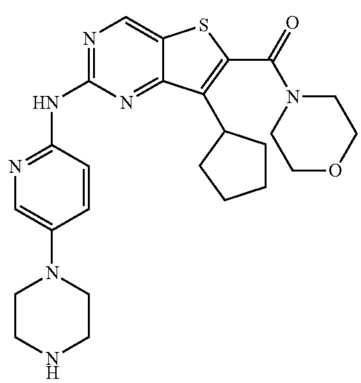 [SMILES: O=C(c1sc2cnc(Nc3ccc(N4CCNCC4)cn3)nc2c1C1CCCC1)N1CCOCC1] | (7-cyclopentyl-2-((5-(piperazin-1-yl)pyridin-2-yl)amino)thieno[3,2-d]pyrimidin-6-yl)(morpholino)methanone | MS-ESI (m/z): 494 [M + 1]⁺ |
| 77 | 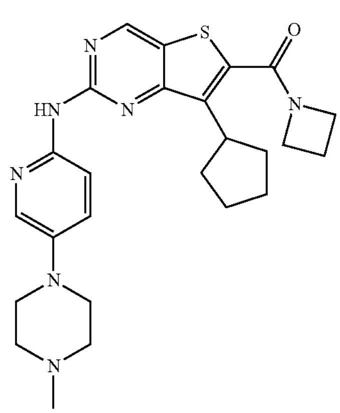 [SMILES: CN1CCN(c2ccc(Nc3ncc4sc(C(=O)N5CCC5)c(C5CCCC5)c4n3)nc2)CC1] | azetidin-1-yl(7-cyclopentyl-2-((5-(4-methylpiperazin-1-yl)pyridin-2-yl)amino)thieno[3,2-d]pyrimidin-6-yl)methanone | MS-ESI (m/z): 478 [M + 1]⁺ |

TABLE 2-continued

| EXAMPLE | STRUCTURE | NAME | DATA |
|---|---|---|---|
| 78 | 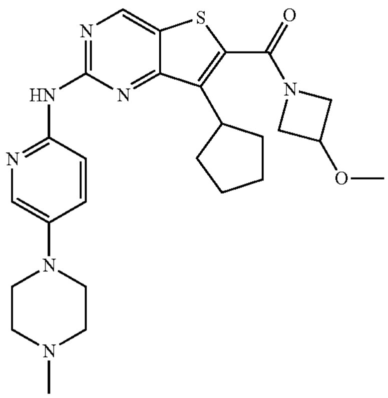 [SMILES: COC1CN(C(=O)c2sc3cnc(Nc4ccc(N5CCN(C)CC5)cn4)nc3c2C2CCCC2)C1] | (7-cyclopentyl-2-((5-(4-methylpiperazin-1-yl)pyridin-2-yl)amino)thieno[3,2-d]pyrimidin-6-yl)(3-methoxy-azetidin-1-yl)methanone | MS-ESI (m/z): 508 [M + 1]+ |
| 79 | 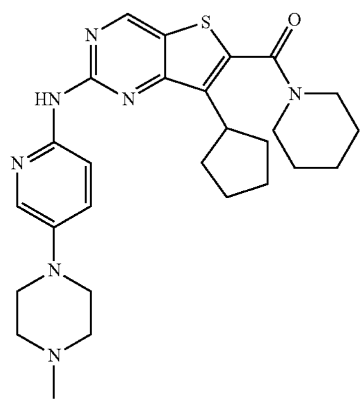 [SMILES: CN1CCN(c2ccc(Nc3ncc4sc(C(=O)N5CCCCC5)c(C5CCCC5)c4n3)nc2)CC1] | (7-cyclopentyl-2-((5-(4-methylpiperazin-1-yl)pyridin-2-yl)amino)thieno[3,2-d]pyrimidin-6-yl)(piperidin-1-yl)methanone | MS-ESI (m/z): 506 [M + 1]+ |
| 80 | 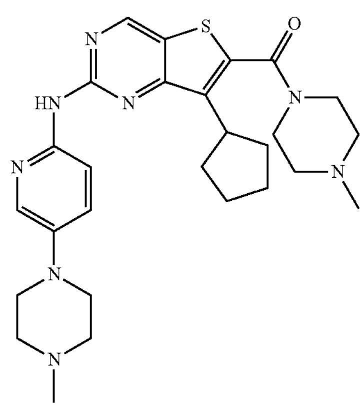 [SMILES: CN1CCN(C(=O)c2sc3cnc(Nc4ccc(N5CCN(C)CC5)cn4)nc3c2C2CCCC2)CC1] | (7-cyclopentyl-2-((5-(4-methylpiperazin-1-yl)pyridin-2-yl)amino)thieno[3,2-d]pyrimidin-6-yl)(4-methylpiperazin-1-yl)methanone | MS-ESI (m/z): 521 [M + 1]+ |
| 81 | 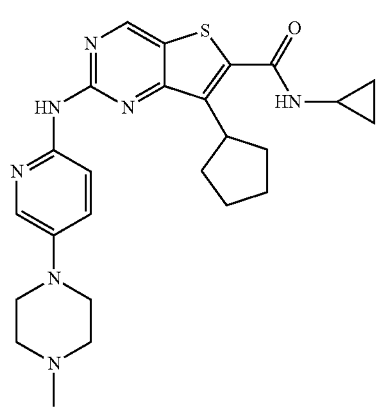 [SMILES: CN1CCN(c2ccc(Nc3ncc4sc(C(=O)NC5CC5)c(C5CCCC5)c4n3)nc2)CC1] | 7-cyclopentyl-N-cyclopropyl-2-((5-(4-methylpiperazin-1-yl)pyridin-2-yl)amino)thieno[3,2-d]pyrimidine-6-carboxamide | MS-ESI (m/z): 478 [M + 1]+ |

TABLE 2-continued

| EXAMPLE | STRUCTURE | NAME | DATA |
|---|---|---|---|
| 82 | 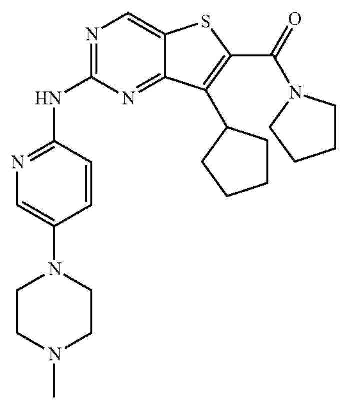 [SMILES: CN1CCN(c2ccc(Nc3ncc4sc(C(=O)N5CCCC5)c(C5CCCC5)c4n3)nc2)CC1] | (7-cyclopentyl-2-((5-(4-methylpiperazin-1-yl)pyridin-2-yl)amino)thieno[3,2-d]pyrimidin-6-yl)(pyrrolidin-1-yl)methanone | MS-ESI (m/z): 492 [M + 1]+ |
| 83 | 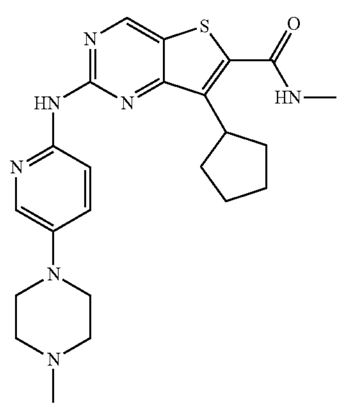 [SMILES: CNC(=O)c1sc2cnc(Nc3ccc(N4CCN(C)CC4)cn3)nc2c1C1CCCC1] | 7-cyclopentyl-N-methyl-2-((5-(4-methylpiperazin-1-yl)pyridin-2-yl)amino)thieno[3,2-d]pyrimidine-6-carboxamide | MS-ESI (m/z): 452 [M + 1]+ |
| 84 | 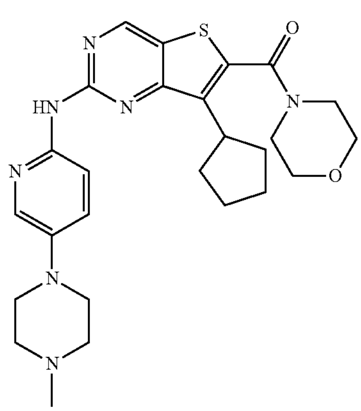 [SMILES: CN1CCN(c2ccc(Nc3ncc4sc(C(=O)N5CCOCC5)c(C5CCCC5)c4n3)nc2)CC1] | (7-cyclopentyl-2-((5-(4-methylpiperazin-1-yl)pyridin-2-yl)amino)thieno[3,2-d]pyrimidin-6-yl)(morpholino)methanone | MS-ESI (m/z): 508 [M + 1]+ |

Example 85

N,N-dimethyl-7-((1r,4r)-4-methylcyclohexyl)-2-((5-(piperazin-1-yl)pyridin-2-yl)amino)thieno[3,2-d]pyrimidine-6-carboxamide (85)

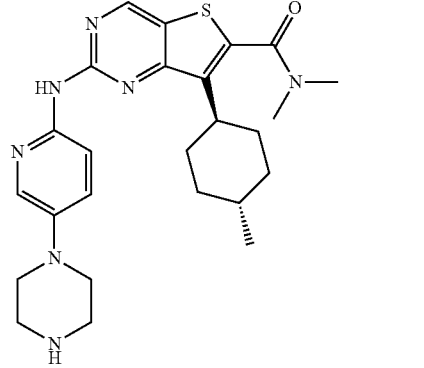

The title compound (Example 85) (10 mg, 98%) was prepared by using the same procedure as described for Example 1 by replacing cyclopentanecarbaldehyde with (1r,4r)-4-methylcyclohexane-1-carbaldehyde. MS-ESI (m/z): 480 [M+1]$^+$.

Following essentially the same procedures outlined for Examples 85, Examples 86-94 listed in Table 3 were prepared by replacing tert-butyl 4-(6-formamidopyridin-3-yl)piperazine-1-carboxylate with the corresponding aminopyridines or aminopyridazines and sequential modifications as necessary, such as acylation and

TABLE 3

| EXAMPLE | STRUCTURE | NAME | DATA |
|---|---|---|---|
| 86 | 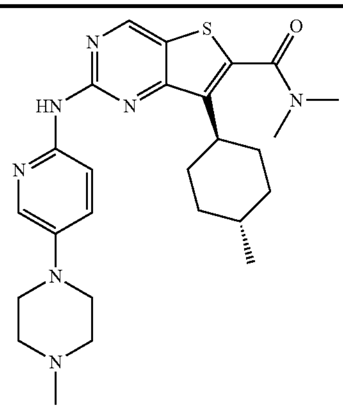 | N,N-dimethyl-7-((1r,4r)-4-methylcyclohexyl)-2-((5-(4-methylpiperazin-1-yl)pyridin-2-yl)amino)thieno[3,2-d]pyrimidine-6-carboxamide | MS-ESI (m/z): 494 [M + 1]$^+$ |
| 87 | 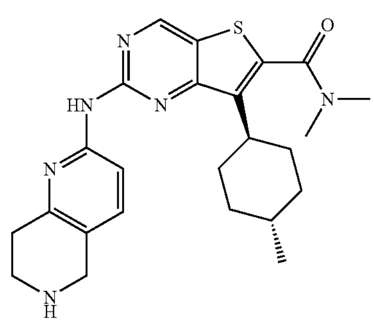 [SMILES: CN(C)C(=O)c1sc2cnc(Nc3ccc4c(n3)CCNC4)nc2c1[C@H]1CC[C@H](C)CC1] | N,N-dimethyl-7-((1r,4r)-4-methylcyclohexyl)-2-((5,6,7,8-tetrahydro-1,6-naphthyridin-2-yl)amino)thieno[3,2-d]pyrimidine-6-carboxamide | MS-ESI (m/z): 451 [M + 1]$^+$ |
| 88 | 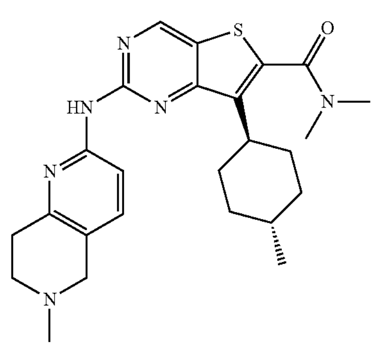 [SMILES: CN1CCc2nc(Nc3ncc4sc(C(=O)N(C)C)c([C@H]5CC[C@H](C)CC5)c4n3)ccc2C1] | N,N-dimethyl-2-((6-methyl-5,6,7,8-tetrahydro-1,6-naphthyridin-2-yl)amino)-7-((1r,4r)-4-methylcyclohexyl)thieno[3,2-d]pyrimidine-6-carboxamide | MS-ESI (m/z): 465 [M + 1]$^+$ |

TABLE 3-continued

| EXAMPLE | STRUCTURE | NAME | DATA |
|---|---|---|---|
| 89 | 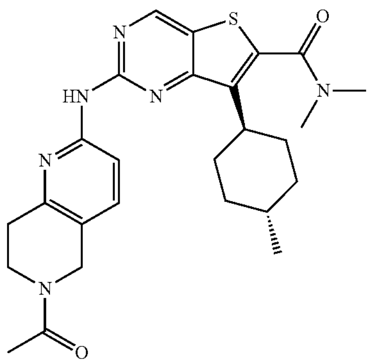 [SMILES: CC(=O)N1CCc2nc(Nc3ncc4sc(C(=O)N(C)C)c([C@H]5CC[C@H](C)CC5)c4n3)ccc2C1] | 2-((6-acetyl-5,6,7,8-tetrahydro-1,6-naphthyridin-2-yl)amino)-N,N-dimethyl-7-((1r,4r)-4-methylcyclohexyl)thieno[3,2-d]pyrimidine-6-carboxamide | MS-ESI (m/z): 493 [M + 1]+ |
| 90 | 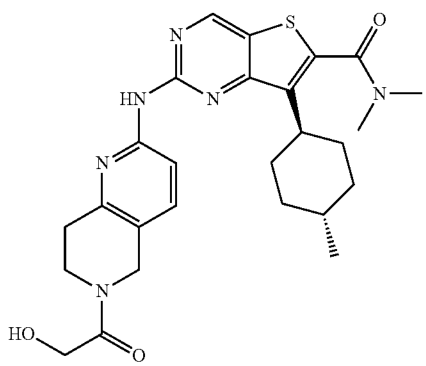 [SMILES: CN(C)C(=O)c1sc2cnc(Nc3ccc4c(n3)CCN(C(=O)CO)C4)nc2c1[C@H]1CC[C@H](C)CC1] | 2-((6-(2-hydroxyacetyl)-5,6,7,8-tetrahydro-1,6-naphthyridin-2-yl)amino)-N,N-dimethyl-7-((1r,4r)-4-methylcyclohexyl)thieno[3,2-d]pyrimidine-6-carboxamide | MS-ESI (m/z): 509 [M + 1]+ |
| 91 | 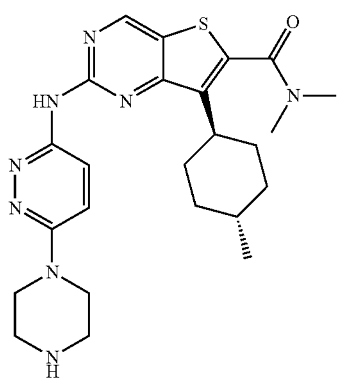 [SMILES: CN(C)C(=O)c1sc2cnc(Nc3ccc(N4CCNCC4)nn3)nc2c1[C@H]1CC[C@H](C)CC1] | N,N-dimethyl-7-((1r,4r)-4-methylcyclohexyl)-2-((6-(piperazin-1-yl)pyridazin-3-yl)amino)thieno[3,2-d]pyrimidine-6-carboxamide | MS-ESI (m/z): 481 [M + 1]+ |
| 92 | 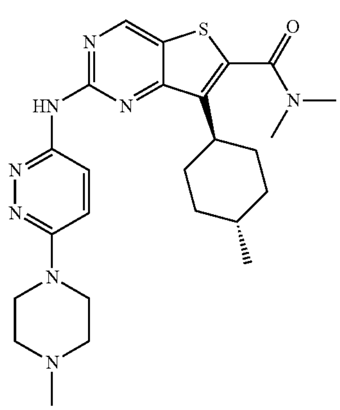 [SMILES: CN1CCN(c2ccc(Nc3ncc4sc(C(=O)N(C)C)c([C@H]5CC[C@H](C)CC5)c4n3)nn2)CC1] | N,N-dimethyl-7-((1r,4r)-4-methylcyclohexyl)-2-((6-(4-methylpiperazin-1-yl)pyridazin-3-yl)amino)thieno[3,2-d]pyrimidine-6-carboxamide | MS-ESI (m/z): 495 [M + 1]+ |

TABLE 3-continued

| EXAMPLE | STRUCTURE | NAME | DATA |
|---|---|---|---|
| 93 | 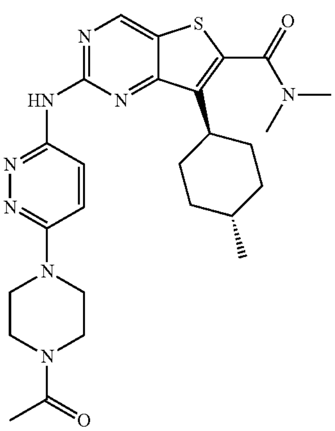 [SMILES: CC(=O)N1CCN(c2ccc(Nc3ncc4sc(C(=O)N(C)C)c([C@H]5CC[C@H](C)CC5)c4n3)nn2)CC1] | 2-((6-(4-acetylpiperazin-1-yl)pyridazin-3-yl)amino)-N,N-dimethyl-7-((1r,4r)-4-methylcylcohexyl)thieno[3,2-d]pyrimidine-6-carboxamide | MS-ESI (m/z): 523 [M + 1]⁺ |
| 94 | 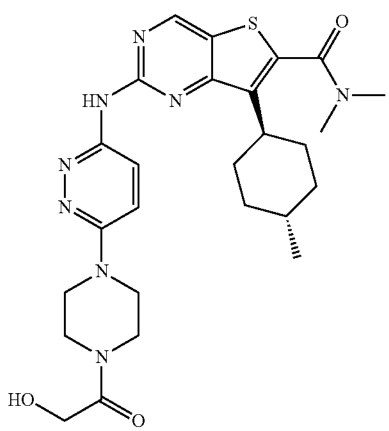 [SMILES: CN(C)C(=O)c1sc2cnc(Nc3ccc(N4CCN(C(=O)CO)CC4)nn3)nc2c1[C@H]1CC[C@H](C)CC1] | 2-((6-(4-(2-hydroxyacetyl)piperazin-1-yl)pyridazin-3-yl)amino)-N,N-dimethyl-7-((1r,4r)-4-methyl-cyclohexyl)thieno[3,2-d]pyrimidine-6-carboxamide | MS-ESI (m/z): 539 [M + 1]⁺ |

Cell Proliferation Assays

To investigate whether a compound is able to inhibit the activity of CDK4/6 in cells, a mechanism-based assay using COLO-205 cell was developed. In this assay, inhibition of CDK4/6 was detected by the inhibition of COLO-205 cells proliferation. COLO-205 cells were cultured in culture flasks to 40-80% confluence in RPMI-1640 plus 10% fetal bovine serum. Cells were collected and plated onto 96-well plates at desired cell density (2000 cells/well). Plates were incubated overnight at 37° C., with 5% $CO_2$ to adhere. Compounds were added to the plates, the final compound concentrations were 10000, 3333.3, 1111.1, 270.4, 123.5, 41.2, 13.7, 4.6 and 1.5 nM. Place plates at 37° C., with 5% $CO_2$ for 48 h. After removing the medium, 20 μl MTS/100 μl medium mixture solution were added to each well and incubate the plates for exactly 1.5 hours. Stop the reaction by adding 25 μl 10% SDS per well. Measure absorbance at 490 nm and 650 nm (reference wavelength). $IC_{50}$ was calculated using GraphPad Prism 5.0.

BE(2)-C Cells were plated in 96-well plates with 150 μl culture medium at cell density of 5000 cells/well. Compounds dilution: 20 mM stock solution of all compounds in DMSO. On the day of treatment, compounds were fresh diluted from the stock solution to a working solution (4× of final concentrations) in culture medium. 50 μl of compound mixtures were added to duplicate wells along with 150 μl of cells. 24 hours after BE(2)-C cells were plated, testing compounds were added. Cell proliferation was measured by MTS assay following manufacturer's instruction after compound treatment for 72 hours.

Select compounds prepared as described above were assayed according to the biological procedures described herein. The results are given in Table 4.

TABLE 4

| Example | COLO205 $IC_{50}$ (nM) | BE(2)-C $IC_{50}$ (nM) |
|---|---|---|
| 1 | 1106 | 38.5 |
| 2 | 339 | 24.1 |
| 5 | 517 | 601 |
| 7 | 711 | / |
| 73 | 624 | / |
| 87 | 450 | |
| 88 | 855 | / |
| 89 | 389 | / |
| 90 | 270 | |
| 91 | 223 | / |

What is claimed is:

1. A compound of formula (I):

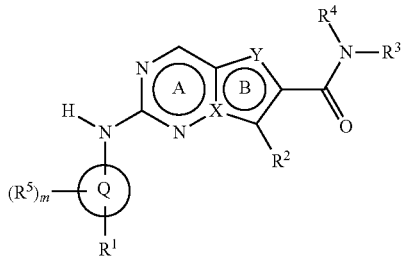

or a pharmaceutically acceptable salt thereof, wherein:
X is C;
Y is S;
6-5 membered fused ring system A-B is

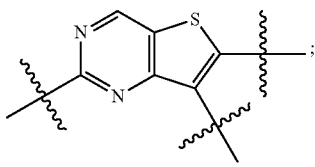 [SMILES: *c1ncc2sc(*)c(*)c2n1]

Q is selected from aryl and heteroaryl;
$R^1$ is selected from: hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, and heterocyclyl are each unsubstituted or substituted with at least one substituent independently selected from $R^{6a}$, and wherein aryl and heteroaryl are each unsubstituted or substituted with at least one substituent independently selected from $R^{6b}$;
$R^2$ is selected from: hydrogen, halogen, hydroxyl, CN, $C_{1-10}$ alkyl, C2-10 alkenyl, C2-10 alkynyl, $C_3$-10 cycloalkyl, C3-10 cycloalkyl-$C_{14}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, and heterocyclyl are each unsubstituted or substituted with at least one substituent, independently selected from $R^{6a}$, and each aryl and heteroaryl is unsubstituted or substituted with at least one substituent independently selected from $R^{6b}$;
$R^3$ and $R^4$ are independently selected from: hydrogen, $C_{1-10}$ alkyl, C2-10 alkenyl, C2-10 alkynyl, and C3-10 cycloalkyl; wherein alkyl, alkenyl, alkynyl, and cycloalkyl are each unsubstituted or substituted with at least one substituent independently selected from $R^{6a}$; or $R^3$ and $R^4$ together with the nitrogen atoms to which they are attached form a 4-12 membered ring containing 0, 1, 2 or 3 heteroatoms independently selected from oxygen, sulfur and nitrogen, and optionally substituted with for 1 or 2 $R^{6a}$ groups;
with the proviso that when $R^3$ and $R^4$ are both hydrogen, $R^2$ is not aryl or heteroaryl;
each $R^5$ is independently selected from: hydrogen, $C_{1-10}$ alkyl, $C_{2-10}$ alkenyl, $C_{2-10}$ alkynyl, $C_{3-10}$ cycloalkyl, —$OR^8$, —$NR^7S(O)_rR^8$, —$NO_2$, -halogen, —$S(O)_rR^7$, —$SR^8$, —$S(O)_2OR^7$, —$OS(O)_2R^8$, —$S(O)NR^7R^8$, —$NR^7R^8$, —$O(CR^9R^{10})_rNR^7R^8$, —$C(O)R^7$, —$CO_2R^8$, —$CO_2(CR^9R^{10})_rCONR^7R^8$, —$OC(O)R^7$, —CN, —$C(O)NR^7R^8$, —$NR^7C(O)R^8$, —$OC(O)NR^7R^8$, —$NR^7C(O)OR^8$, —$NR^7C(O)NR^7R^8$, —$CR^7(N-OR^8)$, —$CHF_2$, —$CF_3$, —$OCHF_2$, and —$OCF_3$; wherein $C_{1-10}$ alkyl, $C_{2-10}$ alkenyl, $C_{2-10}$ alkynyl, and $C_{3-10}$ cycloalkyl are each unsubstituted or substituted with at least one substituent independently selected from $R^{6a}$;
each $R^{6a}$ is independently selected from: -$C_{1-10}$ alkyl, -$C_{2-10}$ alkenyl, -$C_{2-10}$ alkynyl, -$C_{3-10}$ cycloalkyl, —$OR^8$, —$NR^7S(O)_rR^8$, —$NO_2$, -halogen, —$S(O)_rR^7$, —$SR_8$, —$S(O)_2OR^7$, —$OS(O)_2R^8$, —$S(O)_rNR^7R^8$, —$NR^7R^8$, —$(CR^9R^{10})_rOR^8$, —$(CR^9R^{10})_rNR^7R^8$, —$(CR^9R^{10})_rSR^8$, —$(CR^9R^{10})_rS(O)_rR^8$, —$(CR^9R^{10})_rCO_2R^8$, —$(CR^9R^{10})_rCONR^7R^8$, —$(CR^9R^{10})_rNR^7CO_2R^8$, —$(CR^9R^{10})_rOCONR^7R^8$, —$(CR^9R^{10})_rNR^7CONR^7R^8$, —$(CR^9R^{10})_rNR^7SO_2NR^7R^8$, —$O(CR^9R^{10})_rNR^7R^8$, —$C(O)R^7$, —$C(O)(CR^9R^{10})_rOR^8$, —$C(O)(CR^9R^{10})_rNR^7R^8$, —$C(O)(CR^9R^{10})_rSR^8$, —$C(O)(CR^9R^{10})_rS(O)_rR^8$, —$CO_2R^8$, —$CO_2(CR^9R^{10})_rCONR^7R^8$, —$OC(O)R^7$, —CN, —$C(O)NR^7R^8$, —$NR^7C(O)R^8$, —$OC(O)NR^7R^8$, —$NR^7C(O)OR^8$, —$NR^7C(O)NR^7R^8$, —$CR^7(N—OR^8)$, —$CHF_2$, —$CF_3$, —$OCHF_2$, and —$OCF_3$;
each $R^{6b}$ is independently selected from: $R^{6a}$, aryl, aryl-$C_{1-4}$ alkyl, heteroaryl, and heteroaryl-$C_{1-4}$ alkyl;
each $R^7$ and each $R^8$ are independently selected from: hydrogen, $C_{1-10}$ alkyl, $C_{2-10}$ alkenyl, $C_{2-10}$ alkynyl, cycloalkyl, cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl; wherein alkyl, alkenyl, alkynyl, cycloalkyl, and heterocyclyl are each unsubstituted or substituted with at least one substituent, independently selected from $R^{6a}$, and aryl and heteroaryl are each unsubstituted or substituted with at least one substituent independently selected from $R^{6b}$; or $R^7$ and $R^8$ together with the atom(s) to which they are attached form a heterocyclic ring of 4 to 12 members containing 0, 1, or 2 additional heteroatoms independently selected from oxygen, sulfur and nitrogen, and optionally substituted with 1 or 2 $R^{6b}$ groups;
each $R^9$ and each $R^{10}$ are independently selected from: hydrogen, $C_{1-10}$, $C_{2-10}$ alkenyl, $C_{2-10}$ alkynyl, cycloalkyl, cycloalkyl-C1-4 alkyl, heterocyclyl, heterocyclyl-C1-4 alkyl, aryl, aryl-C1-4 alkyl, heteroaryl, and heteroaryl-$C_{1-4}$ alkyl; or $R^9$ and $R^{10}$ together with the carbon atom(s) to which they are attached form a ring of 3 to 7 members containing 0, 1, or 2 heteroatoms independently selected from oxygen, sulfur and nitrogen, and optionally substituted with 1 or 2 $R^{6a}$ groups;
m is independently selected from 0, 1, 2, and 3;
each r is independently selected from 1 and 2;
each t is independently selected from 1, 2, and 3.

2. The compound of claim 1 or a pharmaceutically acceptable salt thereof, wherein Q is selected from heteroaryl.

3. The compound of claim 2 or a pharmaceutically acceptable salt thereof, wherein Q is selected from pyridyl, pyridazinyl and 5,6,7,8-tetrahydro-1,6-naphthyridinyl.

4. The compound of claim 3 or a pharmaceutically acceptable salt thereof, wherein Q is selected from pyridin-2-yl, pyridazin-3-yl and 5,6,7,8-tetrahydro-1,6-naphthyridin-2-yl.

5. The compound of claim 1 or a pharmaceutically acceptable salt thereof, wherein $R^1$ is selected from hydrogen, $C_{1-10}$ alkyl, heterocyclyl and heterocyclyl-$C_{1-4}$ alkyl, wherein heterocyclyl is unsubstituted or substituted with at least one substituent independently selected from R⁶ᵃ, wherein each R⁶ᵃ is independently selected from $C_{1-10}$ alkyl, —NR⁷R⁸, —(CR⁹R¹⁰)$_t$OR⁸, —OR⁸, —C(O)R⁷, —(CR⁹R¹⁰)$_r$S(O)$_r$R⁸; wherein R⁷, R⁸, R⁹, R¹⁰, t and r are described as in claim 1.

6. The compound of claim 5 or a pharmaceutically acceptable salt thereof, wherein Q is selected from pyridin-2-yl, pyridazin-3-yl, and R¹ is selected from heterocyclyl and heterocyclyl-$C_{1-4}$alkyl groups consisting of the following groups:

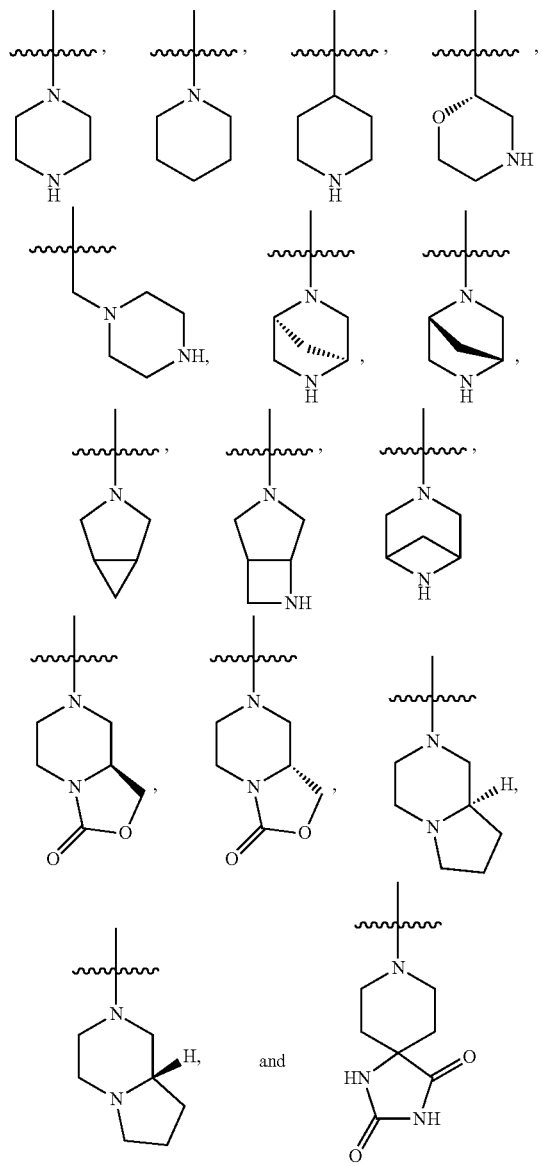

each heterocyclyl is unsubstituted or substituted with at least one independently selected from R⁶ᵃ, wherein each R⁶ᵃ is independently selected from $C_{1-10}$ alkyl, —NR⁷R⁸, —(CR⁹R¹⁰)$_t$OR⁸, —OR⁸, —C(O)R⁷, —C(O)NR⁷R⁸, —(CR⁹R¹⁰)$_r$S(O)$_r$R⁸; wherein R⁷, R⁸, R⁹, R¹⁰, t and r are described as in claim 1.

7. A compound of claim 5 or a pharmaceutically acceptable salt thereof, wherein R⁶ᵃ is independently selected from hydrogen, methyl, ethyl, hydroxyl, hydroxymethyl, hydroxyethyl, hydroxyacetyl, methoxymethyl, methoxyethyl, acetyl, hydroxyacetyl, (methyl sulfonyl)ethyl, amino, carbamoyl, methylamino, and dimethylamino.

8. The compound claim 1 or a pharmaceutically acceptable salt thereof, wherein R² is selected from $C_{3-10}$ cycloalkyl, wherein cycloalkyl is unsubstituted or substituted with at least one substituent independently selected from R⁶ᵃ, R⁶ᵃ is described as in claim 1.

9. The compound of claim 8 or a pharmaceutically acceptable salt thereof, wherein R² is selected from cyclopentyl and cyclohexyl, wherein cyclohexyl is unsubstituted or substituted with methyl.

10. The compound claim 1 or a pharmaceutically acceptable salt thereof, wherein R³ and R⁴ are independently selected from hydrogen, $C_{1-10}$ alkyl and cyclopropyl.

11. The compound of claim 1 or a pharmaceutically acceptable salt thereof, wherein R³ and R⁴ together with the nitrogen atoms to which they are attached form azetidinyl, pyrrolidinyl, piperidinyl, piperazinyl, and morpholino, wherein the formed ring is unsubstituted or substituted with methyl, hydroxyl, and methoxy.

12. The compound claim 1 or a pharmaceutically acceptable salt thereof, wherein R⁵ is independently selected from hydrogen, $C_{1-10}$ alkyl and —C(O)R⁷, wherein R⁷ is selected from methyl and hydroxymethyl.

13. The compound of claim 1, selected from
7-cyclopentyl-N,N-dimethyl-2-(5-(piperazin-1-yl)pyridin-2-ylamino)thieno[3,2-d]pyrimidine-6-carboxamide,
7-cyclopentyl-N,N-dimethyl-2-(5-(4-methylpiperazin-1-yl)pyridin-2-ylamino)thieno[3,2-d]pyrimidine-6-carboxamide,
(S)-7-cyclopentyl-N,N-dimethyl-2-((5-(3-oxotetrahydro-3H-oxazolo[3,4-a]pyrazin-7(1H)-yl)pyridin-2-yl)amino)thieno[3,2-d]pyrimidine-6-carboxamide,
(R)-7-cyclopentyl-N,N-dimethyl-2-((5-(3-oxotetrahydro-3H-oxazolo[3,4-a]pyrazin-7(1H)-yl)pyridin-2-yl)amino)thieno[3,2-d]pyrimidine-6-carboxamide,
(R)-7-cyclopentyl-N,N-dimethyl-2-((5-(morpholin-2-yl)pyridin-2-yl)amino)thieno[3,2-d]pyrimidine-6-carboxamide,
2-((5-(4-aminopiperidin-1-yl)pyridin-2-yl)amino)-7-cyclopentyl-N,N-dimethylthieno[3,2-d]pyrimidine-6-carboxamide,
7-cyclopentyl-N,N-dimethyl-2-((5-(4-(methylamino)piperidin-1-yl)pyridin-2-yl)amino)thieno[3,2-d]pyrimidine-6-carboxamide,
7-cyclopentyl-2-((5-(4-(dimethylamino)piperidin-1-yl)pyridin-2-yl)amino)-N,N-dimethylthieno[3,2-d]pyrimidine-6-carboxamide,
(S)-7-cyclopentyl-2-((5-(3-(methoxymethyl)piperazin-1-yl)pyridin-2-yl)amino)-N,N-dimethylthieno[3,2-d]pyrimidine-6-carboxamide,
(S)-7-cyclopentyl-2-((5-(3-(methoxymethyl)-4-methylpiperazin-1-yl)pyridin-2-yl)amino)-N,N-dimethylthieno[3,2-d]pyrimidine-6-carboxamide,
(S)-7-cyclopentyl-2-((5-(4-ethyl-3-(methoxymethyl)piperazin-1-yl)pyridin-2-yl)amino)-N,N-dimethylthieno[3,2-d]pyrimidine-6-carboxamide,
(S)-7-cyclopentyl-2-((5-(3-(hydroxymethyl)piperazin-1-yl)pyridin-2-yl)amino)-N,N-dimethylthieno[3,2-d]pyrimidine-6-carboxamide,
(S)-7-cyclopentyl-2-((5-(3-(hydroxymethyl)-4-methylpiperazin-1-yl)pyridin-2-yl)amino)-N,N-dimethylthieno[3,2-d]pyrimidine-6-carboxamide,
(S)-7-cyclopentyl-2-((5-(4-ethyl-3-(hydroxymethyl)piperazin-1-yl)pyridin-2-yl)amino)-N,N-dimethylthieno[3,2-d]pyrimidine-6-carboxamide, (R)-7-cyclopentyl-2-((5-(3-(methoxymethyl)piperazin-1-yl)pyridin-2-yl)amino)-N,N-dimethylthieno[3,2-d]pyrimidine-6-carboxamide, (R)-7-cyclopentyl-2-((5-(3-(methoxymethyl)-4-methylpiperazin-1-yl)pyridin-2-yl)amino)-N,N-dimethylthieno[3,2-d]pyrimidine-6-carboxamide, (R)-7-cyclopentyl-2-((5-(4-ethyl-3-(methoxymethyl)piperazin-1-yl)pyridin-2-yl)amino)-N,N-dimethylthieno[3,2-d]pyrimidine-6-carboxamide, (R)-7-cyclopentyl-2-((5-(3-(hydroxymethyl)piperazin-1-yl)pyridin-2-yl)amino)-N,N-dimethylthieno[3,2-d]pyrimidine-6-carboxamide, (R)-7-cyclopentyl-2-((5-(3-(hydroxymethyl)-4-methylpiperazin-1-yl)pyridin-2-yl)amino)-N,N-dimethylthieno[3,2-d]pyrimidine-6-carboxamide, (R)-7-cyclopentyl-2-((5-(4-ethyl-3-(hydroxymethyl)piperazin-1-yl)pyridin-2-yl)amino)-N,N-dimethylthieno[3,2-d]pyrimidine-6-carboxamide, 7-cyclopentyl-N,N-dimethyl-2-((5-(piperidin-4-yl)pyridin-2-yl)amino)thieno[3,2-d]pyrimidine-6-carboxamide, 7-cyclopentyl-N,N-dimethyl-2-((5-(1-methylpiperidin-4-yl)pyridin-2-yl)amino)thieno[3,2-d]pyrimidine-6-carboxamide, 2-((5-(6-amino-3-azabicyclo[3.1.0]hexan-3-yl)pyridin-2-yl)amino)-7-cyclopentyl-N,N-dimethylthieno[3,2-d]pyrimidine-6-carboxamide, 7-cyclopentyl-N,N-dimethyl-2-((5-(piperazin-1-ylmethyl)pyridin-2-yl)amino)thieno[3,2-d]pyrimidine-6-carboxamide, 7-cyclopentyl-N,N-dimethyl-2-((5-((4-methylpiperazin-1-yl)methyl)pyridin-2-yl)amino)thieno[3,2-d]pyrimidine-6-carboxamide, 7-cyclopentyl-2-((5-((4-ethylpiperazin-1-yl)methyl)pyridin-2-yl)amino)-N,N-dimethylthieno[3,2-d]pyrimidine-6-carboxamide, 2-(5-((1S,4S)-2,5-diazabicyclo[2.2.1]heptan-2-yl)pyridin-2-yl)amino)-7-cyclopentyl-N,N-dimethylthieno[3,2-d]pyrimidine-6-carboxamide, 7-cyclopentyl-N,N-dimethyl-2-((5-((1S,4S)-5-methyl-2,5-diazabicyclo[2.2.1]heptan-2-yl)pyridin-2-yl)amino)thieno[3,2-d]pyrimidine-6-carboxamide, (R)-7-cyclopentyl-2-((5-(hexahydropyrrolo[1,2-a]pyrazin-2(1H)-yl)pyridin-2-yl)amino)-N,N-dimethylthieno[3,2-d]pyrimidine-6-carboxamide, (S)-7-cyclopentyl-2-((5-(hexahydropyrrolo[1,2-a]pyrazin-2(1H)-yl)pyridin-2-yl)amino)-N,N-dimethylthieno[3,2-d]pyrimidine-6-carboxamide, 2-((5-((1R,4R)-2,5-diazabicyclo[2.2.1]heptan-2-yl)pyridin-2-yl)amino)-7-cyclopentyl-N,N-dimethylthieno[3,2-d]pyrimidine-6-carboxamide, 2-((5-(3,6-diazabicyclo[3.1.1]heptan-3-yl)pyridin-2-yl)amino)-7-cyclopentyl-N,N-dimethylthieno[3,2-d]pyrimidine-6-carboxamide, 7-cyclopentyl-N,N-dimethyl-2-((5-(6-methyl-3,6-diazabicyclo[3.1.1]heptan-3-yl)pyridin-2-yl)amino)thieno[3,2-d]pyrimidine-6-carboxamide, 7-cyclopentyl-2-((5-(6-ethyl-3,6-diazabicyclo[3.1.1]heptan-3-yl)pyridin-2-yl)amino)-N,N-dimethylthieno[3,2-d]pyrimidine-6-carboxamide, 7-cyclopentyl-2-((5-((7R,8aR)-7-hydroxyhexahydropyrrolo[1,2-a]pyrazin-2(1H)-yl)pyridin-2-yl)amino)-N,N-dimethylthieno[3,2-d]pyrimidine-6-carboxamide, 7-cyclopentyl-2-((5-((7S,8aR)-7-hydroxyhexahydropyrrolo[1,2-a]pyrazin-2(1H)-yl)pyridin-2-yl)amino)-N,N-dimethylthieno[3,2-d]pyrimidine-6-carboxamide, 7-cyclopentyl-2-((5-((7R,8aS)-7-hydroxyhexahydropyrrolo[1,2-a]pyrazin-2(1H)-yl)pyridin-2-yl)amino)-N,N-dimethylthieno[3,2-d]pyrimidine-6-carboxamide, 2-((5-(3,6-diazabicyclo[3.2.0]heptan-3-yl)pyridin-2-yl)amino)-7-cyclopentyl-N,N-dimethylthieno[3,2-d]pyrimidine-6-carboxamide, 7-cyclopentyl-N,N-dimethyl-2-((5-(6-methyl-3,6-diazabicyclo[3.2.0]heptan-3-yl)pyridin-2-yl)amino)thieno[3,2-d]pyrimidine-6-carboxamide, 7-cyclopentyl-2-((5-(6-ethyl-3,6-diazabicyclo[3.2.0]heptan-3-yl)pyridin-2-yl)amino)-N,N-dimethylthieno[3,2-d]pyrimidine-6-carboxamide, 7-cyclopentyl-N,N-dimethyl-2-((6-(piperazin-1-yl)pyridazin-3-yl)amino)thieno[3,2-d]pyrimidine-6-carboxamide, 7-cyclopentyl-N,N-dimethyl-2-((6-(4-methylpiperazin-1-yl)pyridazin-3-yl)amino)thieno[3,2-d]pyrimidine-6-carboxamide, 2-((6-(4-acetylpiperazin-1-yl)pyridazin-3-yl)amino)-7-cyclopentyl-N,N-dimethylthieno[3,2-d]pyrimidine-6-carboxamide, 7-cyclopentyl-2-((6-(4-(2-hydroxyacetyl)piperazin-1-yl)pyridazin-3-yl)amino)-N,N-dimethylthieno[3,2-d]pyrimidine-6-carboxamide, 7-cyclopentyl-N,N-dimethyl-2-((6-(4-(2-(methylsulfonyl)ethyl)piperazin-1-yl)pyridazin-3-yl)amino)thieno[3,2-d]pyrimidine-6-carboxamide, 7-cyclopentyl-N,N-dimethyl-2-((5,6,7,8-tetrahydro-1,6-naphthyridin-2-yl)amino)thieno[3,2-d]pyrimidine-6-carboxamide, 7-cyclopentyl-N,N-dimethyl-2-((6-methyl-5,6,7,8-tetrahydro-1,6-naphthyridin-2-yl)amino)thieno[3,2-d]pyrimidine-6-carboxamide, 7-cyclopentyl-2-((5-(4-(2-hydroxyethyl)piperazin-1-yl)pyridin-2-yl)amino)-N,N-dimethylthieno[3,2-d]pyrimidine-6-carboxamide, 7-cyclopentyl-2-((5-(4-(2-methoxyethyl)piperazin-1-yl)pyridin-2-yl)amino)-N,N-dimethylthieno[3,2-d]pyrimidine-6-carboxamide, 7-cyclopentyl-N,N-dimethyl-2-((5-(4-(2-(methylsulfonyl)ethyl)piperazin-1-yl)pyridin-2-yl)amino)thieno[3,2-d]pyrimidine-6-carboxamide, 7-cyclopentyl-2-((5-(4-ethylpiperazin-1-yl)pyridin-2-yl)amino)-N,N-dimethylthieno[3,2-d]pyrimidine-6-carboxamide, 7-cyclopentyl-2-((5-((3S,5R)-3,5-dimethylpiperazin-1-yl)pyridin-2-yl)amino)-N,N-dimethylthieno[3,2-d]pyrimidine-6-carboxamide 7-cyclopentyl-N,N-dimethyl-2-((5-((3S,5R)-3,4,5-trimethylpiperazin-1-yl)pyridin-2-yl)amino)thieno[3,2-d]pyrimidine-6-carboxamide 7-cyclopentyl-2-((5-((3S,5R)-4-ethyl-3,5-dimethylpiperazin-1-yl)pyridin-2-yl)amino)-N,N-dimethylthieno[3,2-d]pyrimidine-6-carboxamide 7-cyclopentyl-N,N-dimethyl-2-((5-(1-methyl-2,4-dioxo-1,3,8-triazaspiro[4.5]decan-8-yl)pyridin-2-yl)amino)thieno[3,2-d]pyrimidine-6-carboxamide 2-((5-(4-carbamoyl-4-(methylamino)piperidin-1-yl)pyridin-2-yl)amino)-7-cyclopentyl-N,N-dimethylthieno[3,2-d]pyrimidine-6-carboxamide azetidin-1-yl(7-cyclopentyl-2-((5-(piperazin-1-yl)pyridin-2-yl)amino)thieno[3,2-d]pyrimidin-6-yl)methanone, (7-cyclopentyl-2-((5-(piperazin-1-yl)pyridin-2-yl)amino)thieno[3,2-d]pyrimidin-6-yl)(3-methoxyazetidin-1-yl)methanone, (7-cyclopentyl-2-((5-(piperazin-1-yl)pyridin-2-yl)amino)thieno[3,2-d]pyrimidin-6-yl)(3-hydroxyazetidin-1-yl)methanone, (7-cyclopentyl-2-((5-(piperazin-1-yl)pyridin-2-yl)amino)thieno[3,2-d]pyrimidin-6-yl)(piperidin-1-yl)methanone, (7-cyclopentyl-2-((5-(piperazin-1-yl)pyridin-2-yl)amino)thieno[3,2-d]pyrimidin-6-yl)(4-methylpiperazin-1-yl)methanone, (7-cyclopentyl-2-((5-(piperazin-1-yl)pyridin-2-yl)amino)thieno[3,2-d]pyrimidin-6-yl)(piperazin-1-yl)methanone, 7-cyclopentyl-N-cyclopropyl-2-((5-(piperazin-1-yl)pyridin-2-yl)amino)thieno[3,2-d]pyrimidine-6-carboxamide, (7-cyclopentyl-2-((5-(piperazin-1-yl)pyridin-2-yl)amino)thieno[3,2-d]pyrimidin-6-yl)(pyrrolidin-1-yl)methanone, 7-cyclopentyl-2-((5-(piperazin-1-yl)pyridin-2-yl)amino)thieno[3,2-d]pyrimidine-6-carboxamide, 7-cyclopentyl-N-methyl-2-((5-(piperazin-1-yl)pyridin-2-yl)amino)thieno[3,2-d]pyrimidine-6-carboxamide, 7-cyclopentyl-N-ethyl-2-((5-(piperazin-1-yl)pyridin-2-yl)amino)thieno[3,2-d]pyrimidine-6-carboxamide, (7-cyclopentyl-2-((5-(piperazin-1-yl)pyridin-2-yl)amino)thieno[3,2-d]pyrimidin-6-yl)(morpholino)methanone, azetidin-1-yl(7-cyclopentyl-2-((5-(4-methylpiperazin-1-yl)pyridin-2-yl)amino)thieno[3,2-d]pyrimidin-6-yl)methanone, (7-cyclopentyl-2-((5-(4-methylpiperazin-1-yl)pyridin-2-yl)amino)thieno[3,2-d]pyrimidin-6-yl)(3-methoxyazetidin-1-yl)methanone, (7-cyclopentyl-2-((5-(4-methylpiperazin-1-yl)pyridin-2-yl)amino)thieno[3,2-d]pyrimidin-6-yl)(piperidin-1-yl)methanone, (7-cyclopentyl-2-((5-(4-methylpiperazin-1-yl)pyridin-2-yl)amino)thieno[3,2-d]pyrimidin-6-yl)(4-methylpiperazin-1-yl)methanone, 7-cyclopentyl-N-cyclopropyl-2-((5-(4-methylpiperazin-1-yl)pyridin-2-yl)amino)thieno[3,2-d]pyrimidine-6-carboxamide, (7-cyclopentyl-2-((5-(4-methylpiperazin-1-yl)pyridin-2-yl)amino)thieno[3,2-d]pyrimidin-6-yl)(pyrrolidin-1-yl)methanone, 7-cyclopentyl-N-methyl-2-((5-(4-methylpiperazin-1-yl)pyridin-2-yl)amino)thieno[3,2-d]pyrimidine-6-carboxamide, (7-cyclopentyl-2-((5-(4-methylpiperazin-1-yl)pyridin-2-yl)amino)thieno[3,2-d]pyrimidin-6-yl)(morpholino)methanone, N,N-dimethyl-7-((1r,4r)-4-methylcyclohexyl)-2-((5-(piperazin-1-yl)pyridin-2-yl)amino)thieno[3,2-d]pyrimidine-6-carboxamide, N,N-dimethyl-7-((1r,4r)-4-methylcyclohexyl)-2-((5-(4-methylpiperazin-1-yl)pyridin-2-yl)amino)thieno[3,2-d]pyrimidine-6-carboxamide, N,N-dimethyl-7-((1r,4r)-4-methylcyclohexyl)-2-((5,6,7,8-tetrahydro-1,6-naphthyridin-2-yl)amino)thieno[3,2-d]pyrimidine-6-carboxamide, N,N-dimethyl-2-((6-methyl-5,6,7,8-tetrahydro-1,6-naphthyridin-2-yl)amino)-7-((1r,4r)-4-methylcyclohexyl)thieno[3,2-d]pyrimidine-6-carboxamide, 2-((6-acetyl-5,6,7,8-tetrahydro-1,6-naphthyridin-2-yl)amino)-N,N-dimethyl-7-((1r,4r)-4-methylcyclohexyl)thieno[3,2-d]pyrimidine-6-carboxamide, 2-((6-(2-hydroxyacetyl)-5,6,7,8-tetrahydro-1,6-naphthyridin-2-yl)amino)-N,N-dimethyl-7-((1r,4r)-4-methylcyclohexyl)thieno[3,2-d]pyrimidine-6-carboxamide, N,N-dimethyl-7-((1r,4r)-4-methylcyclohexyl)-2-((6-(piperazin-1-yl)pyridazin-3-yl)amino)thieno[3,2-d]pyrimidine-6-carboxamide, N,N-dimethyl-7-((1r,4r)-4-methylcyclohexyl)-2-((6-(4-methylpiperazin-1-yl)pyridazin-3-yl)amino)thieno[3,2-d]pyrimidine-6-carboxamide, 2-((6-(4-acetylpiperazin-1-yl)pyridazin-3-yl)amino)-N,N-dimethyl-7-((1r,4r)-4-methylcyclohexyl)thieno[3,2-d]pyrimidine-6-carboxamide, 2-((6-(4-(2-hydroxyacetyl)piperazin-1-yl)pyridazin-3-yl)amino)-N,N-dimethyl-7-((1r,4r)-4-methylcyclohexyl)thieno[3,2-d]pyrimidine-6-carboxamide, or pharmaceutically acceptable salt thereof.

14. A pharmaceutical composition comprising a compound of claim 1 or a pharmaceutically acceptable salt thereof, and at least one pharmaceutically acceptable carrier.

* * * * *